(12) United States Patent
Priepke et al.

(10) Patent No.: US 8,486,968 B2
(45) Date of Patent: Jul. 16, 2013

(54) COMPOUNDS

(75) Inventors: Henning Priepke, Warthausen (DE); Henri Doods, Warthausen (DE); Raimund Kuelzer, Mittelbiberach (DE); Roland Pfau, Biberach an der Riss (DE); Dirk Stenkamp, Biberach an der Riss (DE); Benjamin Pelcman, Stockholm (SE); Robert Roenn, Uppsala (SE); Dimitrijs Lubriks, Riga (LV); Edgars Suna, Riga (LV)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 39 days.

(21) Appl. No.: 13/314,574

(22) Filed: Dec. 8, 2011

(65) Prior Publication Data

US 2012/0309755 A1 Dec. 6, 2012

(30) Foreign Application Priority Data

Dec. 10, 2010 (EP) .................................. 10194459

(51) Int. Cl.
*A01N 43/42* (2006.01)
*A61K 31/44* (2006.01)
*A61K 31/135* (2006.01)
*A01N 33/18* (2006.01)
*A61K 31/04* (2006.01)

(52) U.S. Cl.
USPC ........................... 514/303; 514/646; 514/741

(58) Field of Classification Search
None
See application file for complete search history.

(56) References Cited

U.S. PATENT DOCUMENTS

| | | | |
|---|---|---|---|
| 6,608,084 B1 | 8/2003 | Bourzat et al. | |
| 2004/0198768 A1 | 10/2004 | Park Choo et al. | |
| 2006/0287344 A1 | 12/2006 | Albers et al. | |
| 2007/0060598 A1 | 3/2007 | Albers et al. | |
| 2010/0004301 A1 | 1/2010 | Pelcman et al. | |
| 2010/0256188 A1* | 10/2010 | Pfau et al. | 514/322 |
| 2011/0275656 A1 | 11/2011 | Pfau et al. | |
| 2011/0312935 A1 | 12/2011 | Pfau et al. | |
| 2012/0115902 A1 | 5/2012 | Pfau et al. | |
| 2012/0122930 A1 | 5/2012 | Pfau et al. | |
| 2012/0149676 A1 | 6/2012 | Priepke et al. | |
| 2012/0196897 A1 | 8/2012 | Pfau et al. | |
| 2012/0208839 A1 | 8/2012 | Priepke et al. | |
| 2012/0214786 A1 | 8/2012 | Priepke et al. | |
| 2012/0309738 A1 | 12/2012 | Priepke et al. | |
| 2012/0309755 A1 | 12/2012 | Priepke et al. | |

FOREIGN PATENT DOCUMENTS

| EP | 0034743 A1 | 9/1981 |
|---|---|---|
| EP | 0295656 A1 | 12/1988 |
| EP | 0419210 A1 | 3/1991 |
| EP | 1069124 A1 | 1/2001 |
| FR | 2851563 A1 | 8/2004 |
| FR | 2852957 A1 | 10/2004 |
| WO | 0015612 A1 | 3/2000 |
| WO | 0049005 A1 | 8/2000 |
| WO | 0061580 A1 | 10/2000 |
| WO | 0068213 A1 | 11/2000 |
| WO | 0125238 A2 | 4/2001 |
| WO | 03053939 A1 | 7/2003 |
| WO | 03074515 A1 | 9/2003 |
| WO | 03082272 A1 | 10/2003 |
| WO | 2004005323 A2 | 1/2004 |
| WO | 2004035740 A2 | 4/2004 |
| WO | 2004072068 A1 | 8/2004 |
| WO | 2004085425 A1 | 10/2004 |
| WO | 2004089951 A1 | 10/2004 |
| WO | 2005044793 A2 | 5/2005 |
| WO | 2005070906 A1 | 8/2005 |
| WO | 2005070920 A1 | 8/2005 |
| WO | 2005123674 A1 | 12/2005 |
| WO | 2006077366 A1 | 7/2006 |
| WO | 2006090167 A2 | 8/2006 |
| WO | 2007095124 A2 | 8/2007 |
| WO | 2007127382 A1 | 11/2007 |
| WO | 2008009924 A2 | 1/2008 |
| WO | 2008035956 A1 | 3/2008 |
| WO | 2008071944 A1 | 6/2008 |
| WO | 2008129276 A1 | 10/2008 |
| WO | 2010034796 A1 | 4/2010 |
| WO | 2010034797 A1 | 4/2010 |
| WO | 2010034798 A1 | 4/2010 |
| WO | 2010034799 A1 | 4/2010 |
| WO | 2010100249 A1 | 9/2010 |
| WO | WO 2010100249 A1 * | 9/2010 |

OTHER PUBLICATIONS

Lala et al., Cancer and Metastasis reviews (1998), 17 (1), 91-106.
Golub et al., Science (1999), vol. 286, 531-537.
Cancer [online], [retrieved on Jul. 6, 2007]. Retrieved from the internet, URL http://www.nlm.nih.gov/medlineplus/cancer.html.
Cancer [online], [retrieved on Jul. 6, 2007]. Retrieved from the internet, URL http://en.wikipedia.org/wikiICancer.com.
R.D. Carpenter et al., Carbodiimide-based benzinidazole library method, Journal of Combinatorial Chemistry, Oct. 27, 2006, pp. 907-914, vol. 8, No. 6.
International Search Report Form PCT/ISA/210 and Written Opinion Form PCT/ISA/237 for corresponding PCT/EP2011/072258; date of mailing: Feb. 14, 2012.
D.J. Gale et al., The Amidomethylation of Some N,N-Dialkylanilines; Aust.J. Chem.; pp. 2447-2458; vol. 28; 1975.

* cited by examiner

*Primary Examiner* — Jeffrey S. Lundgren
*Assistant Examiner* — Michael Schmitt
(74) *Attorney, Agent, or Firm* — Michael P. Morris; Philip I. Datlow

(57) ABSTRACT

This invention relates to compounds of formula I

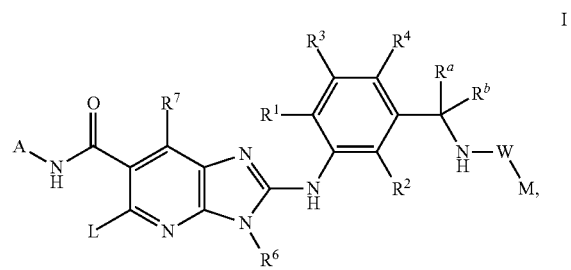

their use as inhibitors of the microsomal prostaglandin $E_2$ synthase-1 (mPGES-1), pharmaceutical compositions containing them, and their use as medicaments for the treatment and/or prevention of inflammatory diseases and associated conditions. A, L, M, W, $R^1$, $R^2$, $R^3$, $R^4$, $R^6$, $R^7$, $R^a$, $R^b$ have meanings given in the description.

14 Claims, No Drawings

COMPOUNDS

FIELD OF THE INVENTION

This invention relates to novel compounds, which are inhibitors of the microsomal prostaglandin $E_2$ synthase-1 (mPGES-1), pharmaceutical compositions containing them, and their use as medicaments for the treatment and/or prevention of inflammatory diseases and associated conditions such as inflammatory/nociceptive pain.

BACKGROUND OF THE INVENTION

There are many acute and chronic diseases/disorders that are inflammatory in their nature including but not limited to rheumatoid diseases e.g. rheumatoid arthritis, osteoarthritis, diseases of the visceral system e.g. inflammatory bowel syndrome, autoimmune diseases, e.g. lupus erythematodes, lung diseases like asthma and COPD. Current treatment with non-steroidal anti-inflammatory drugs (NSAIDs) and cyclooxygenase (COX)-2 inhibitors are efficacious, but show a prevalence for gastrointestinal and cardiovascular side effects. There is a high need for new treatment options showing equivalent efficacy with an improved side effect profile.

mPGES inhibitors may show such an improved side effect profile because they block the generation of $PGE_2$ in a more specific manner as described below.

NSAIDs and COX-2 inhibitors reduce inflammation and pain through inhibition of one or both isoformes of COX enzymes. The cyclooxygenase (COX) enzyme exists in two forms, one that is constitutively expressed in many cells and tissues (COX-1), and one that in most cells and tissues is induced by pro-inflammatory stimuli, such as cytokines, during an inflammatory response (COX-2). COXs metabolise arachidonic acid to the unstable intermediate prostaglandin $H_2$ ($PGH_2$). $PGH_2$ is further metabolized to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects. $PGE_2$ in particular is known to be a strong pro-inflammatory mediator, and is also known to induce fever, inflammation and pain. Consequently, numerous drugs were developed with a view to inhibiting the formation of $PGE_2$, including "NSAIDs" (non-steroidal antiinflammatory drugs) and "coxibs" (selective COX-2 inhibitors). These drugs act predominantly by inhibition of COX-1 and/or COX-2, thereby reducing the formation of $PGE_2$.

However, the inhibition of COXs has the disadvantage that it results in the reduction of the formation of all metabolites downstream of $PGH_2$, some of which are known to have beneficial properties. In view of this, drugs which act by inhibition of COXs are therefore known/suspected to cause adverse biological effects.

For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

An alternative treatment of inflammatory diseases that does not give rise to the above-mentioned side effects would thus be of real benefit in the clinic. In particular, a drug that preferably inhibits the transformation of $PGH_2$ to the pro-inflammatory mediator $PGE_2$ selectively might be expected to reduce the inflammatory response in the absence of a corresponding reduction of the formation of other, beneficial arachidonic acid metabolites. Such inhibition would accordingly be expected to alleviate the undesirable side-effects mentioned above.

$PGH_2$ may be transformed to $PGE_2$ by prostaglandin E synthases (PGES). Two microsomal prostaglandin E synthases (mPGES-1 and mPGES-2), and one cytosolic prostaglandin E synthase (cPGES) have been described. mPGES-1 is proposed to be closely linked to COX-2 and both enzyme's are upregulated during e.g. inflammation. Thus agents that are capable of inhibiting the action of mPGES-1 and thereby reducing the formation of $PGE_2$ are likely to be of benefit for the treatment of inflammation and more general acute and chronic pain conditions Benzimidazole and imidazopyridine derivatives with m PGES-1 inhibitory activity are disclosed in WO 2010/034796, WO 2010/034797, WO 2010/034798, WO 2010/034799.

WO 2010/100249 describes a broad class of different 2-arylamino benzimidazoles in which the aryl group bears a particular side chain.

Compounds of the present invention are distinguished over related imidazopyridines in WO 2010/034799 by enhanced biological activity in a cell-based assay.

Compounds with a similar affinity for the m PGES-1 enzyme as measured in the enzyme assay may have different potencies in the cell-based assay. Data from a cell based pharmacological assay when compared with data from an enzyme assay are considered to allow for a better predictibility and estimation of therapeutic effective concentrations/doses.

Compounds of the present invention show high potency in both assays. Consequently, they are likely to be more suitable for the in-vivo use.

DETAILED DESCRIPTION OF THE INVENTION

The present invention provides a compound of formula I,

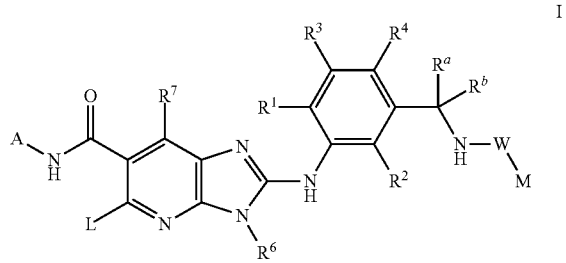

in which
$R^1$ represents halo, OH, —CN, $C_{1-3}$ alkyl, $C_{2-6}$ alkynyl, $OC_{1-3}$ alkyl which latter three groups are optionally substituted by one or more substituents selected from fluoro, —CN, =O, OH, —OCH$_3$, —OCF$_3$;
$R^2$, $R^3$ and $R^4$ independently represent hydrogen, halo, —CN, $C_{1-3}$ alkyl, $OC_{1-3}$ alkyl which latter two groups are optionally substituted by one or more substituents selected from fluoro, —CN, =O, OH, —OCH$_3$, —OCF$_3$;
$R^a$, $R^b$ independently represent hydrogen, $C_{1-3}$ alkyl optionally substituted by one or more fluorine atoms,
or both together with the carbon atom which they are bound to, form a $C_{3-7}$ cycloalkylene ring, or a 4-6 membered heterocycloalkylene ring which latter two rings are optionally substituted by one or more fluorine atoms;
W represents —C(O)—, —S(O)—, —S(O)$_2$—, —C(O)O—, —C(O)NR$^d$— which groups are bound to the nitrogen of the —NH-moiety via carbon or sulfur atom;

$R^d$ represents hydrogen, $C_{1-3}$ alkyl;

M represents $C_{1-8}$ alkyl, $C_{2-8}$ alkynyl, $C_{3-8}$ cycloalkyl-$C_{0-4}$ alkyl, 4-10 membered heterocycloalkyl-$C_{0-4}$alkyl-which latter four groups are optionally substituted by one or more groups selected from fluoro, —OH, =O, —CN, —NH$_2$, $C_{1-3}$ alkyl, —NH($C_{1-3}$ alkyl), —N($C_{1-3}$ alkyl)$_2$, azetidinyl, pyrrolidinyl, piperidinyl, —O$C_{1-3}$ alkyl [which latter seven groups can be substituted by one or more substituents selected from fluoro, OH, —CN, O$C_{1-2}$ alkyl (which latter alkyl group is optionally substituted by one or more fluorine atoms)], aryl, heteroaryl [which latter two groups are optionally substituted by one or more substituents selected from halo, OH, —CN, $C_{1-3}$ alkyl, O$C_{1-3}$ alkyl (which latter two alkyl groups are optionally substituted by one or more fluorine atoms)], or aryl, heteroaryl which latter two groups are optionally substituted by one or more substituents selected from halo, —OH, —CN, —NH$_2$, aryl, heteroaryl [which latter two groups are optionally substituted by one or more substituents selected from halo, OH, —CN, $C_{1-3}$ alkyl, —O$C_{1-3}$ alkyl (which latter two alkyl groups are optionally substituted by one or more fluorine atoms)], $C_{1-7}$ alkyl, $C_{2-7}$ alkynyl, $C_{3-7}$ cycloalkyl, 4-7 membered heterocyclo-alkyl, —NH($C_{1-3}$ alkyl), —N($C_{1-3}$ alkyl)$_2$, —O$C_{1-3}$ alkyl, —O—$C_{0-2}$alkyl-aryl, —S$C_{1-3}$ alkyl, (which latter alkyl, alkynyl, heterocycloalkyl, aryl or cycloalkyl groups are optionally substituted by one or more substituents selected from fluoro, —CN, =O, —NH$_2$, —NH($C_{1-3}$ alkyl), —N($C_{1-3}$ alkyl)$_2$, —OH, —O$C_{1-3}$alkyl)];

$R^6$ represents hydrogen, $C_{1-5}$ alkyl, $C_{3-6}$ alkynyl, 4-7 membered heterocyclo-alkyl-$C_{0-2}$alkyl or $C_{3-7}$cycloalkyl-$C_{0-2}$alkyl (which latter four groups are optionally substituted by one or more substituents selected from fluoro, —CN, =O, $C_{1-3}$ alkyl, —OH, —NH$_2$, —O$C_{1-3}$ alkyl, —NH($C_{1-3}$ alkyl), —N($C_{1-3}$ alkyl)$_2$);

$R^7$ represents hydrogen, halo, —CN, $C_{1-5}$ alkyl, $C_{3-5}$ cycloalkyl-$C_{0-2}$alkyl-, $C_{1-5}$ alkyl-O—, $C_{3-5}$cycloalkyl-$C_{0-2}$ alkyl-O— (in which latter four groups the alkyl and cycloalkyl fragments are optionally substituted by one or more substituents selected from fluoro, —CN, =O, OH, —O$C_{1-3}$ alkyl or by one or more $C_{1-3}$ alkyl groups which are optionally substituted by one or more fluorine atoms);

L represents —NH$_2$, —NHR$^{10}$, —NR$^{10}$R$^{11}$, or a 4-10-membered heterocycloalkyl group which is bound to the benzimidazole through a nitrogen atom, and which is optionally substituted by one or more substituents R$^{12}$;

$R^{10}$ and $R^{11}$ independently represent $C_{1-7}$ alkyl, $C_{3-7}$ cycloalkyl-$C_{0-4}$ alkyl-, $C_{4-7}$ heterocycloalkyl-$C_{0-4}$ alkyl-[which latter three groups are optionally substituted by one or more groups selected from fluoro, —OH, NH$_2$, —CN, $C_{1-3}$ alkyl, —NH($C_{1-3}$ alkyl), —N($C_{1-3}$ alkyl)$_2$, —O$C_{1-5}$ alkyl, —O$C_{3-6}$ cycloalkyl, —O$C_{4-6}$ heterocycloalkyl (which latter six groups are optionally substituted by one or more selected from fluoro, —CF$_3$, —CHF$_2$, —CH$_2$F, —CH$_3$)], or aryl-$C_{0-4}$ alkyl-, heteroaryl-$C_{0-4}$ alkyl-[which latter two groups are optionally substituted by one or more substituents selected from halo, —OH, —CN, $C_{1-3}$ alkyl, $C_{3-5}$ cycloalkyl, $C_{1-3}$ alkyl-O—, $C_{3-5}$ cycloalkyl-O— (which latter four groups are optionally substituted by one or more fluorine atoms)];

each $R^{12}$ independently represents halo, —OH, —NH$_2$, =O, —CN, $C_{1-4}$ alkyl, $C_{3-5}$ cycloalkyl-$C_{0-2}$ alkyl-, $C_{4-5}$ heterocycloalkyl-$C_{0-2}$ alkyl-, $C_{1-4}$ alkyl-O—, $C_{1-3}$ alkyl-C(=O)—, —C(=O)—NH($C_{1-3}$ alkyl), —C(=O)—N($C_{1-3}$ alkyl)$_2$ [which latter seven groups are optionally substituted by one or more groups selected from: fluoro, —OH, oxo, —NH$_2$, —CN, $C_{1-3}$ alkyl, —NH($C_{1-3}$ alkyl), —N($C_{1-3}$ alkyl)$_2$, —O$C_{1-3}$ alkyl, —O$C_{3-5}$ cycloalkyl [which latter five groups are optionally substituted by one or more substituents selected from fluoro, —CF$_3$, —CHF$_2$, —CH$_2$F], or aryl-$C_{0-4}$ alkyl-, heteroaryl-$C_{0-4}$ alkyl-[which latter two groups are optionally substituted by one or more substituents selected from halo, —OH, —CN, $C_{1-3}$ alkyl, $C_{3-5}$ cycloalkyl, $C_{1-3}$ alkyl-O—, $C_{3-5}$ cycloalkyl-O— (which latter four groups are optionally substituted by one or more fluorine atoms)];

A represents $C_{1-8}$ alkyl, $C_{3-8}$ alkynyl, aryl-$C_{0-3}$alkyl-, $C_{3-8}$cycloalkyl-$C_{0-3}$alkyl-, 4-7 membered heterocycloalkyl-$C_{0-3}$ alkyl-, heteroaryl-$C_{0-3}$alkyl-in which latter six groups the alkyl-, alkynyl-, cycloalkyl- and heterocycloalkyl-fragments are optionally substituted by one or more substituents selected from R$^{14}$ and the aryl and heteroaryl fragments are optionally substituted by one or more substituents selected from R$^{15}$;

each $R^{14}$ independently represents fluoro, —OH, —CN, =O, —NH$_2$, —NH($C_{1-3}$ alkyl), —N($C_{1-3}$ alkyl)$_2$, —O$C_{1-6}$ alkyl, $C_{1-6}$alkyl (in which latter four groups the alkyl fragments are optionally substituted by one or more substituents selected from fluoro, —CN, =O, —NH$_2$, —NH($C_{1-3}$ alkyl), N($C_{1-3}$ alkyl)$_2$, —OH, —O$C_{1-3}$ alkyl) or aryl, heteroaryl [which latter two groups are optionally substituted by one or more substituents selected from halo, OH, —CN, $C_{1-3}$ alkyl, O$C_{1-3}$ alkyl (which latter two alkyl groups are optionally substituted by one or more fluorine atoms)];

each $R^{15}$ independently represents halo, —OH, —CN, —NH$_2$, aryl, heteroaryl [which latter two groups are optionally substituted by one or more substituents selected from halo, OH, —CN, $C_{1-3}$ alkyl, O$C_{1-3}$ alkyl (which latter two alkyl groups are optionally substituted by one or more fluorine atoms)], —NH($C_{1-3}$ alkyl), —N($C_{1-3}$ alkyl)$_2$, —O$C_{1-3}$ alkyl, $C_{1-7}$ alkyl, $C_{2-7}$ alkynyl, $C_{3-7}$ cycloalkyl, 4-7 membered heterocycloalkyl (which latter alkyl, alkynyl, heterocycloalkyl or cycloalkyl groups are optionally substituted by one or more substituents selected from fluoro, —CN, =O, —NH$_2$, —NH($C_{1-3}$ alkyl), N($C_{1-3}$ alkyl)$_2$, —OH, O$C_{1-3}$alkyl);

or a salt thereof, particularly a physiologically acceptable salt thereof.

Alternatively, the present invention provides a compound of formula I, in which $R^1$ represents halo, OH, —CN, $C_{1-3}$ alkyl, $C_{2-6}$ alkynyl, O$C_{1-3}$ alkyl which latter three groups are optionally substituted by one or more substituents selected from fluoro, —CN, =O, OH, —OCH$_3$, —OCF$_3$;

$R^2$, $R^3$ and $R^4$ independently represent hydrogen, halo, —CN, $C_{1-3}$ alkyl, O$C_{1-3}$ alkyl which latter two groups are optionally substituted by one or more substituents selected from fluoro, —CN, =O, OH, —OCH$_3$, —OCF$_3$;

$R^a$, $R^b$ independently represent hydrogen, $C_{1-3}$ alkyl optionally substituted by one or more fluorine atoms, or both together with the carbon atom which they are bound to, form a $C_{3-7}$ cycloalkylene ring, or a 4-6 membered heterocycloalkylene ring which latter two rings are optionally substituted by one or more fluorine atoms;

W represents —C(O)—, —S(O)—, —S(O)$_2$—, —C(O)O—, —C(O)NR$^d$— which groups are bound to the nitrogen of the —NH-moiety via carbon or sulfur atom;

$R^d$ represents hydrogen, $C_{1-3}$ alkyl;

M represents $C_{1-8}$ alkyl, $C_{2-8}$ alkynyl, $C_{3-8}$ cycloalkyl-$C_{0-4}$ alkyl, 4-10 membered heterocycloalkyl-$C_{0-4}$alkyl-which latter four groups are optionally substituted by one or more groups selected from fluoro, —OH, =O, —CN, —NH$_2$, $C_{1-3}$ alkyl, —NH($C_{1-3}$ alkyl), —N($C_{1-3}$ alkyl)$_2$, azetidinyl, pyrrolidinyl, piperidinyl, —O$C_{1-3}$ alkyl [which latter seven alkyl groups can be substituted by one or more substituents selected from fluoro, OH, —CN, O$C_{1-2}$ alkyl (which latter alkyl group is optionally substituted by one or more fluorine atoms)], aryl, heteroaryl [which latter two groups are optionally substituted by one or more substituents selected from halo, OH, —CN, $C_{1-3}$ alkyl, O$C_{1-3}$ alkyl (which latter two alkyl groups are optionally substituted by one or more fluorine atoms)], or aryl, heteroaryl which latter two groups are optionally substituted by one or more substituents selected from halo, —OH, —CN, —NH$_2$, aryl, heteroaryl [which latter two groups are optionally substituted by one or more substituents selected from halo, OH, —CN, $C_{1-3}$ alkyl, —O$C_{1-3}$ alkyl (which latter two alkyl groups are optionally substituted by one or more fluorine atoms)], $C_{1-7}$ alkyl, $C_{2-7}$ alkynyl, $C_{3-7}$ cycloalkyl, 4-7 membered heterocyclo-alkyl, —NH$_2$, —NH($C_{1-3}$ alkyl), —N($C_{1-3}$ alkyl)$_2$, —O$C_{1-3}$ alkyl, —O—$C_{0-2}$alkyl-aryl, —S$C_{1-3}$ alkyl, (which latter alkyl, alkynyl, heterocycloalkyl, aryl or cycloalkyl groups are optionally substituted by one or more substituents selected from fluoro, —CN, =O, —NH$_2$, —NH($C_{1-3}$ alkyl), —N($C_{1-3}$ alkyl)$_2$, —OH, —O$C_{1-3}$alkyl)];

$R^6$ represents hydrogen, $C_{1-5}$ alkyl, $C_{3-6}$ alkynyl, 4-7 membered heterocyclo-alkyl-$C_{0-2}$alkyl or $C_{3-7}$cycloalkyl-$C_{0-2}$alkyl (which latter four groups are optionally substituted by one or more substituents selected from fluoro, —CN, =O, $C_{1-3}$ alkyl, —OH, —NH$_2$, —O$C_{1-3}$ alkyl, —NH($C_{1-3}$ alkyl), —N($C_{1-3}$ alkyl)$_2$);

$R^7$ represents hydrogen, halo, —CN, $C_{1-5}$ alkyl, $C_{3-5}$ cycloalkyl-$C_{0-2}$alkyl-, $C_{1-5}$ alkyl-O—, $C_{3-5}$cycloalkyl-$C_{0-2}$ alkyl-O— (in which latter four groups the alkyl and cycloalkyl fragments are optionally substituted by one or more substituents selected from fluoro, —CN, =O, OH, —O$C_{1-3}$ alkyl or by one or more $C_{1-3}$ alkyl groups which are optionally substituted by one or more fluorine atoms);

L represents —NH$_2$, —NHR$^{10}$, —NR$^{10}$R$^{11}$, or a 4-10-membered heterocycloalkyl group which is bound to the benzimidazole through a nitrogen atom, and which is optionally substituted by one or more substituents R$^{12}$;

R$^{10}$ and R$^{11}$ independently represent $C_{1-7}$ alkyl, $C_{3-7}$ cycloalkyl-$C_{0-4}$ alkyl- or $C_{4-7}$ heterocycloalkyl-$C_{0-4}$ alkyl-[which latter three groups are optionally substituted by one or more groups selected from fluoro, —OH, NH$_2$, —CN, $C_{1-3}$ alkyl, —NH($C_{1-3}$ alkyl), —N($C_{1-3}$ alkyl)$_2$, —O$C_{1-5}$ alkyl, —O$C_{3-6}$ cycloalkyl, —O$C_{4-6}$ heterocycloalkyl (which latter six groups are optionally substituted by one or more substituents selected from fluoro, —CF$_3$, —CHF$_2$, —CH$_2$F, —CH$_3$)], or aryl-$C_{0-4}$ alkyl-, heteroaryl-$C_{0-4}$ alkyl-[which latter two groups are optionally substituted by one or more substituents selected from halo, —OH, —CN, $C_{1-3}$ alkyl, $C_{3-5}$ cycloalkyl, $C_{1-3}$ alkyl-O—, $C_{3-5}$ cycloalkyl-O— (which latter four groups are optionally substituted by one or more fluorine atoms)];

each R$^{12}$ independently represents halo, —OH, —NH$_2$, =O, —CN, $C_{1-4}$ alkyl, $C_{3-5}$ cycloalkyl-$C_{0-2}$ alkyl-, $C_{4-5}$ heterocycloalkyl-$C_{0-2}$ alkyl-, $C_{1-4}$ alkyl-O—, $C_{1-3}$ alkyl-C(=O)—, —C(=O)—NH($C_{1-3}$ alkyl), —C(=O)—N($C_{1-3}$ alkyl)$_2$ [which latter six groups are optionally substituted by one or more groups selected from: fluoro, —OH, oxo, —NH$_2$, —CN, $C_{1-3}$ alkyl, —NH($C_{1-3}$ alkyl), —N($C_{1-3}$ alkyl)$_2$, —O$C_{1-3}$ alkyl, —O$C_{3-5}$ cycloalkyl [which latter five groups are optionally substituted by one or more substituents selected from fluoro, —CF$_3$, —CHF$_2$, —CH$_2$F], or aryl-$C_{0-4}$ alkyl-, heteroaryl-$C_{0-4}$ alkyl-[which latter two groups are optionally substituted by one or more substituents selected from halo, —OH, —CN, $C_{1-3}$ alkyl, $C_{3-5}$ cycloalkyl, $C_{1-3}$ alkyl-O—, $C_{3-5}$ cycloalkyl-O— (which latter four groups are optionally substituted by one or more fluorine atoms)];

A represents $C_{1-8}$ alkyl, $C_{3-8}$ alkynyl, aryl-$C_{0-3}$alkyl-, $C_{3-8}$ cycloalkyl-$C_{0-3}$alkyl-, 4-7 membered heterocycloalkyl-$C_{0-3}$ alkyl-, heteroaryl-$C_{0-3}$alkyl-in which latter six groups the alkyl-, alkynyl-, cycloalkyl- and heterocycloalkyl-fragments are optionally substituted by one or more substituents selected from R$^{14}$ and the aryl and heteroaryl fragments are optionally substituted by one or more substituents selected from R$^{15}$;

each R$^{14}$ independently represents fluoro, —OH, —CN, =O, —NH$_2$, —NH($C_{1-3}$ alkyl), —N($C_{1-3}$ alkyl)$_2$, —O$C_{1-6}$ alkyl, $C_{1-6}$alkyl (in which latter four groups the alkyl fragments are optionally substituted by one or more substituents selected from fluoro, —CN, =O, —NH$_2$, —NH($C_{1-3}$ alkyl), N($C_{1-3}$ alkyl)$_2$, —OH, —O$C_{1-3}$ alkyl) or aryl, heteroaryl [which latter two groups are optionally substituted by one or more substituents selected from halo, OH, —CN, $C_{1-3}$ alkyl, O$C_{1-3}$ alkyl (which latter two alkyl groups are optionally substituted by one or more fluorine atoms)];

each R$^{15}$ independently represents halo, —OH, —CN, —NH$_2$, —NH($C_{1-3}$ alkyl), —N($C_{1-3}$ alkyl)$_2$, —O$C_{1-3}$ alkyl, aryl, heteroaryl [which latter two groups are optionally substituted by one or more substituents selected from halo, OH, —CN, $C_{1-3}$ alkyl, O$C_{1-3}$ alkyl (which latter two alkyl groups are optionally substituted by one or more fluorine atoms)], $C_{1-7}$ alkyl, $C_{2-7}$ alkynyl, $C_{3-7}$ cycloalkyl, 4-7 membered heterocycloalkyl (which latter alkyl, alkynyl, heterocycloalkyl or cycloalkyl groups are optionally substituted by one or more substituents selected from fluoro, —CN, =O, —NH$_2$, —NH($C_{1-3}$ alkyl), N($C_{1-3}$ alkyl)$_2$, —OH, O$C_{1-3}$alkyl);

or a salt thereof, particularly a physiologically acceptable salt thereof.

In a second embodiment, in the general formula I, A, L, M, W, $R^2$, $R^3$, $R^4$, $_R^6$, $R^7$, $R^a$, $R^b$ have the same meaning as defined in any of the preceding embodiments, and $R^1$ represents halo, $C_{1-3}$ alkyl optionally substituted by one or more fluorine atoms.

In another embodiment, in the general formula I, A, L, M, W, $R^1$, $R^6$, $R^a$, $R^b$ have the same meaning as defined in any of the preceding embodiments, and $R^2$, $R^3$, $R^4$, $R^7$ independently represent hydrogen, fluoro, chloro.

In another embodiment, in the general formula I, A, L, M, W, $R^1$, $R^2$, $R^3$, $R^4$, $R^6$, $R^7$ have the same meaning as defined in any of the preceding embodiments, and $R^a$ and $R^b$ represent hydrogen.

In another embodiment, in the general formula I, A, L, M, $R^1$, $R^2$, $R^3$, $R^4$, $R^6$, $R^7$, $R^a$, $R^b$ have the same meaning as defined in any of the preceding embodiments, and W represents —C(O)—, —C(O)O— which groups are bound to the nitrogen of the —NH— moiety via the carbon atom.

In another embodiment, in the general formula I, A, L, W, $R^1$, $R^2$, $R^3$, $R^4$, $R^6$, $R^7$, $R^a$, $R^b$ have the same meaning as defined in any of the preceding embodiments, and
M represents $C_{1-6}$ alkyl, $C_{3-8}$ cycloalkyl-$C_{0-1}$ alkyl-[which latter two groups are optionally substituted by one or more groups selected from fluoro, $C_{1-3}$ alkyl optionally substituted by one or more fluorine atoms].

In another embodiment, in the general formula I, A, L, M, W, $R^1$, $R^2$, $R^3$, $R^4$, $R^7$, $R^9$, $R^a$, $R^b$ have the same meaning as defined in any of the preceding embodiments, and
$R^6$ represents hydrogen, $C_{1-5}$ alkyl, $C_{3-5}$cycloalkyl-$C_{0-1}$ alkyl (which latter two groups are optionally substituted by one or more substituents selected from fluoro, =O, —$NH_2$, —$NH(C_{1-3}$ alkyl) or —$N(C_{1-3}$ alkyl)$_2$).

In another embodiment, in the general formula I, A, L, M, W, $R^1$, $R^2$, $R^3$, $R^4$, $R^7$, $R^9$, $R^a$, $R^b$ have the same meaning as defined in any of the preceding embodiments, and
$R^6$ represents hydrogen or $C_{1-5}$ alkyl optionally substituted by one or more fluorine atoms.

In another embodiment, in the general formula I, L, M, W, $R^1$, $R^2$, $R^3$, $R^4$, $R^6$, $R^7$, $R^a$, $R^b$ have the same meaning as defined in any of the preceding embodiments, and
A represents $C_{1-6}$ alkyl, $C_{3-8}$ cycloalkyl-$C_{0-3}$alkyl-, aryl-$C_{0-3}$ alkyl-, heteroaryl-$C_{0-3}$alkyl-in which latter four groups the alkyl- and cycloalkyl-fragments are optionally substituted by one or more substituents selected from $R^{14}$ and the aryl and heteroaryl fragments are optionally substituted by one or more substituents selected from $R^{15}$;
each $R^{14}$ independently represents fluoro, $C_{1-3}$alkyl optionally substituted by one or more fluorine atoms or phenyl optionally substituted by one or more fluorine atoms;
each $R^{15}$ independently represents halo, —$OC_{1-3}$ alkyl, $C_{1-3}$ alkyl, (which latter two alkyl groups are optionally substituted by one or more substituents fluorine atoms).

In another embodiment, in the general formula I, L, M, W, $R^1$, $R^2$, $R^3$, $R^4$, $R^6$, $R^7$, $R^a$, $R^b$ have the same meaning as defined in any of the preceding embodiments, and
A represents $C_{1-6}$ alkyl, $C_{3-8}$cycloalkyl-$C_{0-3}$alkyl-in which groups the alkyl- or cycloalkyl-fragments are optionally substituted by one or more substituents selected from $R^{14}$;
each $R^{14}$ independently represents fluoro, $C_{1-3}$alkyl optionally substituted by one or more fluorine atoms.

In another embodiment, in the general formula I, A, M, W, $R^1$, $R^2$, $R^3$, $R^4$, $R^6$, $R^7$, $R^a$, $R^b$ have the same meaning as defined in any of the preceding embodiments, and
L represents —$NH_2$, —$NHR^{10}$, —$NR^{10}R^{11}$, or
azetidinyl-, pyrrolidinyl-, piperidinyl-, morpholinyl or

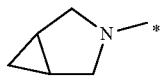

all of which heterocyclic groups are optionally substituted by one or more substituents $R^{12}$, while the above mentioned groups are bonded to the benzimidazole core through a nitrogen atom;
each $R^{10}$ and $R^{11}$ independently represent $C_{1-5}$ alkyl or $C_{3-6}$ cycloalkyl-$C_{0-1}$ alkyl-, $C_{4-6}$ heterocycloalkyl-$C_{0-1}$ alkyl-[which latter three groups are optionally substituted by one or more groups selected from fluoro, —OH, —$OC_{1-3}$ alkyl, $C_{1-3}$ alkyl (which latter two groups are optionally substituted by one or more fluorine atoms)], or
aryl-$C_{0-1}$ alkyl-, heteroaryl-$C_{0-1}$ alkyl-[which latter two groups are optionally substituted by one or more substituents selected from halo, —OH, —CN, $C_{1-3}$ alkyl, $C_{1-3}$ alkyl-O— (which latter two groups are optionally substituted by one or more fluorine atoms)];
each $R^{12}$ independently represents fluoro, $C_{1-4}$ alkyl optionally substituted by one or more fluorine atoms, or
phenyl optionally substituted by one or more substituents selected from halo, $C_{1-3}$ alkyl which is optionally substituted by one or more fluorine atoms.

In another embodiment, in the general formula I, A, M, W, $R^1$, $R^2$, $R^3$, $R^4$, $R^6$, $R^7$, $R^a$, $R^b$ have the same meaning as defined in any of the preceding embodiments, and
L represents —$NH_2$, —$NHR^{10}$, —$NR^{10}R^{11}$, or
azetidinyl-, pyrrolidinyl-, piperidinyl- or

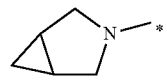

all of which heterocyclic groups are optionally substituted by one or more substituents $R^{12}$, while the above mentioned groups are bonded to the benzimidazole core through a nitrogen atom;
each $R^{10}$ and $R^{11}$ independently represent $C_{1-5}$ alkyl, $C_{3-6}$ cycloalkyl-$C_{0-1}$ alkyl-[which latter two groups are optionally substituted by one or more groups selected from fluoro, —OH, —$OC_{1-3}$ alkyl, $C_{1-3}$ alkyl (which latter two groups are optionally substituted by one or more fluorine atoms)], or
aryl-$C_{0-1}$ alkyl-optionally substituted by one or more substituents selected from halo, —OH, —CN, $C_{1-3}$ alkyl, $C_{1-3}$ alkyl-O— [which latter two groups are optionally substituted by one or more fluorine atoms];
each $R^{12}$ independently represents fluoro, $C_{1-4}$ alkyl optionally substituted by one or more fluorine atoms, or
phenyl optionally substituted by one or more substituents selected from halo, $C_{1-3}$ alkyl which is optionally substituted by one or more fluorine atoms.

A further embodiment of the present invention comprises compounds of formula Ia

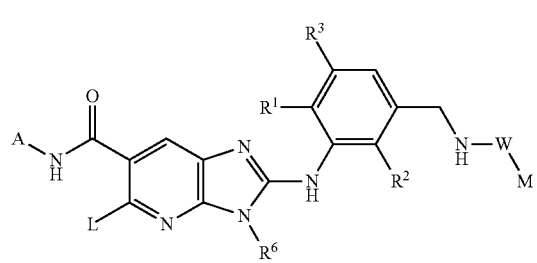

in which
$R^1$ represents halo, $C_{1-3}$ alkyl optionally substituted by one or more fluorine atoms;
$R^2$ and $R^3$ independently represent hydrogen, fluoro, chloro;
$R^6$ represents hydrogen, $C_{1-5}$ alkyl, $C_{3-5}$cycloalkyl-$C_{0-1}$ alkyl (which latter two groups are optionally substituted by one or more substituents selected from fluoro, =O, —$NH_2$, —$NH(C_{1-3}$ alkyl) or —$N(C_{1-3}$ alkyl)$_2$);
W represents —C(O)—, —C(O)O— which groups are bound to the nitrogen of the —NH— moiety via the carbon atom;
M represents $C_{1-6}$ alkyl, $C_{3-8}$ cycloalkyl-$C_{0-1}$ alkyl-[which latter two groups are optionally substituted by one or more groups selected from fluoro, $C_{1-3}$ alkyl optionally substituted by one or more fluorine atoms];

A represents $C_{1-6}$ alkyl, $C_{3-8}$ cycloalkyl-$C_{0-1}$ alkyl-, aryl-$C_{0-3}$ alkyl-, heteroaryl-$C_{0-3}$alkyl-in which latter four groups the alkyl-and cycloalkyl-fragments are optionally substituted by one or more substituents selected from $R^{14}$ and the aryl and heteroaryl fragments are optionally substituted by one or more substituents selected from $R^{15}$;

each $R^{14}$ independently represents fluoro, $C_{1-3}$alkyl optionally substituted by one or more fluorine atoms or phenyl optionally substituted by one or more fluorine atoms;

each $R^{15}$ independently represents halo, —$OC_{1-3}$ alkyl, $C_{1-3}$ alkyl (which latter two alkyl groups are optionally substituted by one or more substituents fluorine atoms);

L represents —$NH_2$, —$NHR^{10}$, —$NR^{10}R^{11}$, or azetidinyl-, pyrrolidinyl-, piperidinyl-, morpholinyl- or

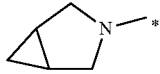

all of which heterocyclic groups are optionally substituted by one or more substituents $R^{12}$, while the above mentioned groups are bonded to the benzimidazole core through a nitrogen atom;

each $R^{10}$ and $R^{11}$ independently represent $C_{1-5}$ alkyl, $C_{3-6}$ cycloalkyl-$C_{0-1}$ alkyl-, $C_{4-6}$ heterocycloalkyl-$C_{0-1}$ alkyl- [which latter three groups are optionally substituted by one or more groups selected from fluoro, —OH, —$OC_{1-3}$ alkyl or $C_{1-3}$ alkyl (which latter two groups are optionally substituted by one or more fluorine atoms)], or aryl-$C_{0-1}$ alkyl-, heteroaryl-$C_{0-1}$ alkyl-[which latter two groups are optionally substituted by one or more substituents selected from halo, —OH, —CN, $C_{1-3}$ alkyl or $C_{1-3}$ alkyl-O— (which latter two groups are optionally substituted by one or more fluorine atoms)];

each $R^{12}$ independently represents fluoro, $C_{1-4}$ alkyl optionally substituted by one or more fluorine atoms, or phenyl optionally substituted by one or more substituents selected from halo, $C_{1-3}$ alkyl which is optionally substituted by one or more fluorine atoms;

or a salt thereof, particularly a physiologically acceptable salt thereof.

Alternatively, a further embodiment of the present invention comprises compounds of formula Ia, in which $R^1$ represents halo, $C_{1-3}$ alkyl optionally substituted by one or more fluorine atoms;

$R^2$ and $R^3$ independently represent hydrogen, fluoro, chloro;

$R^6$ represents hydrogen or $C_{1-5}$ alkyl which is optionally substituted by one or more fluorine atoms;

W represents —C(O)—, —C(O)O— which groups are bound to the nitrogen of the —NH— moiety via the carbon atom;

M represents $C_{1-6}$ alkyl, $C_{3-8}$ cycloalkyl-$C_{0-1}$ alkyl-[which latter two groups are optionally substituted by one or more groups selected from fluoro, $C_{1-3}$ alkyl optionally substituted by one or more fluorine atoms];

A represents $C_{1-6}$ alkyl, $C_{3-8}$cycloalkyl-$C_{0-3}$alkyl-in which groups the alkyl- or cycloalkyl-fragments are optionally substituted by one or more substituents selected from $R^{14}$;

each $R^{14}$ independently represents fluoro, $C_{1-3}$alkyl optionally substituted by one or more fluorine atoms;

L represents —$NH_2$, —$NHR^{10}$, —$NR^{10}R^{11}$, or azetidinyl-, pyrrolidinyl-, piperidinyl- or

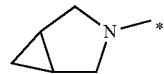

all of which heterocyclic groups are optionally substituted by one or more substituents $R^{12}$, while the above mentioned groups are bonded to the benzimidazole core through a nitrogen atom;

each $R^{10}$ and $R^{11}$ independently represent $C_{1-5}$ alkyl or $C_{3-6}$ cycloalkyl-$C_{0-1}$ alkyl-[which latter two groups are optionally substituted by one or more groups selected from fluoro, —OH, —$OC_{1-3}$ alkyl, $C_{1-3}$ alkyl (which latter two groups are optionally substituted by one or more fluorine atoms)], or aryl-$C_{0-1}$ alkyl-optionally substituted by one or more substituents selected from halo, —OH, —CN, $C_{1-3}$ alkyl, $C_{1-3}$ alkyl-O— [which latter two groups are optionally substituted by one or more fluorine atoms];

each $R^{12}$ independently represents fluoro, $C_{1-4}$ alkyl optionally substituted by one or more fluorine atoms, or phenyl optionally substituted by one or more substituents selected from halo, $C_{1-3}$ alkyl which is optionally substituted by one or more fluorine atoms.

In another embodiment, in the general formula Ia, L, M, W, $R^1$, $R^2$, $R^3$, $R^6$ have the same meaning as defined in any of the preceding embodiments, and A represents $C_{1-5}$ alkyl, phenyl-$C_{0-2}$alkyl-, $C_{3-6}$ cycloalkyl-$C_{0-1}$ alkyl-, pyridinyl-$C_{0-1}$alkyl-, thienyl-$C_{0-1}$alkyl- in which latter five groups the alkyl- and cycloalkyl-fragments are optionally substituted by one or more substituents selected from $R^{14}$ and the phenyl, pyridinyl and thienyl fragments are optionally substituted by one or more substituents selected from $R^{15}$;

each $R^{14}$ independently represents fluoro, $CH_3$, $CH_2F$, $CHF_2$, $CF_3$ or phenyl optionally substituted by one or more fluorine atoms;

each $R^{15}$ independently represents fluoro, chloro, $CH_3$, $CH_2F$, $CHF_2$, $CF_3$ or —$OCH_3$, —$OCH_2F$, —$OCHF_2$, —$OCF_3$.

In another embodiment, in the general formula Ia, L, M, W, $R^1$, $R^2$, $R^3$, $R^6$ have the same meaning as defined in any of the preceding embodiments, and A represents $C_{1-6}$ alkyl, $C_{3-6}$cycloalkyl- in which groups the alkyl- or cycloalkyl-fragments are optionally substituted by one or more substituents selected from $R^{14}$;

each $R^{14}$ independently represents fluoro, $CH_3$, $CH_2F$, $CHF_2$, $CF_3$.

In another embodiment, in the general formula Ia, A, L, W, $R^1$, $R^2$, $R^3$, $R^6$ have the same meaning as defined in any of the preceding embodiments, and M represents $C_{1-6}$ alkyl, $C_{3-6}$ cycloalkyl- [which latter two groups are optionally substituted by one or more groups selected from fluoro, $CH_3$, $CH_2F$, $CHF_2$, $CF_3$].

In another embodiment, in the general formula Ia, A, M, W, $R^1$, $R^2$, $R^6$ have the same meaning as defined in any of the preceding embodiments, and L represents $-NH_2$, $-NHR^{10}$, $-NR^{10}R^{11}$, or
azetidinyl-, pyrrolidinyl-, piperidinyl-, morpholinyl or

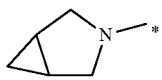

all of which heterocyclic groups are optionally substituted by one or more substituents $R^{12}$, while the above mentioned groups are bonded to the benzimidazole core through a nitrogen atom;

each $R^{10}$ and $R^{11}$ independently represent $C_{1-5}$-alkyl, $C_{3-6}$-cycloalkyl-$C_{0-1}$ alkyl- or oxetanyl-$C_{0-1}$ alkyl- [which latter three groups are optionally substituted by one or more groups selected from fluoro, $-OH$, $-OCH_3$, $-OCH_2F$, $-OCHF_2$, $-OCF_3$ or $CH_3$, $CH_2F$, $CHF_2$, $CF_3$], or imidazolyl-$C_{0-1}$ alkyl- or 1,2,4-triazolyl-$C_{0-1}$ alkyl- [which latter two groups are optionally substituted by one or more substituents selected from $CH_3$, $CH_2F$, $CHF_2$, $CF_3$];

each $R^{12}$ independently represents fluoro, $CH_3$, $CH_2F$, $CHF_2$, $CF_3$.

In another embodiment, in the general formula Ia, A, M, W, $R^1$, $R^2$, $R^6$ have the same meaning as defined in any of the preceding embodiments, and L represents $-NH_2$, $-NHR^{10}$, $-NR^{10}R^{11}$, or
azetidinyl-, pyrrolidinyl-, piperidinyl-, or

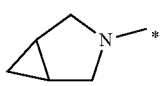

all of which heterocyclic groups are optionally substituted by one or more substituents $R^{12}$, while the above mentioned groups are bonded to the benzimidazole core through a nitrogen atom;

each $R^{10}$ and $R^{11}$ independently represent $C_{1-5}$ alkyl or $C_{3-6}$ cycloalkyl-$C_{0-1}$ alkyl- [which latter two groups are optionally substituted by one or more groups selected from fluoro, $-OH$, $-OCH_3$, $-OCH_2F$, $-OCHF_2$, $-OCF_3$, $CH_3$, $CH_2F$, $CHF_2$, $CF_3$], each $R^{12}$ independently represents fluoro, $CH_3$, $CH_2F$, $CHF_2$, $CF_3$.

A further embodiment of the present invention comprises compounds of formula Ib

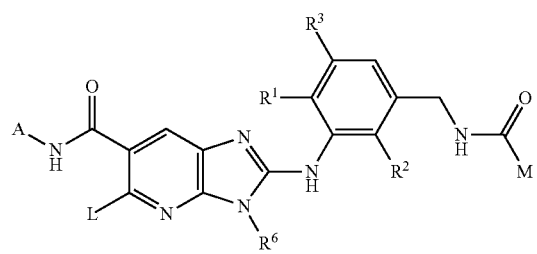

Ib in which $R^1$ represents fluoro, chloro;

$R^2$ represents hydrogen, fluoro, chloro;

$R^3$ represents hydrogen or fluoro;

$R^6$ represents hydrogen, $CH_3$;

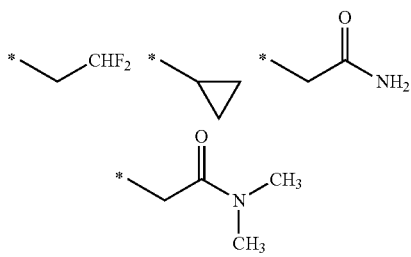

M represents a group selected from

A represents a group selected from

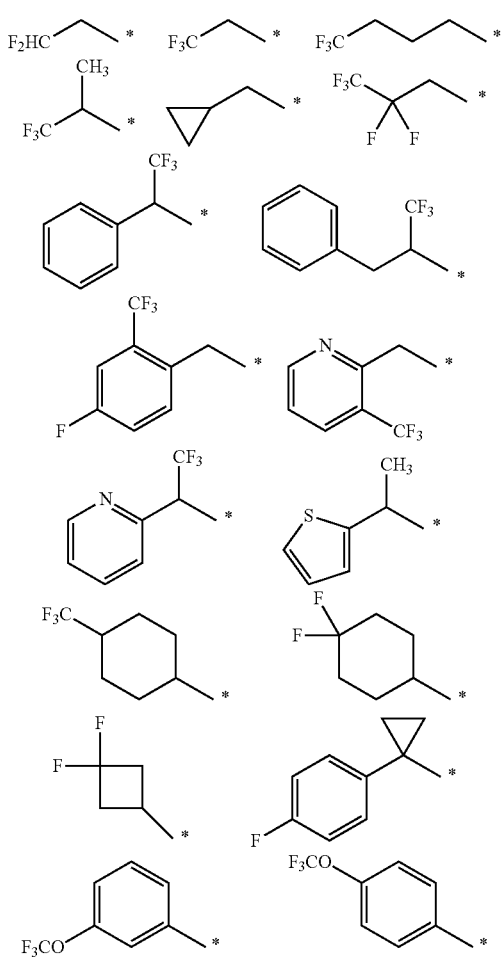

-continued

L represents a group selected from

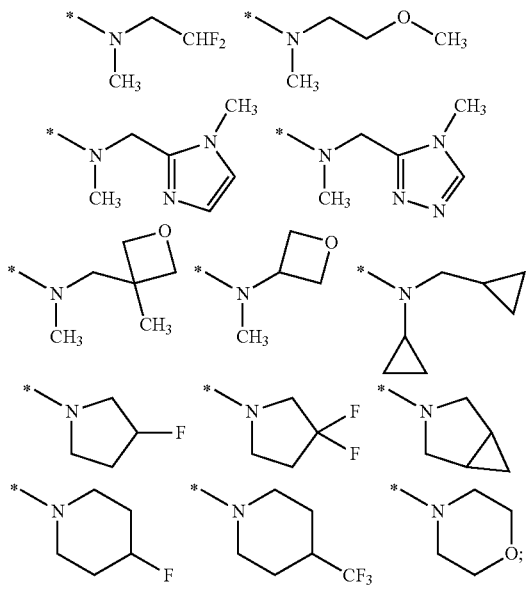

or a salt thereof, particularly a physiologically acceptable salt thereof.

Alternatively, a further embodiment of the present invention comprises compounds of formula Ib in which $R^1$ represents fluoro, chloro;
$R^2$ represents hydrogen, fluoro, chloro;
$R^3$ represents hydrogen or fluoro;
$R^6$ represents hydrogen, $CH_3$;
M represents a group selected from

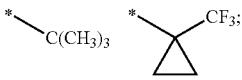

A represents a group selected from

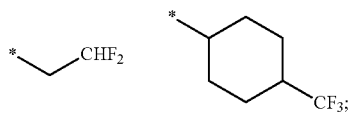

L represents a group selected from

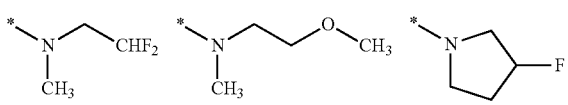

-continued

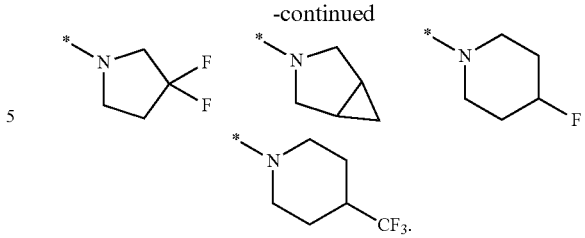

In another embodiment, in the general formulae I, Ia or Ib, A, L, M, W, $R^1$, $R^3$, $R^4$, $R^6$, $R^7$, $R^a$, $R^b$ have the same meaning as defined in any of the preceding embodiments, and
$R^2$ independently represent fluoro, chloro.

TERMS AND DEFINITIONS USED

General Definitions:

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named sub-group is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined, for example a cyclopropylmethyl- group would be represented by the following drawing:

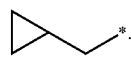

Tautomers/Stereochemistry/Solvates/Hydrates:

Unless specifically indicated, throughout the specification and the appended claims, a given chemical formula or name shall encompass tautomers (e.g. 1H-benzimidazole may be considered to be identical to a corresponding compound containing a 3H-benzimidazole) and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycerophosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Halogen:
The term halogen generally denotes fluorine, chlorine, bromine and iodine.

Alkyl:
The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

Alkynyl:
The term "$C_{2-n}$-alkynyl", wherein n is an integer from 3 to n, is used for a group as defined in the definition for "$C_{1-n}$-alkyl" with at least two carbon atoms, if at least two of those carbon atoms of said group are bonded to each other by a triple bond.

Cycloalkyl:
The term "$C_{3-n}$-cycloalkyl", wherein n is an integer >3, either alone or in combination with another radical denotes a mono-, bi-, tri- or tetracyclic, saturated, hydrocarbon radical with 3 to n C atoms. For example the term $C_{3-7}$-cycloalkyl includes cyclopropyl, cyclobutyl, cyclopentyl, cyclohexyl and cycloheptyl.

The term "cycloalkyl" encompasses fused, bridged and spirocyclic systems. The cycloalkyl radical may further be fused to a phenyl ring or to a 5-6-membered heteroaryl ring, e.g a thienyl-, pyrrolyl-, thiazolyl-, oxazolyl-, isoxazolyl-, pyrazolyl-, triazolyl-, tetrazolyl-, pyridinyl-, pyrimidinyl-pyrazinyl- or pyridazinyl-ring.

Furthermore, the term "cycloalkyl" includes the following exemplary structures, which are not depicted as radicals as they may be attached through a covalent bond to any atom of the cycloalkyl ring fragment but not to an atom of the aryl or heteroaryl fragment:

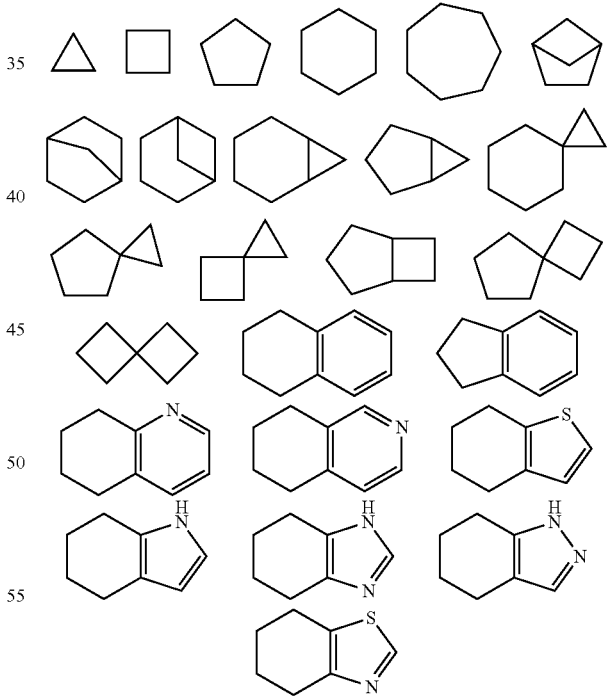

Heterocycloalkyl:
The term "4-n-membered heterocycloalkyl", wherein n is an integer >4, means a saturated or partially unsaturated mono- or polycyclic ring system containing one or more heteroatoms selected from N, O or S(O)$_r$, wherein r=0, 1 or 2, consisting of 4 to n ring atoms. The hetero-cycloalkyl ring system may further be fused to a phenyl- or 5-6-membered heteroaryl ring such as a thienyl-, pyrrolyl-, thiazolyl-, oxazolyl-, isoxazolyl-, imidazolyl-, pyrazolyl-, triazolyl-, tetrazolyl-, pyridinyl-, pyrimidinyl- pyrazinyl- or pyridazinyl- ring. The term "heterocycloalkyl" is intended to include all the possible isomeric forms.

The term "heterocycloalkyl" includes the following exemplary structures, which are not depicted as radicals as they may be attached through a covalent bond to any atom of the heterocycloalkyl or cycloalkyl ring fragment but not to an atom of the aryl or heteroaryl fragment:

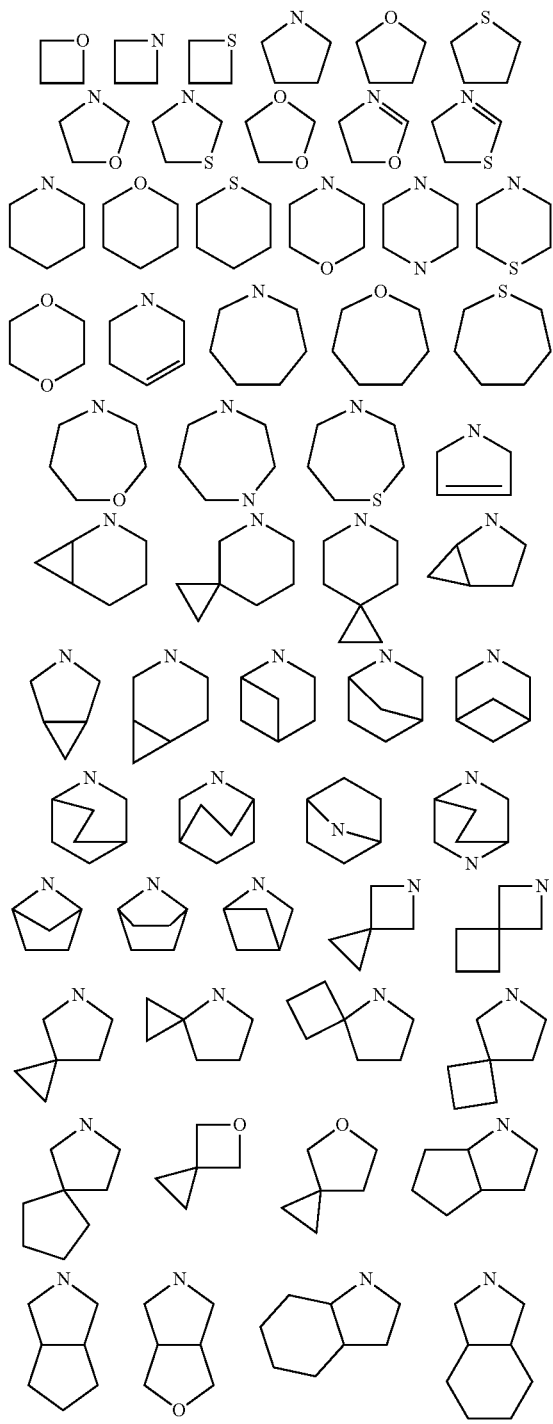

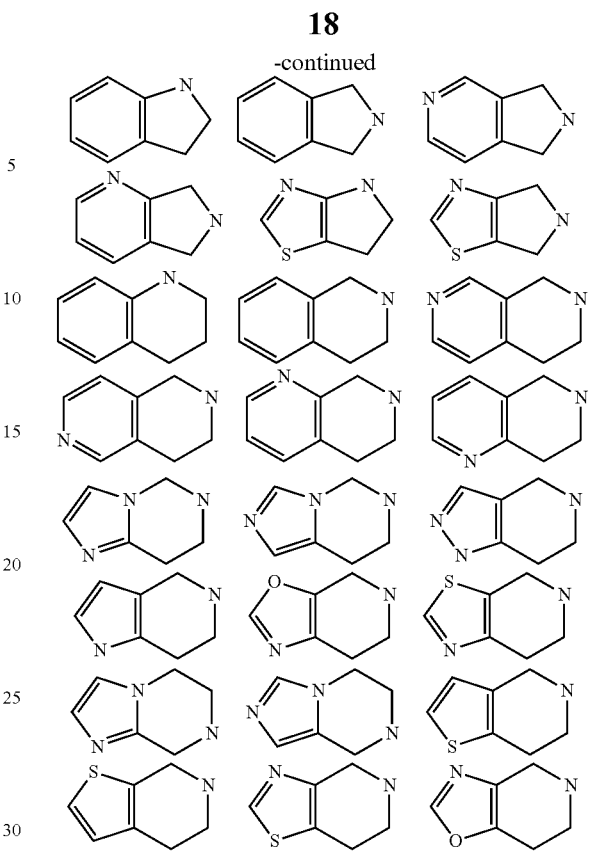

Aryl:
The term "aryl" as used herein, either alone or in combination with another radical, denotes a carbocyclic aromatic monocyclic group containing 6 carbon atoms which may further be fused to a second 5- or 6-membered aromatic, saturated or unsaturated carbocyclic group.

The term "aryl" includes phenyl, indanyl, indenyl, naphthyl, anthracenyl, phenanthrenyl, tetrahydronaphthyl and dihydronaphthyl which may be attached through a covalent bond to any atom of the aromatic fragment.

Heteroaryl:
The term "heteroaryl" means a mono- or polycyclic ring system containing one or more hetero-atoms selected from N, O or S(O)$_r$, wherein r=0, 1 or 2, consisting of 5 to 14 ring atoms wherein at least one of the heteroatoms is part of the aromatic ring which may further be fused to a second 5- or 7-membered aromatic, saturated or unsaturated cycloalkyl or heterocycloalkyl group. The term "heteroaryl" is intended to include all the possible isomeric forms.

The term "heteroaryl" includes the following exemplary structures, which are not depicted as radicals as they may be attached through a covalent bond to any atom of the heteroaryl ring but not to an atom of the cycloalkyl or heterocycloalkyl fragment:

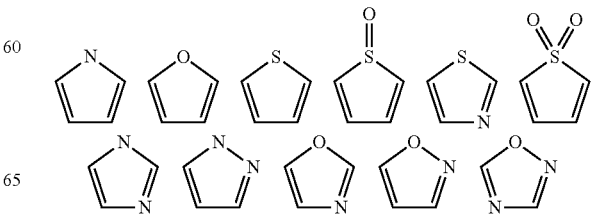

-continued

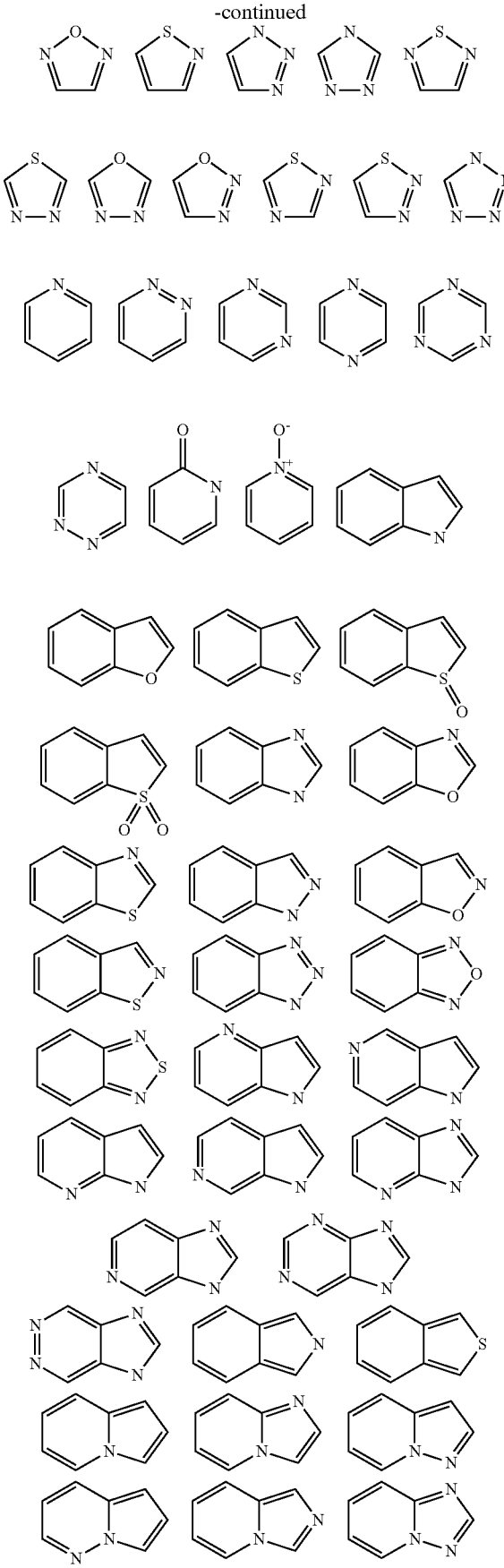

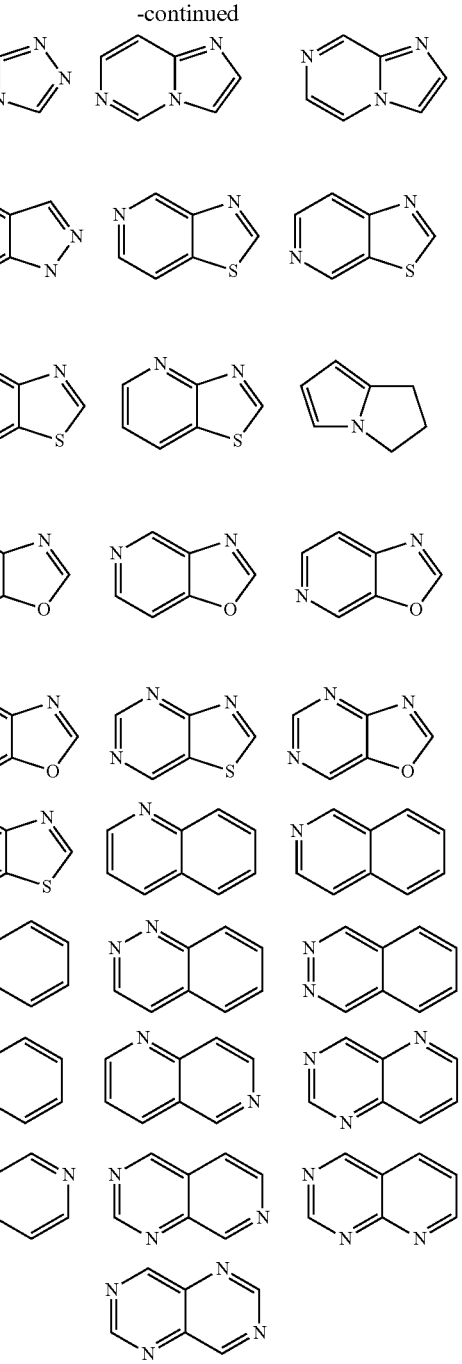

METHODS OF PREPARATION

Compounds of the present invention can be prepared in accordance with techniques that are well known to those skilled in the art, for example as described hereinafter and in the experimental section or in analogy to methods described in WO2010/034796, WO2010/034797 and WO2010/100249. According to a further aspect of the invention there is provided a process for the preparation of a compound of formula I, which process can be performed for example according to the following schemes A-C.

Scheme A (all variable groups are as defined in claim 1):
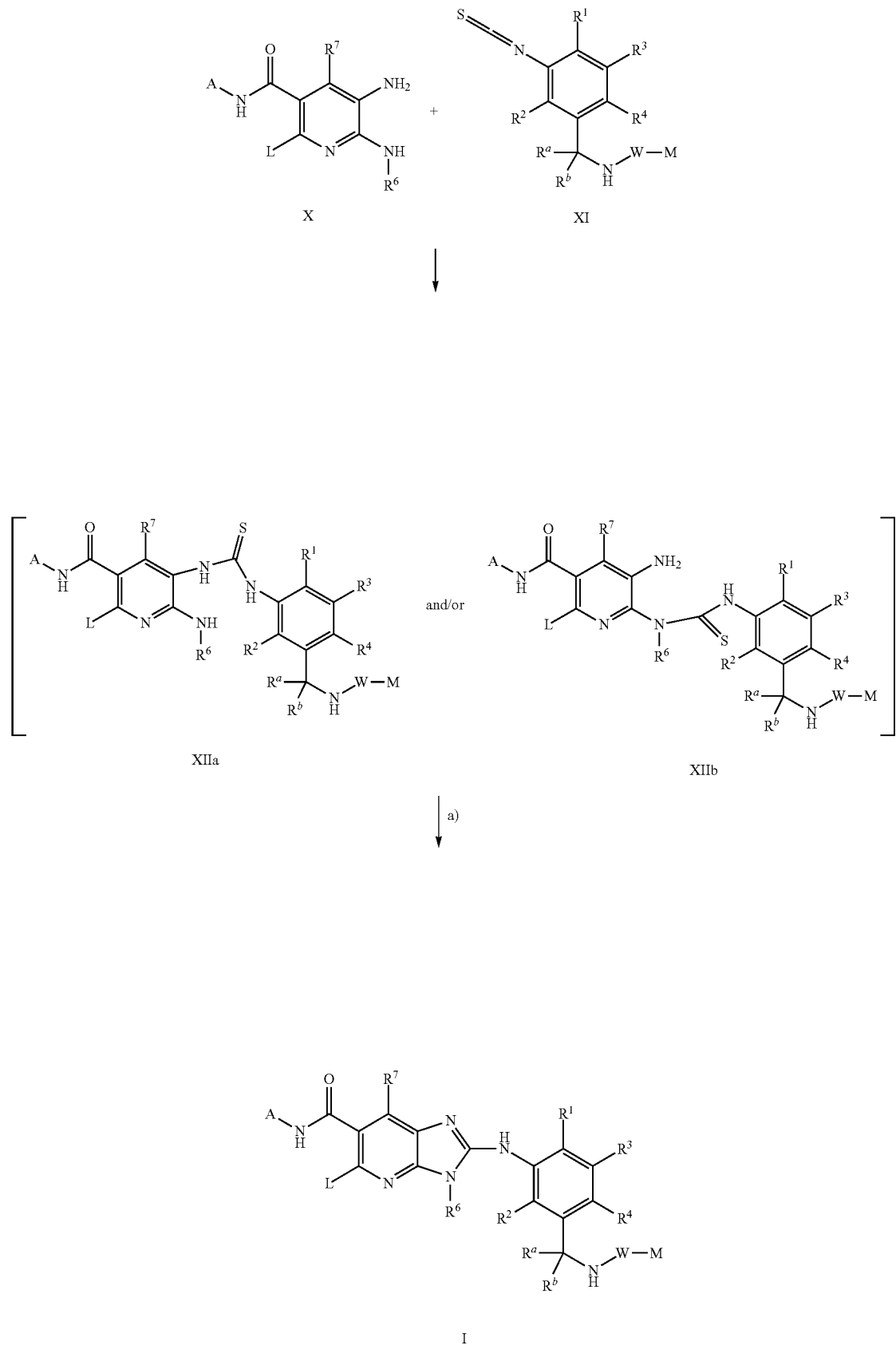

The reaction between phenylenediamine X and the thioisocyanate XI (Step a) can be performed under standard conditions known to those skilled in the art—for example in analogy to the process described in WO2010/034796 or WO2010/100249—in presence of a suitable solvent such as diethyl ether (Et$_2$O), dimethylformamide (DMF), dichloromethane (DCM), acetonitrile (MeCN) and/or tetrahydrofuran (THF). The reaction is preferably performed in the presence of a suitable reagent which enhances the cyclisation step as for instance CH$_3$—I or a carbodiimide based compound such as N,N'-dicyclohexylcarbodiimide (DCC), 1-ethyl-3-(3-dimethylaminopropyl) carbodiimide (EDCI, or its salt, e.g. hydrochloride) or N,N'-diisopropylcarbodiimide (DIC) or in presence of an amine base e.g. triethylamine (TEA) or diisopropyl ethyl amine (DIPEA). The reaction may proceed at any suitable temperature between 0° C. to 200° C., preferably between room temperature and 100° C. Step a can be performed in a step-wise reaction under isolation of the thiourea intermediates XIIa and/or XIIb or in a one-pot procedure.

Alternatively the compounds of formula I can be synthesized according to scheme B.

Scheme B (all variable groups are as defined in claim 1 and PG$^{acid}$ is a protecting group of a carboxylic acid function):

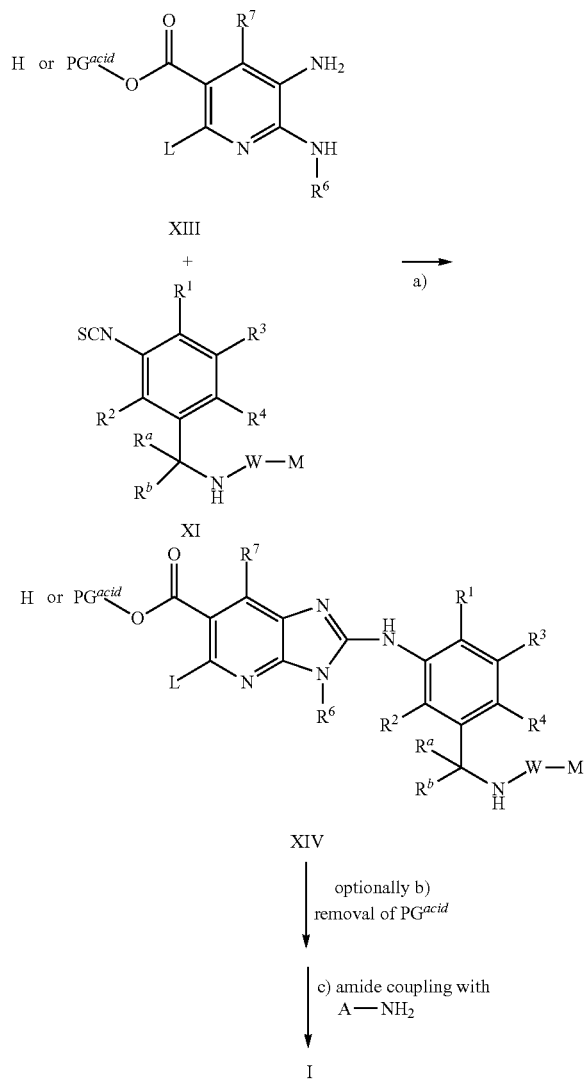

The protecting group PG$^{acid}$ is a literature known protecting group of a carboxylic acid, well known to those skilled in the art as for example described in "*Protective Groups in Organic Synthesis*", 3$^{rd}$ edition, T. W. Greene & P. G. M. Wutz, Wiley-Interscience (1999), for example a C$_{1-5}$-alkyl-, allyl- or a benzyl-group.

Step a) can be performed as described in scheme A, but may also be performed in the presence of an additive (such as 2,2,2-trifluoro-N,O-bis-(trimethylsilyl)-acetamide) when an unprotected carboxylic acid moiety is present in XIII.

Step b) can be performed under known saponification conditions, for example with aqueous LiOH, NaOH or KOH in ethanol (EtOH), methanol (MeOH), DMF, MeCN, THF or dioxane or with Pd/C in MeOH.

The amide formation in step c) can be performed with an additional in-situ activating agent like 1-propylphosphonic acid cyclic anhydride (PPA), O-(benzotriazol-1-yl)-N,N,N', N'-tetramethyl-uronium tetrafluoroborate (TBTU), O-(benzotriazol-1-yl)-N,N,N',N'-tetramethyl-uronium hexafluorophosphate (HBTU), O-(7-azabenzotriazol-1-yl)-N,N,N',N'-tetramethyluronium-hexafluorophosphate (HATU), DCC, EDCI, carbonyldiimidazole (CDI), carbonylditriazole (CDT), 1-chloro-2-methyl-propenyl-dimethylamine, oxalyl chloride or other activating agents of the state of the art.

The coupling reaction is preferably performed in the presence of a base such as NaOH, KOH, NaHCO$_3$, triethylamine (TEA), N-ethyldiisopropylamine (DIPEA), pyridine, N,N,-dimethylaminopyridine (DMAP) or other appropriate bases of the state of the art and for example described in Houben-Weyl, "Methods in Organic Synthesis", Vol. E22a, p 425ff. The coupling reactions are performed in an appropriate solvent for example DCM, dioxane, THF, MeCN, DMF, dimethylacetamide (DMA), N-methylpyrrolidone (NMP) or in mixtures of the above mentioned solvents at any suitable temperature between 0° C. to 100° C.

When PG$^{acid}$ is a methyl or ethyl group the conversion of XIV to I can also be carried out in a one-pot procedure for example with trimethylaluminium or triethylaluminium in hexane, dioxane, THF at 20-80° C.

Alternatively the compounds of formula I can be synthesized according to scheme C.

Scheme C (all variable groups are as defined in claim 1 and PG$^{amino}$ is a protecting group of the benzylic amino group):

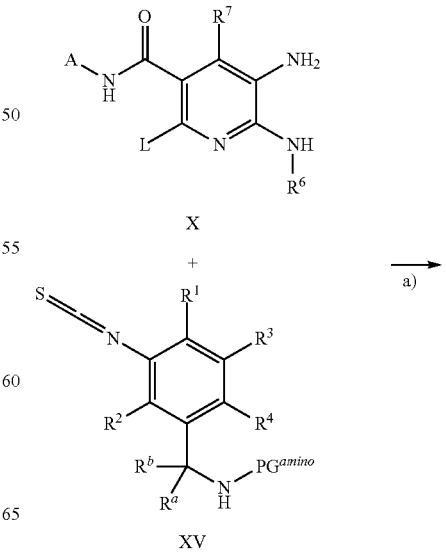

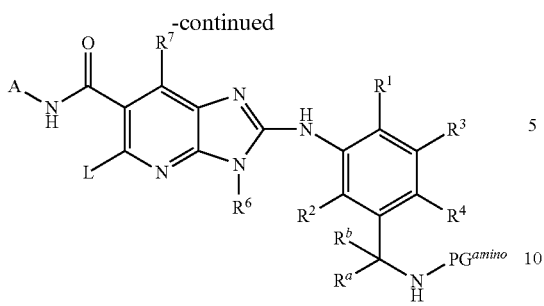

XVI

↓ d) removal of PG$^{amino}$

↓ e) amide coupling with HO—W—M or Cl—W—M

I

The protecting group PG$^{amino}$ in XV is a literature known protecting group of an amino group well known to those skilled in the art as for example described in "*Protective Groups in Organic Synthesis*", 3$^{rd}$ edition, T. W. Greene & P. G. M. Wutz, Wiley-Interscience (1999), for example a tert-butoxycarbonyl-, benzyloxycarbonyl-, ethoxycarbonyl-, methoxycarbonyl-, allyloxycarbonyl- or trifluormethylcarbonyl group.

Step a) can be performed as described in Scheme 1.

Step d) PG$^{amino}$ in XVI can be removed in accordance with techniques that are well known to those skilled in the art and which are exemplified hereinafter. For example XVI can be deprotected using an appropriate agent (depending on the protecting group) such as for example trifluoro acetic acid, HCl or H$_2$SO$_4$ solutions, KOH; Ba(OH)$_2$, Pd on carbon (Pd/C), trimethylsilyl iodide or other conditions as described in "*Protective Groups in Organic Synthesis*", 3$^{rd}$ edition, T. W. Greene & P. G. M. Wutz, Wiley-Interscience (1999). Appropriate co-solvent for this step is for example DCM, THF, MeCN, DMF, DMA, NMP or mixtures of the above mentioned solvents at any suitable temperature between 0° C. to 100° C. The amide formation in step e) can be performed with the acids HO—W-M and an additional in-situ activating agent like PPA, TBTU, HBTU, HATU, DCC, EDCI, CDI, CTI, 1-chloro-2-methyl-propenyl-dimethylamine, oxalyl chloride or other activating agents of the state of the art in analogy to Scheme B, step c; or directly with the corresponding acid chloride Cl—W-M under analogous conditions without an additional in situ activating agent.

The coupling reaction is preferably performed in the presence of a base such as NaOH, KOH, NaHCO$_3$, TEA, DIPEA, pyridine, DMAP or other appropriate bases of the state of the art and for example described in described in Houben-Weyl, "Methods in Organic Synthesis", Vol. E22a, p 425ff. The coupling reactions are performed in an appropriate solvent for example DCM, dioxane, THF, MeCN, DMF, DMA, NMP or in mixtures of the above mentioned solvents.

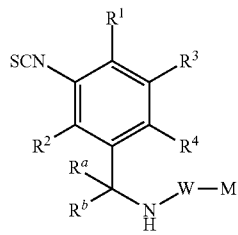

XI

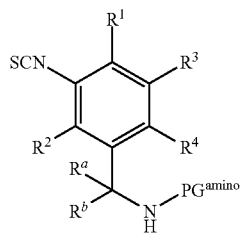

XV

The synthesis of the building blocks XI and XV—wherein all variable groups are as defined in claim 1 and PG$^{amino}$ is a protecting group of the benzylic amino group—is employing standard reaction conditions according to scheme D known to those skilled in the art which are examplified in the experimental part in detail or in WO2010/100249.

Scheme D (all variable groups are as defined in claim 1 and PG$^{amino}$ is a protecting group of the benzylic amino group):

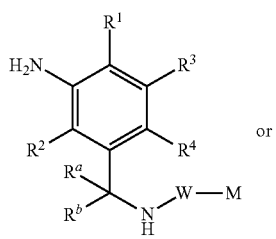

XVII

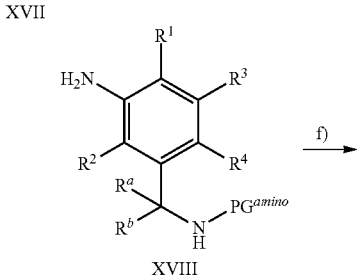

XVIII

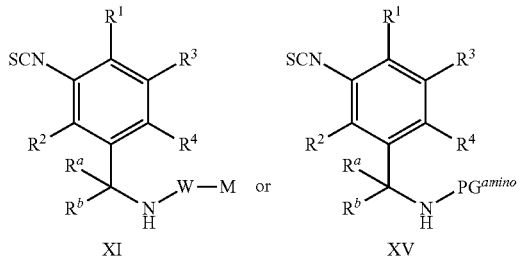

XI                    XV

Step f) can be performed according to standard literature procedures for example with reagents such as 1,1'-thiocarbonyldi-2-pyridone, O,O'-di-2-pyridylthiocarbonate, 1,1'-thiocarbonyldiimidazole or with thiophosgene in a solvent as for example DCM, dioxane or DMF at temperatures between 0-150° C. and optionally under addition of a base like DMAP or TEA.

The building blocks XVII and XVIII can be prepared according to scheme E:

Scheme E (all variable groups are as defined in claim 1 and PG$^{amino}$ is a protecting group of the benzylic amino group):

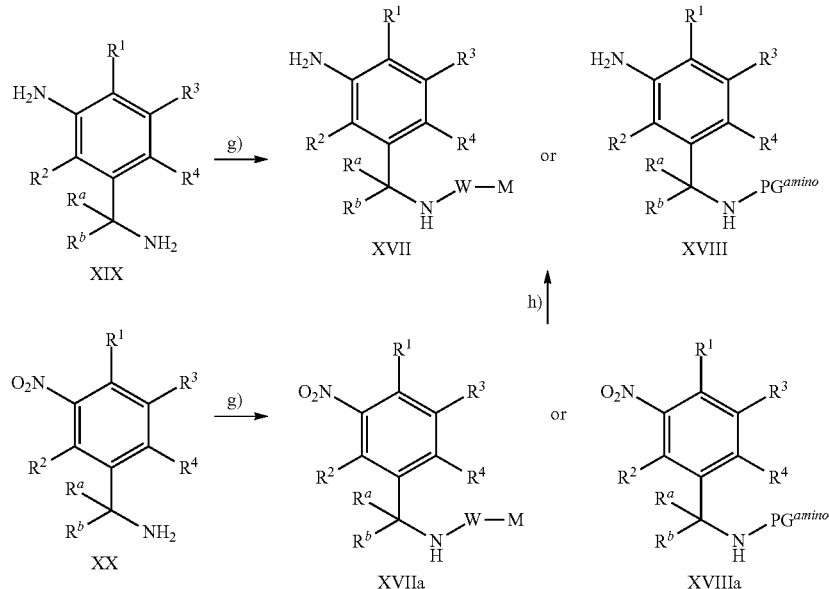

The amide formation in step g) can be performed in analogy to step c) or step e) to synthesize compound XVII or by using common reagents for amino group protection for example di-tert-butyl-dicarbonate, methyl-, ethyl-, benzyl or allyl-chloroformate under standard reaction conditions as described in "*Protective Groups in Organic Synthesis*", 3$^{rd}$ edition, T. W. Greene & P. G. M. Wutz, Wiley-Interscience (1999) to synthesize compounds XVIII.

The nitro group in precursor XVIIa or XVIIIa can be reduced to the amino group in step h) under literature known reduction conditions for example via hydrogenation (preferably at 1-5 bar) in presence of Pd/C, Pt/C or RaNi in MeOH, EtOH or THF optionally under acidic conditions in presence of HCl, or by using SnCl$_2$/HCl, Na$_2$S$_2$O$_4$, Zn/HCl, Fe/HCl, Fe-powder/aqueous NH$_4$Cl solution or according to procedures described in the literature for example R. Larock, *Comprehensive Organic Transformations*, VCH Verlagsgemeinschaft, Weinheim (1989). Appropriate solvent for this step is for example DCM, THF, MeCN, DMF, DMA, NMP, EtOH, MeOH or mixtures of the above mentioned solvents at any suitable temperature between 0° C. to 100° C.

The building blocks XIX and XX can be prepared according to scheme F-H:

Scheme F (R$^a$ and R$^b$ are hydrogen atoms, all other variable groups are as defined in claim 1):

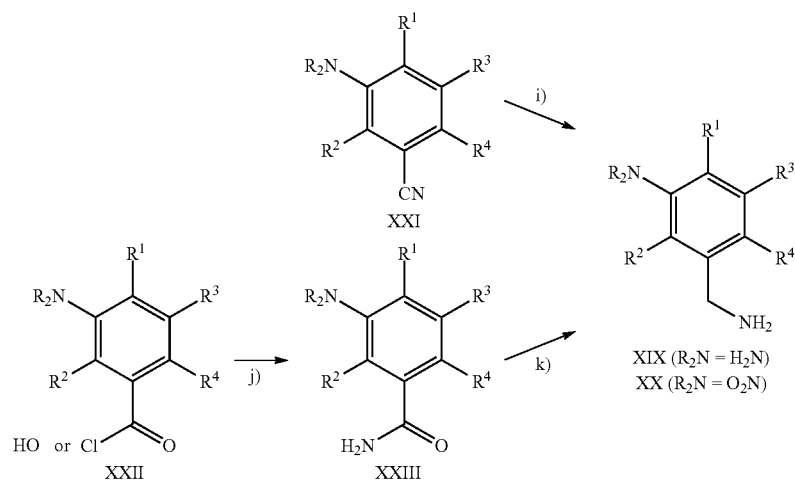

R$_2$N = H$_2$N or O$_2$N

Step i) can be performed via hydrogenation (1-5 bar) with a catalyst like Pd/C, PtO$_2$ or RaNi in a suitable solvent like MeOH or EtOH optionally using HCl or NH$_3$ as additive at temperatures between 0-60° C. or via reduction with LiAlH$_4$ or BH$_3$-containing reagents in a suitable solvent like THF, MeOH or EtOH under literature-known conditions.

Step j) can be performed under the amide coupling conditions described for step e) and using NH$_3$ as coupling partner, for example 1-chloro-2-methyl-propenyl-dimethylamine in THF can be used as activating agent.

Step k) can be performed using LiAlH$_4$ or BH$_3$-containing reagents under literature known conditions as for example compiled in R. C. Larock, Comprehensive Organic Transformations, VCH, 1989, p. 432-433, preferably with LiAlH$_4$ in THF at 0-80° C.

Alternatively compounds XIX and XX can be prepared as described in WO2010/100249 or according to scheme G

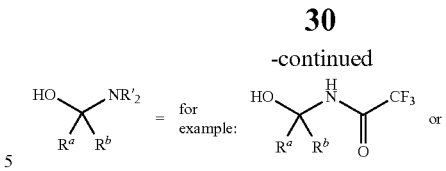

Scheme G (all variable groups are as defined in claim 1):

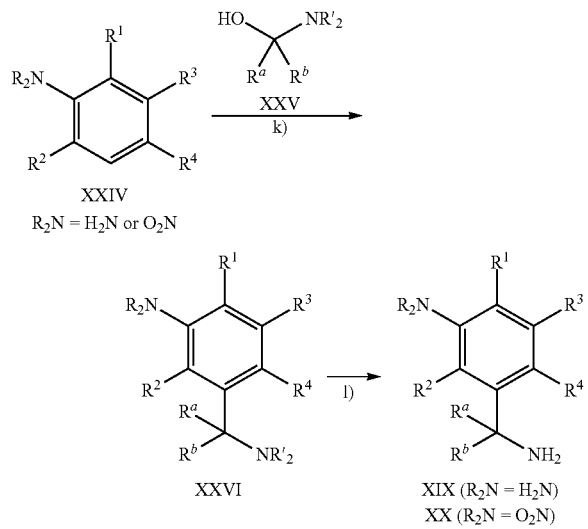

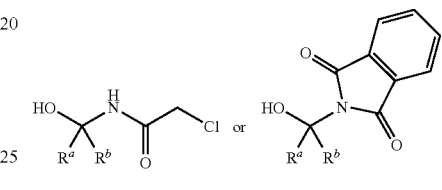

Step k) can be performed mixing XXIV with reagent XXV in concentrated H$_2$SO$_4$ or F$_3$C—SO$_3$H at temperatures between 0-150° C., preferably between 20-80° C.

Step l) can be performed using literature known deprotection procedures for the corresponding nitrogen protecting groups for example treatment of the phthalimide with hydrazine or cleavage of the amide bond using bases like NaOH in MeOH or EtOH at temperatures between 20-80° C. or under acidic conditions using aqueous HCl solution or HCl in dioxane at temperatures between 20-80° C.

Alternatively compounds XIX and XX can be prepared according to scheme H

Scheme H (R$^b$ = H, all variable groups are as defined in claim 1):

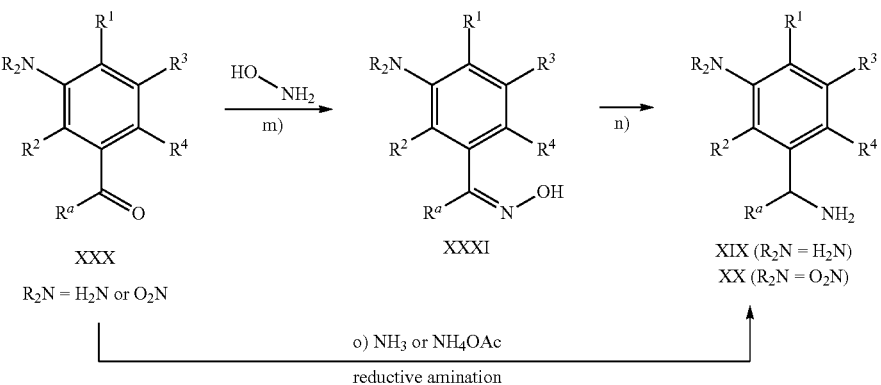

Step m) can be performed mixing XXX with HO—NH$_2$ in an appropriate solvent for example MeCN, DCM, THF, optionally using HCl as additive at temperatures between 0-60° C.

Step n) can be performed applying literature known reduction conditions for example via hydrogenation preferably at 1-5 bar H$_2$ pressure in presence of Pd/C or Ra—Ni in MeOH, EtOH or THF optionally using HCl or HOAc as catalyst, or by using SnCl$_2$/HCl, Zn/HCl, Fe/HCl, Fe-powder/aqueous NH$_4$Cl solution or according to procedures described in the literature for example R. Larock, *Comprehensive Organic Transformations*, VCH Verlagsgemeinschaft, Weinheim (1989).

Step o) can be performed applying literature known reduction conditions e.g. using ammonia or ammonium salts (e.g. ammonium acetate) and Borane reagents, for example NaBH$_3$CN, BH$_3$-THF-complex or BH$_3$—SMe$_2$-complex in water, MeOH, EtOH, THF or mixtures thereof, under buffered conditions preferably at a pH between 5-9 or employing hydrogenations using Pd/C or Ra—Ni as catalysts in MeOH, EtOH or THF optionally using HCl or HOAc as co-catalyst or according to procedures described in the literature for example in WO2010/100249 or R. Larock, *Comprehensive Organic Transformations*, VCH Verlagsgemeinschaft, Weinheim (1989).

The synthesis of building blocks X and XIII can be performed as described in the experimental part or in scheme I, wherein A, L, R$^6$, R$^7$ and R$^9$ have the meaning as defined in claim 1 and PG$^{acid}$ is a literature known carboxylic acid protecting group as described above and LG is a leaving group on the aromatic ring (for example a methoxy-, 2,2-difluoroethoxy, fluoro, chloro, bromo, iodo or trifluormethylsulfonyl group). The individual steps can also be performed in analogy to standard literature procedures which are well known to those skilled in the art, as for example in analogy to methods described in WO2010/034796, WO2010/034797 or WO2010/100249.

Scheme I [all variable groups are as defined in claim 1 and LG is a leaving group as for example CH$_3$O——, F$_2$HC—CH$_2$—O, Fluoro, Chloro, Bromo, Iodo, or CF$_3$(SO$_3$)]

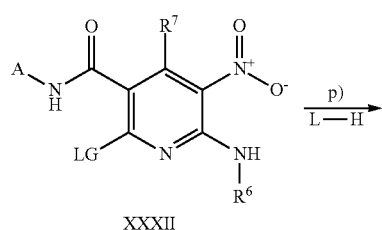

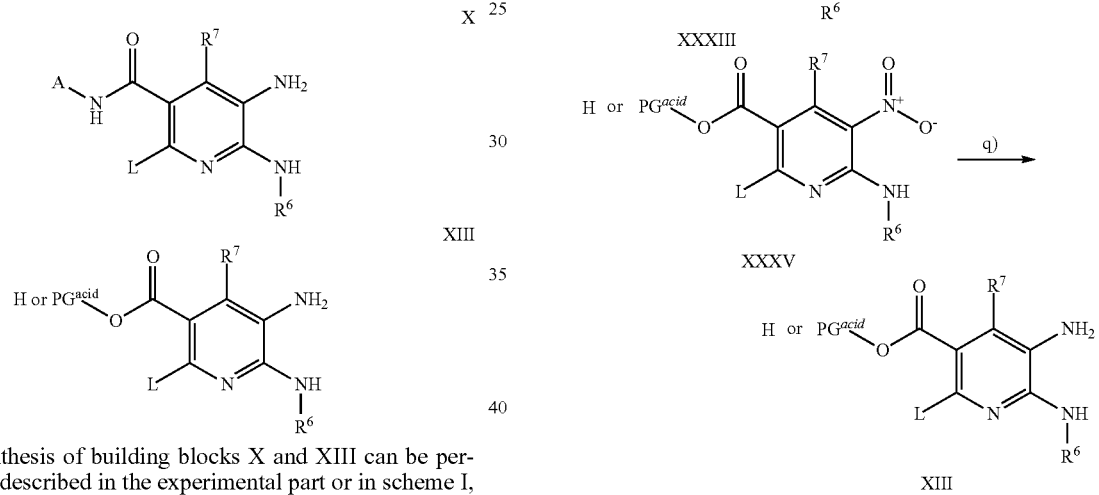

Step p can be performed by an aromatic substitution reaction of the building blocks XXXII or XXXIII with the amine L-H or an appropriate salt thereof and using literature known reaction conditions. For example the reaction can be performed employing a building blocks XXXII or XXXIII wherein LG is preferably a fluoro or chloro substituent in presence of a suitable base like K$_2$CO$_3$, Na$_2$CO$_3$, Cs$_2$CO$_3$, TEA, DIPEA in an appropriate solvent for example DMF, DMSO, DMA, NMP or mixtures of the above mentioned solvents at any suitable temperature between 0° C. to 180° C.

Alternatively, the reaction can also be preformed employing a building blocks XXXII or XXXIII wherein LG is preferably a methoxy or a 2,2-difluoroethoxy substituent in presence of a suitable base like K$_2$CO$_3$, Na$_2$CO$_3$, Cs$_2$CO$_3$, TEA, DIPEA or mixtures of bases in an appropriate solvent for example MeCN, DMF, DMSO, DMA, NMP or mixtures of the above mentioned solvents at any suitable temperature between 0° C. to 180° C.

Alternatively the reaction can also be performed in presence of a Pd-catalyst, in this case the preferred groups LG are bromo, iodo or trifluormethylsulfonyl in XXXII or XXXIII.

For example Pd(PPh$_3$)$_4$ can be used in presence of a suitable base for example K$_2$CO$_3$, Na$_2$CO$_3$, Cs$_2$CO$_3$, TEA, DIPEA in an appropriate solvent for example THF, MeCN, DMF or mixtures of the mentioned solvents preferably at a temperature between 0° C. to 120° C.

The nitro group in XXXIV or XXXV can be reduced to the amino group in step q) under literature known reduction conditions for example via hydrogenation (preferably at 1-5 bar) in presence of Pt/C, Pd/C or Raney-Nickel (Ra/Ni) in MeOH, EtOH or THF or mixtures thereof, optionally under acidic conditions in presence of HCl, or by using SnCl$_2$/HCl, Na$_2$S$_2$O$_4$, Zn/HCl, Fe/HCl, Fe-powder/aqueous NH$_4$Cl solution or according to procedures described in the literature for example R. Larock, *Comprehensive Organic Transformations*, VCH Verlagsgemeinschaft, Weinheim (1989). Appropriate solvent for this step is for example DCM, THF, MeCN, DMF, DMA, NMP, EtOH, MeOH or mixtures of the above mentioned solvents at any suitable temperature between 0° C. to 100° C.

Biological Assays mPGES Protein Production

Microsomes from Rosetta *E. coli* bacteria expressing recombinant human mPGES-1 can be derived as described below:

Inoculate 5 ml LB with Ampicilin (50 µg/ml) and Chloramphenicol (34 µg/ml) with bacteria from freeze culture. Incubate 8 h at 37° C. with 200 rpm. Thereafter, inoculate 500-1000 ml LB containing Amp and Chloro with the 5 ml on culture and grow to OD640 of 0.8-1.0. Chill the culture to +4° C. before induction. Induce the culture with IPTG at a final concentration of 400 µM. Express the protein at room temp 18-23° C. with 200 rpm shaking over night.

The following steps can be performed on the following day:
1. Spin down the cells in 250 ml centrifuge flasks for 15 min at 7000 rpm (Beckmann Coulte Avanti J-E centrifuge)
2. Dissolve the pellet from 250 ml culture in 12.5 ml homogenization buffer
3. (15 mM Tris-HCL pH8, 1 mM EDTA pH8, 0.25 mM Sucrose, 2.5 mM GSH, 1 Tablet Protease inhibitor per 50 ml buffer)
4. Disintegrate the cells by sonication, 5×10 seconds at 48% amplitude of a 750 W sonifier
5. Add 2.5 ml MgCl$_2$ (100 mM) and DNase 12.5 µl (0.8 mg/ml) and incubate on ice for 30 min
6. Spin down the bacteria debris and save the supernatant, 7000 rpm for 15 min
7. Isolate the protein containing membranes in the supernatant by ultracentrifugation 120000×g for 2 hour at 4° C. (Sorvall T880 rotor).
8. Discard the supernatant and dissolve the pellet in 20 mM Potassium phosphate buffer pH 7.4 (KH$_2$PO$_4$ and K$_2$HPO$_4$) buffer by sonication (5×10 s, 30% of a 50 W sonifier) and aliquot the enzyme and store aliquots at −80° C.

Before each experiment is performed an aliquot of the enzyme is thawed and it can then be dissolved in 0.1 M Potassium phosphate buffer pH7.4 (KH$_2$PO$_4$ and K$_2$HPO$_4$) buffer containing 2.5 mM GSH.

mPGES-1 Enzyme Assay

The aim of this assay is the determine the affinity of a test compound for the mPGES-1 enzyme.

47 µl of recombinant human mPGES-1 (~0.5 µg protein/well) containing microsomal suspension in a buffer containing GSH, (2.5 mmol/L L-Glutathione reduced, dissolved in 0.1 mol/L Phosphat Buffer pH 7.4) is dispensed in a 384-well plate and thereafter 1 µl of the test compound(s) is/are added and incubated for 25 minutes at room temperature. The enzyme reaction is started by the addition of 2 µl PGH2 (final conc. 2 µM) dissolved in water-free Diglyme. After 60 seconds the reaction is terminated by addition of a stop solution containing FeCl$_2$ (10 µL 0.074 mol/l FeCl$_2$). The samples are diluted between 1:25 in PBS (Phosphate Buffered Saline). 10 µl of the diluted samples are transferred to 384-well low volume plate. In order to quantify the amount of PGE$_2$ that has been formed, a homogenous time resolved fluorescent (HTRF) detecting of PGE$_2$ has been performed using a commercially available kit from Cisbio according to the manufactures recommendation. This HTRF-based assay has been described in detail (see: Goedken et al., J Biomol Screen, 2008, 13(7), 619-625). Briefly, the diluted samples are mixed with 5 µl PGE$_2$-d$_2$ conjungate and 5 µl anti-PGE$_2$ cryptate conjungate. After an incubation period of the plates over night, the fluorescence is measured by the use of an appropriate microplate reader.

The fluorescence of Europium cryptate (maxex=307 nm, maxem=620 nm) and d2-PGE$_2$ (maxex=620 nm, maxem=665 nm) are measured.

The extent of the specific HTRF is measured as a ratio of the emission intensity at 665 nm vs. that at 620 nm at an excitation puls of 320 nm. The quantification plate contains also wells with different concentrations of PGE$_2$ as calibration curve for the calculation of the PGE$_2$ concentrations from the HTRF ratio values.

From all mPGES enzyme assay the background is subtracted and the IC$_{50}$ is calculated over a nonlinear regression with conventional software.

TABLE A mPGES-1 inhibitory effect (IC$_{50}$ values in nM) of compounds in the enzyme assay

| example | IC$_{50}$ [nM] | example | IC$_{50}$ [nM] | example | IC$_{50}$ [nM] | example | IC$_{50}$ [nM] |
|---|---|---|---|---|---|---|---|
| 1 | 5 | 2 | 8 | 3 | 3 | 4 | 1 |
| 5 | 9 | 6 | 9 | 7 | 4 | 8 | 2 |
| 9 | 2 | 10 | 1 | 11 | 10 | 12 | 2 |
| 14 | 35 | 15 | 2 | 16 | 3 | 17 | |
| 18 | 2 | 19 | 4 | 20 | 2 | 21 | 4 |
| 22 | 3 | 23 | 1 | 24 | 1 | 25 | 4 |
| 26 | 4 | 27 | 3 | 28 | 1 | 29 | 10 |
| 30 | 3 | 31 | 3 | 32 | 4 | 33 | 2 |
| 34 | 2 | 35 | 5 | 36 | 2 | 37 | 3 |
| 38 | 2 | 39 | | 40 | 3 | 41 | 1 |
| 42 | 2 | 43 | 5 | 44 | 4 | 45 | 4 |
| 46 | <1 | | | | | | |

A549 Cell-Based Assay

Although the enzymatic assay is a high throughput assay the disadvantage is that it uses a recombinant protein which is not in its natural environment. Accordingly a cellular assay was established in which a cell line of human origin (A549) expressing the mPGES-1 protein was used. In addition in order to mimic the situation in humans in which compounds can be bound to plasma proteins 50% human serum is added in the assay. By having the combination of testing mPGES-1 in a cellular environment and the presence of 50% human serum this assay has a higher relevance to judge the therapeutic potential of a mPGES-inhibitor than the pure enzyme assay.

A549 cells (ATCC: CCL-185) are grown to about 90% confluence in F-12K Nutrient Mixture (Kaighn's Mod. Gibco) containing 10% FBS in a humified incubator at 37° C. and 5% CO$_2$. Cells were detached using Trypsin-EDTA.

A549 cells were seeded in a 384-well collagene plate at a density of 7000 cells/well (50 μl) in F-12 medium containing 1% Penicillin-Streptomycin and 50% human serum. The cells were allowed to attach for 3-4 h. After that the cells were incubated for 20-24 h in F-12k medium supplemented with 50% human serum, 1% Penicillin-Streptomycin and containing IL-1β at a final concentration of 5 ng/ml as well as 10 nM arachidonic acid in the presence of a vehicle or a test compound. The total volume is 100 μl.

Concentrations of $PGE_2$ in the cell free medium (10 μl) were measured using a commercially available HTRF kit from Cisbio (as described above). The $PGE_2$ formation in the absence of test compound was taken as 100%.

$IC_{50}$ values were derived from at 6-8 point titrations using conventional software.

The compounds listed in table B are in general efficacious to block the generation of $PGE_2$. Compounds of formula I may therefore be expected to have therapeutic potential to treat inflammatory diseases and associated conditions such as inflammatory/nociceptive pain.

TABLE B mPGES-1 inhibitory effect ($IC_{50}$ values in nM) of compounds in the cell assay

| example | $IC_{50}$ [nM] |
|---|---|
| 1 | 7 |
| 2 | 2 |
| 3 | 2 |
| 4 | 3 |
| 5 | 58 |
| 6 | |
| 7 | 11 |
| 8 | 11 |
| 9 | 6 |
| 10 | 8 |

TABLE B-continued mPGES-1 inhibitory effect ($IC_{50}$ values in nM) of compounds in the cell assay

| example | $IC_{50}$ [nM] |
|---|---|
| 11 | 47 |
| 12 | 2 |
| 14 | 86 |
| 15 | 10 |
| 16 | 3 |
| 17 | |
| 18 | 2 |
| 19 | 6 |
| 20 | 3 |
| 21 | 90 |
| 22 | 15 |
| 23 | 5 |
| 24 | 5 |
| 25 | 7 |
| 26 | 7 |
| 27 | 2 |
| 28 | 3 |
| 29 | 39 |
| 30 | 1 |
| 31 | 20 |
| 32 | 12 |
| 33 | 8 |
| 34 | 10 |
| 35 | 16 |
| 36 | 6 |
| 37 | 8 |
| 38 | 16 |
| 39 | 25 |
| 40 | 13 |
| 41 | 2 |
| 42 | 4 |
| 43 | 6 |
| 44 | 56 |
| 45 | 12 |
| 46 | 8 |

TABLE C

Comparison of enzym and cell IC50 (nM) of selected benzimidazoles

| Structure | Enzym IC50 | Cell IC50 |
|---|---|---|
| 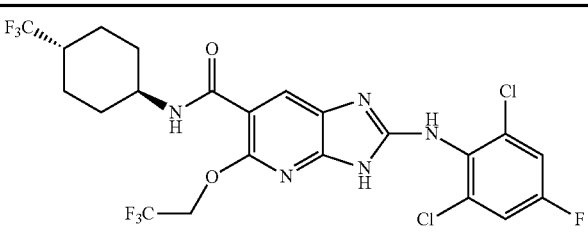 of WO 2010/034799 | 2 | 43 |
| 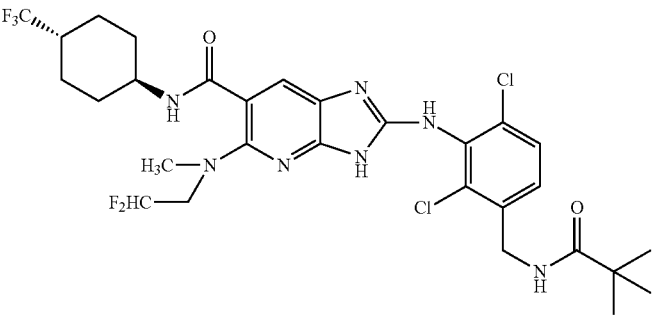 [SMILES: CN(CC(F)F)c1nc2[nH]c(Nc3c(Cl)ccc(CNC(=O)C(C)(C)C)c3Cl)nc2cc1C(=O)N[C@H]1CC[C@H](C(F)(F)F)CC1] | 1 | 3 |

TABLE C-continued

Comparison of enzym and cell IC50 (nM) of selected benzimidazoles

| Structure | Enzym IC50 | Cell IC50 |
|---|---|---|
| Example 4 (of WO 2010/034799) | 4 | 161 |
| [structure] | 9 | 58 |
| Example 5 [structure] | 5 | 7 |
| Example 1 [structure] | 8 | 89 |
| (of WO 2010/100249) [structure] | 2 | 72 |
| (of WO 2010/034799) | | |

TABLE C-continued

Comparison of enzym and cell IC50 (nM) of selected benzimidazoles

| Structure | Enzym IC50 | Cell IC50 |
|---|---|---|
| Example 41 | 1 | 2 |
| of WO 2010/100249 | 1 | 8 |

Tables A, B and C demonstrate that compounds with a similar affinity for the mPGES-1 enzyme as measured in the enzyme assay may have different potencies in the cell based assay.

Data from a cell based pharmacological assay when compared with data from an enzyme assay are considered to allow for a better predictability and estimation of therapeutic effective concentrations/doses. Compounds of the present invention show high potency in both assays. Consequently, they are likely to be more suitable for the in-vivo use.

METHOD OF TREATMENT

The present invention relates to compounds of formula I which are useful in the prevention and/or treatment of a disease and/or condition in which the inhibition of prostaglandin E synthases, in particular that of the microsomal prostaglandin $E_2$ synthase-1 (mPGES-1) is of therapeutic benefit, including but not limited to the treatment and/or prevention of inflammatory diseases and/or associated conditions.

The term "inflammation" will be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Where a condition has an inflammatory component associated with it, or a condition characterised by inflammation as a symptom, the skilled person will appreciate that compounds of the invention may be useful in the treatment of the inflammatory symptoms and/or the inflammation associated with the condition.

Compounds of the invention may also have effects that are not linked to inflammatory mechanisms, such as in the reduction of bone loss in a subject. Such conditions include osteoporosis, osteoarthritis, Paget's disease and/or periodontal diseases.

A further aspect of the present invention relates to a compound of formula I as a medicament.

Another aspect of the present invention is the use of compounds of formula I for the treatment and/or prevention of a disease and/or condition in which the inhibition of the mPGES-1 is of therapeutic benefit.

A further aspect of the present invention is the use of a compound of formula I for the treatment and/or prevention of inflammatory diseases and/or associated conditions.

The present invention also relates to the use of compounds of formula I for the treatment and/or prevention of the following diseases and conditions:

1. Rheumatic diseases or autoimmune diseases or muscoskeletal diseases: all forms of rheumatic diseases including e.g. soft tissue rheumatism, rheumatoid arthritis, polymyalgia rheumatica, reactive arthritis, tenosynovitis, gout or metabolic arthritis, bursitis, tendonitis, juvenile arthritis, spondyloarthropathies like e.g. spondylitis, ankylosing spondylitis, psoriatric arthropathy; sarcoidosis, fibromyalgia, myositis, polymyositis, osteoarthritis, traumatic arthritis, collagenoses of any origin e.g. systemic lupus erythematosus, scleroderma, dermatomyositis, Still's Disease, Sjögren syndrome, Felty syndrome; rheumatic fever and rheumatic heart disease, diseases of blood vessels like vasculitis, polyarthritis nodosa, Behcet's syndrome, giant cell arthritis, Wegener's granulomatosis, Henoch-Schönlein purpura; psoriatic arthritis, fungal arthritis, in particular including pain associated with any of the aforementioned conditions;

2. Headaches such as migraines with and without aura, tension-type headaches, cluster headaches and headaches with different origins;

3. Sympathetically maintained pain like complex regional pain syndrome Type I and II;

4. Neuropathic pain such as low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain;

5. Cancer pain induced by or associated with tumors such as bone tumors, lymphatic leukemia; Hodgkin's disease, malignant lymphoma; lymphogranulomatoses; lymphosarcoma; solid malignant tumors; extensive metastases;

6. Visceral disorders such as chronic pelvic pain, pancreatitis, peptic ulcer, interstitial cystitis, cystitis, renal colic, angina, dysmenorrhoea, menstruation, gynaecological pain, irritable bowel disease (IBS), inflammatory bowel disease, Crohn's disease and ulcerative colitis, nephritis, prostatitis, vulvodynia, non-ulcer dyspepsia, non-cardiac chest pain, myocardial ischemia;

7. Inflammation associated diseases of ear, nose, mouth and throat like influenza and viral/bacterial infections such as the common cold, allergic rhinitis (seasonal and perennial), pharyngitis, tonsillitis, gingivitis, larhyngitis, sinusitis, and vasomotor rhinitis, fever, hay fever, thyroiditis, otitis, dental conditions like toothache, perioperative and post-operative conditions, trigeminal neuralgia, uveitis; iritis, allergic keratitis, conjunctivitis, blepharitis, neuritis nervi optici, choroiditis, glaucoma and sympathetic opthalmia, as well as pain thereof;

8. Neurological diseases such as cerebral oedema and angioedema, cerebral dementia like e.g. Parkinson's and Alzheimers disease, senile dementia; multiple sclerosis, epilepsy, drug resistant epilepsy, stroke, myasthenia gravis, brain and meningeal infections like encephalomyelitis, meningitis, including HIV as well as schizophrenia, delusional disorders, autism, affective disorders and tic disorders;

9. Work-related diseases like pneumoconiosis, including aluminosis, anthracosis, asbestosis, chalicosis, ptilosis, siderosis, silicosis, tabacosis and byssinosis;

10. Lung diseases such as asthma including allergic asthma (atopic or non-atopic) as well as exercise-induced bronchoconstriction, occupational asthma, viral- or bacterial exacerbation of asthma, other non-allergic asthmas and "wheezy-infant syndrome", Chronic obstructive pulmonary disease (COPD) including emphysema, adult respiratory distress syndrome, bronchitis, pneumonia, adult respiratory distress syndrome (ARDS), pigeon fancier's disease, farmers lung;

11. Skin diseases such as psoriasis and eczema, dermatitis, sunburn, burns as well as aprains and strains and tissue trauma;

12. Vascular and heart diseases which are inflammation-related like artheriosclerosis including cardiac transplant atherosclerosis, panarteritis nodosa, periarteritis nodosa, arteritis temporalis, Wegner granulomatosis, giant cell arthritis, reperfusion injury and erythema nodosum, thrombosis (e.g. deep vein thrombosis, renal, hepatic, portal vein thrombosis); coronary artery disease, aneurysm, vascular rejection, myocardial infarction, embolism, stroke, thrombosis including venous thrombosis, angina including unstable angina, coronary plaque inflammation, bacterial-induced inflammation including *Chlamydia*-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries, artery restenosis;

13. Diabetes-associated symptoms such as diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion);

14. Benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers effecting epithelial cells throughout the body; neoplasias like gastrointestinal cancer, Barrett's esophagus, liver cancer, bladder cancer, pancreatic cancer, ovarian cancer, prostate cancer, cervical cancer, lung cancer, breast cancer and skin cancer; adenomatous polyps, including familial adenomatous polyposis (FAP) as well preventing polyps from forming in patients at risk of FAP.

15. Various other disease states and conditions like epilepsy, septic shock e.g. as antihypovolemic and/or antihypotensive agents, sepsis, osteoporosis, benign prostatic hyperplasia and hyperactive bladder, nephritis, pruritis, vitiligo, disturbances of visceral motility at respiratory, genitourinary, gastrointestinal or vascular regions, wounds, allergic skin reactions, mixed-vascular and non-vascular syndromes, septic shock associated with bacterial infections or with trauma, central nervous system injury, tissue damage and postoperative fever, syndromes associated with itching.

Preferred according to the present invention is the use of a compound of formula I for the treatment and/or prevention of pain; in particular pain that is associated with any one of the diseases or conditions listed above.

Another aspect of the present invention is a method for the treatment and/or prevention of above mentioned diseases and conditions, which method comprises the administration of an effective amount of a compound of formula I to a human being.

Dosage

The dose range of the compounds of formula I applicable per day is usually from 0.01 to 5000 mg, preferably from 1 to 2000 mg, more preferably from 5 to 500 mg, most preferably 10 to 250 mg. Each dosage unit may conveniently contain from 2 to 500 mg, preferably 5 to 250 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Formulations

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

A further aspect of the invention is a pharmaceutical formulation including a compound of formula I in admixture with a pharmaceutically acceptable adjuvant, diluent or carrier.

Combination Therapy

The compounds according to the present invention can be combined with other treatment options known to be used in the art in connection with a treatment of any of the indications the treatment of which is in the focus of the present invention.

Among such treatment options that are considered suitable for combination with the treatment according to the present inventions are:
- non-steroidal antiinflammatory drugs (NSAIDs) including COX-2 inhibitors;
- opiate receptor agonists;
- Cannabionoid agonists or inhibitors of the endocannabinoid pathway
- Sodium channel blockers;
- N-type calcium channel blockers;
- serotonergic and noradrenergic modulators;
- corticosteroids;
- histamine H1 receptor antagonists;
- histamine H2 receptor antagonists;
- proton pump inhibitors;
- leukotriene antagonists and 5-lipoxygenase inhibitors;
- local anesthetics;
- VR1 agonists and antagonists;
- Nicotinic acetylcholine receptor agonists;
- P2X3 receptor antagonists;
- NGF agonists and antagonists or anti-NGF antibodies;
- NK1 and NK2 antagonists;
- Bradykinin B1 antagonists
- CCR2 antagonists
- iNOS or nNOS or eNOS inhibitors
- NMDA antagonist;
- potassium channel modulators;
- GABA modulators;
- serotonergic and noradrenergic modulators;
- anti-migraine drugs;
- neuropathic pain drugs such as pregabaline or duloxetine.

Said list is not considered to have a limiting character.

In the following representative examples of such treatment options shall be given.

Non-steroidal antiinflammatory drugs (NSAIDs) including COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenylcarboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) and the like;

Antiviral drugs like acyclovir, tenovir, pleconaril, peramivir, pocosanol and the like.

Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol and the like;

Opiate receptor agonists: morphine, propoxyphene (Darvon), tramadol, buprenorphin and the like.

Glucocorticosteroids such as bethamethasone, budesonide, dexamethasone, hydrocortisone, methylprednisolone, prednisolone, prednisone, triamcinolone and deflazacort; immunosuppressive, immunomodulatory, or cytsostatic drugs inlcuding but not limited to hydroxychlorquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide and the like;

anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab and the like;

IL-1 receptor antagonists such as but not limited to Kineret;

Sodium channel blockers: carbamazepine, mexiletine, lamotrigine, tectin, lacosamide and the like.

N-type calcium channel blockers: Ziconotide and the like.

Serotonergic and noradrenergic modulators: paroxetine, duloxetine, clonidine, amitriptyline, citalopram;

Histamine H1 receptor antagonists: bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine and the like;

Histamine H2 receptor antagonists: cimetidine, famotidine and ranitidine and the like;

Proton pump inhibitors: omeprazole, pantoprazole and esomeprazole and the like;

Leukotriene antagonists and 5-lipoxygenase inhibitors: zafirlukast, mon-telukast, pranlukast and zileuton and the like;

Local anesthetics such as ambroxol, lidocaine and the like;

Potassium channel modulators: like retigabine;

GABA modulators: lacosamide, pregabalin, gabapentin and the like;

Anti-migraine drugs: sumatriptan, zolmitriptan, naratriptan, eletriptan, telcegepant and the like;

NGF antibodies such as RI-724 and the like.

Combination therapy is also possible with new principles for the treatment of pain e.g. P2X3 antagonists, VR1 antagonists, NK1 and NK2 antagonists, NMDA antagonists, mGluR antagonists and the like.

The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased pharmacological effect, or some other beneficial effect of the combination compared with the individual components.

EXPERIMENTAL SECTION

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

| Abbreviations: | |
| --- | --- |
| AcOH | acetic acid |
| aq | aqueous |
| Boc | tert-butoxycarbonyl |
| Boc$_2$O | di-tert-butyl-dicarbonate |
| CE | chromatography equipment |
| CH | cyclohexane |
| conc | concentrated |
| DCM | dichloromethane |
| DIC | N,N-diisopropylcarbodiimide |
| DIPEA | N-ethyldiisopropylamine |
| DMSO | dimethylsulphoxide |
| DMF | N,N-dimethylformamide |
| EtOAc | ethyl acetate |
| Et$_2$O | diethyl ether |
| EtOH | ethanol |
| HPLC | high performance liquid chromatography |
| i-PrOH | isopropanol |
| MeCN | acetonitrile |
| MeOH | methanol |
| MS | mass spectrometry |
| PE | petrol ether |
| Pd/C | 10% Palladium on carbon |
| Ra-Ni | Raney-Nickel |
| RP | reversed phase |
| rt | room temperature |
| $R_f$ | retention factor |
| $R_t$ | retention time |
| sat | saturated |
| TBTU | O-(benzotriazol-1-yl)-N,N,N',N'-tetramethyluronium tetrafluoroborate |
| TEA | triethylamine |
| THF | tetrahydrofuran |
| TFA | trifluoroacetic acid |
| TLC | thin layer chromatography |

Analytical Methods

All compounds specified in the examples below gave the correct mass spectra matching the theoretical isotope pattern. For practical reasons, only one of the major isotope peaks is given as representative data for the mass spectrum.

The TLC data is obtained by using the following tlc plates
  a) Silica gel plates 60 F254 Merck No 1.05714.0001 abbreviated in the experimental part as "silica gel"
  b) Reversed phase plates: RP-8 F 254s Merck No: 1.15684.0001 abbreviated in the experimental part as "RP-8".
  c) Aluminiumoxide plates 60 F254 Merck 1.05713.0001 abbreviated in the experimental part as "Alox"

The $R_f$ values given are determined without chamber saturation.

Flash chromatography purifications are performed using silica gel from Millipore (MATREX™, 35 bis 70 μm) or Alox (E. Merck, Darmstadt, Aluminiumoxid 90 standardisiert, 63 bis 200 μm, Artikel-Nr: 1.01097.9050).

The HPLC/MS data, where specified, are obtained under the following conditions:
CE1:
Agilent HP 1200 with binary pump, Agilent MS 6140, HiPALS1367C
The diode array detection is measured in a wavelength range of 190-400 nm.
Range of mass-spectrometric detection: m/z 100 to m/z 1000.
CE 2:
Agilent HP 1100, Agilent MS G6140
The diode array detection is measured in a wavelength range of 210-400 nm.
CE3
Waters Acquity with DA and MS detector.
The following methods are used (if not stated otherwise the column temperature is 25° C.):
Method A (CE 2):
Stationary phase (column temperature: constant at 60° C.): XBridge C18, 4.6×30 mm, 3.5 μm
Mobile phase: E1: water with 0.1% TFA, E2: MeOH with 0.1% TFA
Eluent gradient:

| time in min | % E1 | % E2 | flow rate in mL/min |
| --- | --- | --- | --- |
| 0.0 | 95 | 5 | 4 |
| 0.15 | 95 | 5 | 4 |
| 1.7 | 0 | 100 | 4 |
| 2.25 | 0 | 100 | 4 |

Method B (CE1):
Stationary phase: Zorbax Stable Bond C18, 1.8 μm, 3.0×30 mm
Mobile phase: E1: water with 0.15% HCOOH, E2: MeCN
Eluent gradient:

| time in min | % E1 | % E2 | flow rate in mL/min |
| --- | --- | --- | --- |
| 0.00 | 95 | 5 | 1.6 |
| 1.00 | 10 | 90 | 1.6 |
| 2.50 | 10 | 90 | 1.6 |
| 2.75 | 95 | 5 | 1.6 |

Method C(CE1):
Stationary phase: As described in method B.
Mobile phase: E1: water with 0.15% HCOOH, E2: MeCN
Eluent gradient:

47

| time in min | % E1 | % E2 | flow rate in mL/min |
|---|---|---|---|
| 0.00 | 95 | 5 | 1.6 |
| 2.25 | 10 | 90 | 1.6 |
| 2.50 | 10 | 90 | 1.6 |
| 2.75 | 95 | 5 | 1.6 |

Method D (CE 2):

Stationary phase (column temperature: constant at 60° C.): Sunfire C18, 4.6×30 mm, 3.5 μm Mobile phase: E1: water with 0.1% TFA, E2: MeOH with 0.1% TFA Eluent gradient:

| time in min | % E1 | % E2 | flow rate in mL/min |
|---|---|---|---|
| 0.0 | 95 | 5 | 4 |
| 0.15 | 95 | 5 | 4 |
| 1.7 | 0 | 100 | 4 |
| 2.25 | 0 | 100 | 4 |

Method E (CE1):

Stationary phase (column temperature: constant at 40° C.): Waters XBridge C18, 2.5 μm, 3.0×30 mm Mobile phase and eluent gradient as described in method C.

Method F (CE 2):

Stationary phase (column temperature: constant at 60° C.): XBridge C18, 4.6×30 mm, 3.5 μm Mobile phase: E1: water with 0.1% NH$_4$OH, E2: MeOH Eluent gradient:

| time in min | % E1 | % E2 | flow rate in mL/min |
|---|---|---|---|
| 0.0 | 95 | 5 | 4 |
| 0.15 | 95 | 5 | 4 |
| 1.7 | 0 | 100 | 4 |
| 2.1 | 0 | 100 | 4 |

Method G (CE3)

Stationary phase (column temperature: constant at 60° C.): Ascentis Express C18_2.1×50 mm, 2.7 μm.

Mobile phase: E1: water with 0.1% TFA, E2: MeCN with 0.08% TFA

Eluent gradient:

| time in min | % E1 | % E2 | flow rate in mL/min |
|---|---|---|---|
| 0.00 | 95 | 5 | 1.5 |
| 0.7 | 1 | 99 | 1.5 |
| 0.8 | 1 | 99 | 1.5 |
| 0.81 | 95 | 5 | 1.5 |

48

Synthesis of Building Blocks of the 2,3,4-Trisubstituted Benzylamine-Type

Building Block A

N-(2,4-Dichloro-3-isothiocyanato-benzyl)-2,2-dimethyl-propionamide (a) 3-Acetylamino-2,4-dichloro-benzoic acid Water (110 mL) is added to N-(2,6-dichloro-3-methyl-phenyl)-acetamide (13 g, 59 mmol) in pyridine (30 mL). The mixture is heated to 70° C. and KMnO$_4$ (47 g, 298 mmol) is cautiously added portionwise. After 6 h at reflux the reaction mixture is filtered through a pad of celite and washed with hot water. The filtrate is cooled to rt, concentrated and slowly acidified with 6 M aq. HCl solution. The mixture is cooled in an ice bath, filtered and the filtercake is washed with cold water and dried to give the sub-title compound.

Yield: 11.6 g (78%). $R_f$=0.1 (silica gel, DCM:EtOH 9:1). MS m/z: 248 [M+H]$^+$.

(b) 3-Amino-2,4-dichloro-benzoic acid

3-Acetylamino-2,4-dichloro-benzoic acid (21.0 g, 84.6 mmol) is stirred in 6 M aq. HCl-solution (120 mL) and AcOH (250 mL) at reflux for 24 h. The reaction mixture is cooled, concentrated, diluted with water and concentrated again. The residue is diluted with water, stirred under cooling and filtered. The filtercake is washed and dried to give the sub-title compound.

Yield: 16.8 g (96%). MS m/z: 204 [M−H]$^−$. HPLC-method C: $R_t$=1.46 min.

(c) 3-Amino-2,4-dichloro-benzamide (1-Chloro-2-methyl-propenyl)-dimethyl-amine (16.1 mL, 116 mmol) is added to 3-amino-2,4-dichloro-benzoic acid (20.0 g, 97.1 mmol) in THF (320 mL). After 4 h at rt the mixture is added dropwise to conc. NH$_3$ (320 mL) and stirred at rt overnight. The reaction mixture is concentrated, cooled and filtered. The filtercake is dried to give the sub-title compound.

Yield: 17.4 g (87%). MS m/z: 205 [M+H]$^+$. HPLC-method C: $R_t$=1.19 min.

(d) 3-Amino-2,4-dichloro-benzylamine

3-Amino-2,4-dichloro-benzamide (2.00 g, 9.8 mmol) in THF (45 mL) is added dropwise to LiAlH$_4$ (1 M in THF, 24.4 mL) in THF (45 mL). The reaction mixture is stirred for 1 h at rt and 10 h at reflux. Excess LiAlH$_4$ is destroyed under cooling as described by L. F. Fieser & M. Fieser Vol 1, p 584 Wiley 1967. After 30 min the mixture is filtered and the filtrate is concentrated to give the sub-title compound.

Yield: 1.85 g (99%). $R_f$=0.12 (silica gel, DCM:EtOH 95:5). MS m/z: 191 [M+H]$^+$.

(e) N-(3-Amino-2,4-dichloro-benzyl)-2,2-dimethyl-propionamide

3-Amino-2,4-dichloro-benzylamine (2.28 g, 11.9 mmol) is added to a mixture of 2,2-dimethyl-propionic acid chloride (1.47 mL, 11.9 mmol) and TEA (4.14 mL, 29.8 mmol) in THF (90 mL) and it is stirred for 3 h. The reaction mixture is concentrated, diluted with EtOAc, washed with 5% aq. NaHCO$_3$ solution and water, dried with Na$_2$SO$_4$ filtered and concentrated to give the sub-title compound.

Yield: 3.1 g (94%). $R_t$=0.61 (silica gel, DCM:EtOH 95:5).

(f) N-(2,4-Dichloro-3-isothiocyanato-benzyl)-2,2-dimethyl-propionamide 1,1'-Thiocarbonyldi-2-pyridone (4.87 g, 21 mmol) is added to a mixture of N-(3-amino-2,4-dichloro-benzyl)-2,2-dimethyl-propionamide (5.50 g, 20 mmol) and dioxane (200 mL) and stirred at rt for 2 h and at reflux for 8 h. The mixture is concentrated, diluted with DCM and filtered over silica gel. The filtrate is concentrated to give the sub-title compound.

Yield: 6.00 g (95%). HPLC-method B: $R_t$=1.58 min. MS m/z: 318 [M+H]$^+$.

Building Block B (2,4-Dichloro-5-fluoro-3-isothiocyanato-benzyl)-carbamic acid tert-butyl ester

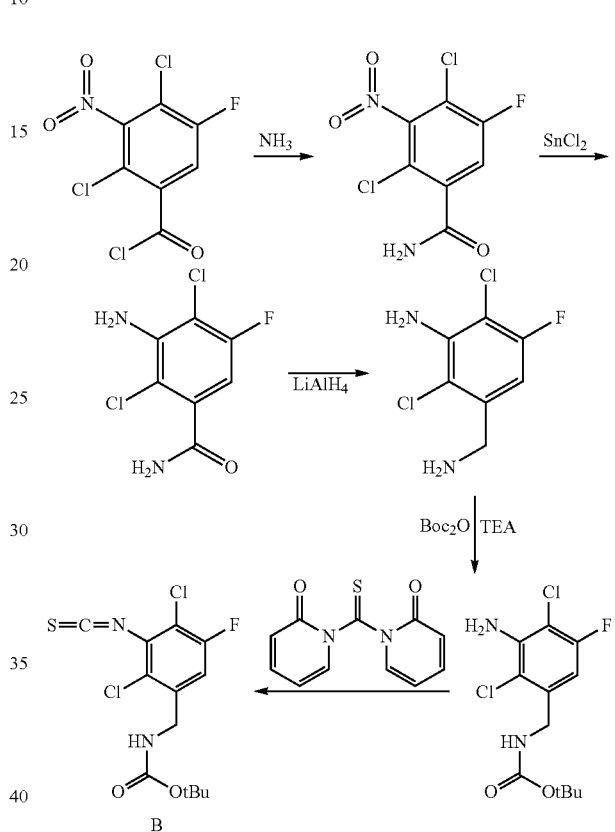

(a) 2,4-Dichloro-5-fluoro-3 nitro-benzamide

32%-aq. NH$_3$-solution (250 mL) is dropped to 2,4-dichloro-5-fluoro-3 nitro-benzoic acid chloride (16.0 g, 59 mmol) in 100 mL THF and it is stirred for 20 min. Then the mixture is concentrated and the resulting precipitate is collected and dried.

Yield: 14.6 g (98%). HPLC-method E: $R_t$=1.66 min. MS m/z: 251 [M−H]$^−$.

(b) 2,4-Dichloro-5-fluoro-3 amino-benzamide

A mixture of 2,4-dichloro-5-fluoro-3 nitro-benzamide (7.00 g, 27.7 mmol), Sn(II)Cl$_2$×2H$_2$O (28 g, 124 mmol) and EtOAc (250 mL) is stirred for 3 h at reflux and then carefully added to a sat. aq. NaHCO$_3$-solution (250 mL). The resulting mixture is filtered through a pad of celite, the organic phase is separated and washed with brine, dried with MgSO$_4$ and concentrated.

Yield: 6.01 g (97%). HPLC-method E: $R_t$=1.19 min.

(c) 3-Amino-2,4-dichloro-5-fluoro-benzylamine 2,4-Dichloro-5-fluoro-3 amino-benzamide (6.00 g, 26.9 mmol) in THF (175 mL) is added dropwise to LiAlH$_4$ (1 M in THF, 28.0 mL) in THF (175 mL). The reaction mixture is stirred for 1 h at rt and 5 h at reflux. Excess LiAlH₄ is destroyed under cooling as described by L. F. Fieser & M. Fieser Vol 1, p 584 Wiley 1967. After 30 min the mixture is filtered, the filtrate is concentrated, diluted with Et₂O and the precipitate is collected.

Yield: 2.75 g (49%). HPLC-method A: $R_t$=0.66 min.

(d) (3-Amino-2,4-dichloro-5-fluoro-benzyl)-carbamic acid tert-butyl ester

A mixture of Boc₂O (3.76 g, 17.2 mmol), 3-amino-2,4-dichloro-5-fluoro-benzylamine (3.60 g, 17.2 mmol) and 100 mL THF is stirred over the weekend and concentrated.

The mixture is concentrated, diluted with CH, filtered and the filtrate is diluted with DCM, filtered over silica gel and concentrated.

Yield: 5.80 g (95%). HPLC-method A: $R_t$=1.74 min. MS m/z: 351 [M+H]⁺.

Example 1

N-(trans-4-Trifluoromethyl-cyclohexyl)-2-{2-chloro-5-[(1-trifluoromethyl-cyclopropyl-carbonylamino)methyl]-phenylamino}-5-[4-trifluoromethyl-piperidinyl]-3-methyl-3H-imidazo[4,5-b]pyridine-6-carboxamide

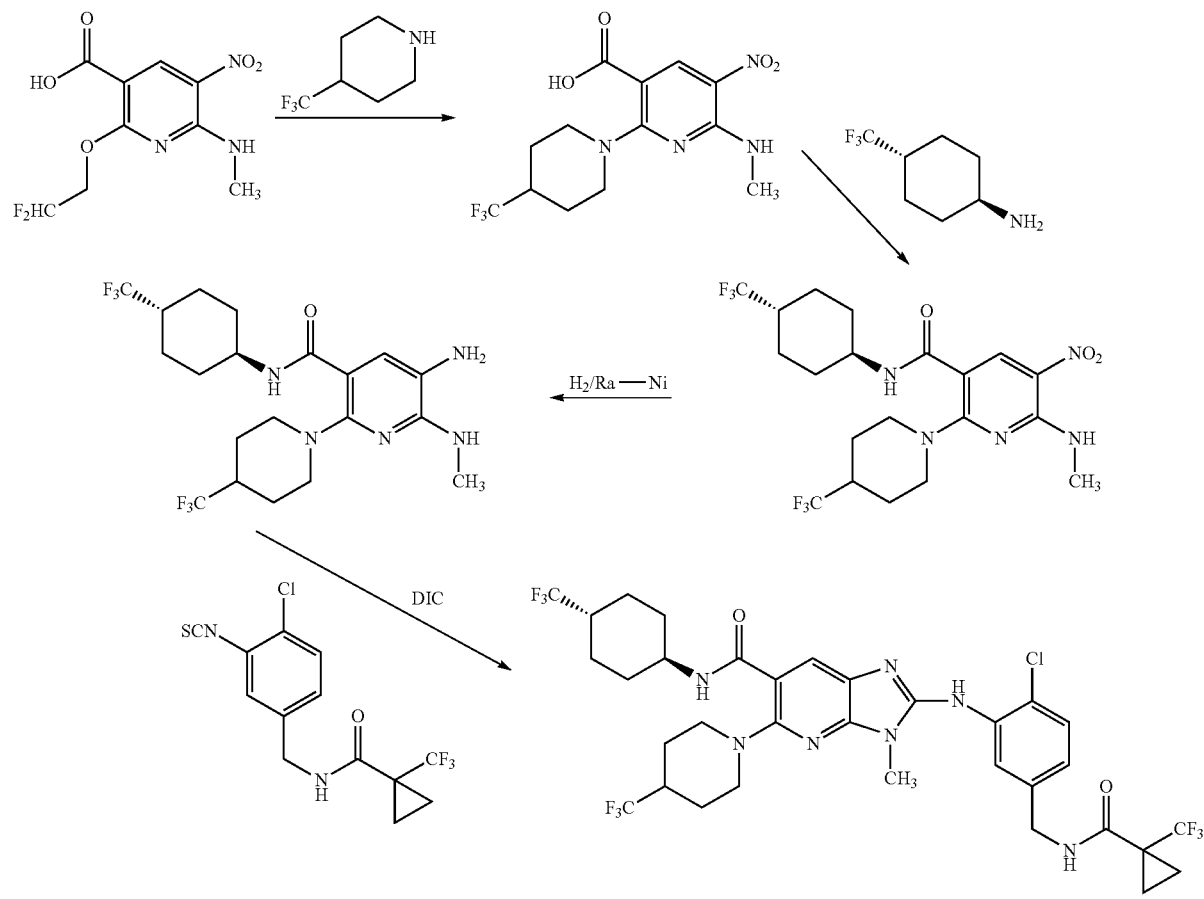

Yield: 5.37 g (quantitative). HPLC-method E: $R_t$=2.11 min.

(e) (2,4-Dichloro-5-fluoro-3-isothiocyanato-benzyl)-carbamic acid tert-butyl ester 1,1'-Thiocarbonyldi-2-pyridone (4.03 g, 17.3 mmol) is added to a mixture of (3-amino-2,4-dichloro-5-fluoro-benzyl)-carbamic acid tert-butyl ester (5.37 g, 17.3 mmol) and dioxane (100 mL) and the mixture is stirred at reflux for 2 d.

(a) 6-Methylamino-5-nitro-2-(4-trifluoromethyl-piperidinyl)-nicotinic acid

A mixture of 4-trifluoromethyl-piperidine (330 mg, 2.2 mmol), TEA (1.00 mL, 7.2 mmol), 2-(2,2-difluoro-ethoxy)-6-methylamino-5-nitro-nicotinic acid (500 mg, 1.8 mmol, prepared according to WO2010/34799), DMF (5 mL) and MeCN (5 mL) is stirred for 3 h at rt. Then Cs₂CO₃ (1.5 g, 4.6 mmol) is added and it is stirred overnight at rt and for 6 h at 70° C. Water is added and the mixture is concentrated i.vac.

The residue is diluted with water, HCOOH is added and the resulting precipitate is filtered, washed with water and dried.

Yield: 570 mg. HPLC $R_t$=1.97 min (method E). MS m/z: 349 [M+H]$^+$.

(b) N-(trans-4-Trifluoromethyl-cyclohexyl)-6-methylamino-5-nitro-2-(4-trifluoromethyl-piperidinyl)-nicotinic acid amide A mixture of 6-methylamino-5-nitro-2-(4-trifluoromethyl-piperidinyl)-nicotinic acid (570 mg, 1.64 mmol), TBTU (540 mg, 1.68 mmol), TEA (1.00 mL, 7.2 mmol), THF (10 mL) and DMF (5 mL) are stirred for 5 min. Then trans-4-trifluoromethyl-cyclohexylamine (335 mg, 1.65 mmol) is added and it is stirred for 30 min. Water is added, the mixture is concentrated and the precipitate is filtered, washed with water and dried at 55° C.

Yield: 0.710 g (87%). HPLC $R_t$=2.32 min (method E). MS m/z: 498 [M+H]$^+$.

(c) N-(trans-4-Trifluoromethyl-cyclohexyl)-6-methylamino-5-amino-2-(4-trifluoromethyl-piperidinyl)-nicotinic acid amide A mixture of N-(trans-4-trifluoromethyl-cyclohexyl)-6-methylamino-5-nitro-2-(4-trifluoromethyl-piperidinyl)-nicotinic acid amide (120 mg, 0.24 mmol), Ra—Ni (30 mg) and THF (20 mL) is stirred under 50 psi H$_2$-atmosphere for 4 h. The mixture is filtered, and the filtrate is concentrated.

Yield: 0.110 g (98%). HPLC $R_t$=1.98 min (method E). MS m/z: 468 [M+H]$^+$.

(d) N-(trans-4-Trifluoromethyl-cyclohexyl)-2-{2-chloro-5-[(1-trifluoromethyl-cyclopropyl-carbonylamino)methyl]-phenylamino}-5-[4-trifluoromethyl-piperidinyl]-3-methyl-3H-imidazo[4,5-b]pyridine-6-carboxamide A mixture of N-(trans-4-trifluoromethyl-cyclohexyl)-6-methylamino-5-amino-2-(4-trifluoromethyl-piperidinyl)-nicotinic acid amide (110 mg, 0.24 mmol), N-(4-chloro-3-isothiocyanato-benzyl)-1-trifluoromethyl-cyclopropylcarboxamide (prepared according to WO2010/100249; 80 mg, 0.24 mmol) and MeCN (7.5 mL) is stirred for 5 h. Then DIC (50 µl, 0.32 mmol) is added and it is stirred overnight at rt and for 2 h at 60° C. The crude mixture is diluted with 40% aq. methylamine-solution, filtered, concentrated and purified by prep. HPLC (X-bridge C18 column; water (+0.15% aq. Ammonia)/MeOH 9:1->MeOH).

Yield: 130 mg (72%). HPLC $R_t$=2.37 min (method E). MS m/z: 768 [M+H]$^+$.

Example 2

N-(trans-4-Trifluoromethyl-cyclohexyl)-2-{2,6-dichloro-3-[(2,2-dimethyl-propionylamino)-methyl]-phenylamino}-5-[-fluoro-piperidinyl]-3-methyl-3H-imidazo[4,5-b]pyridine-6-carboxamide

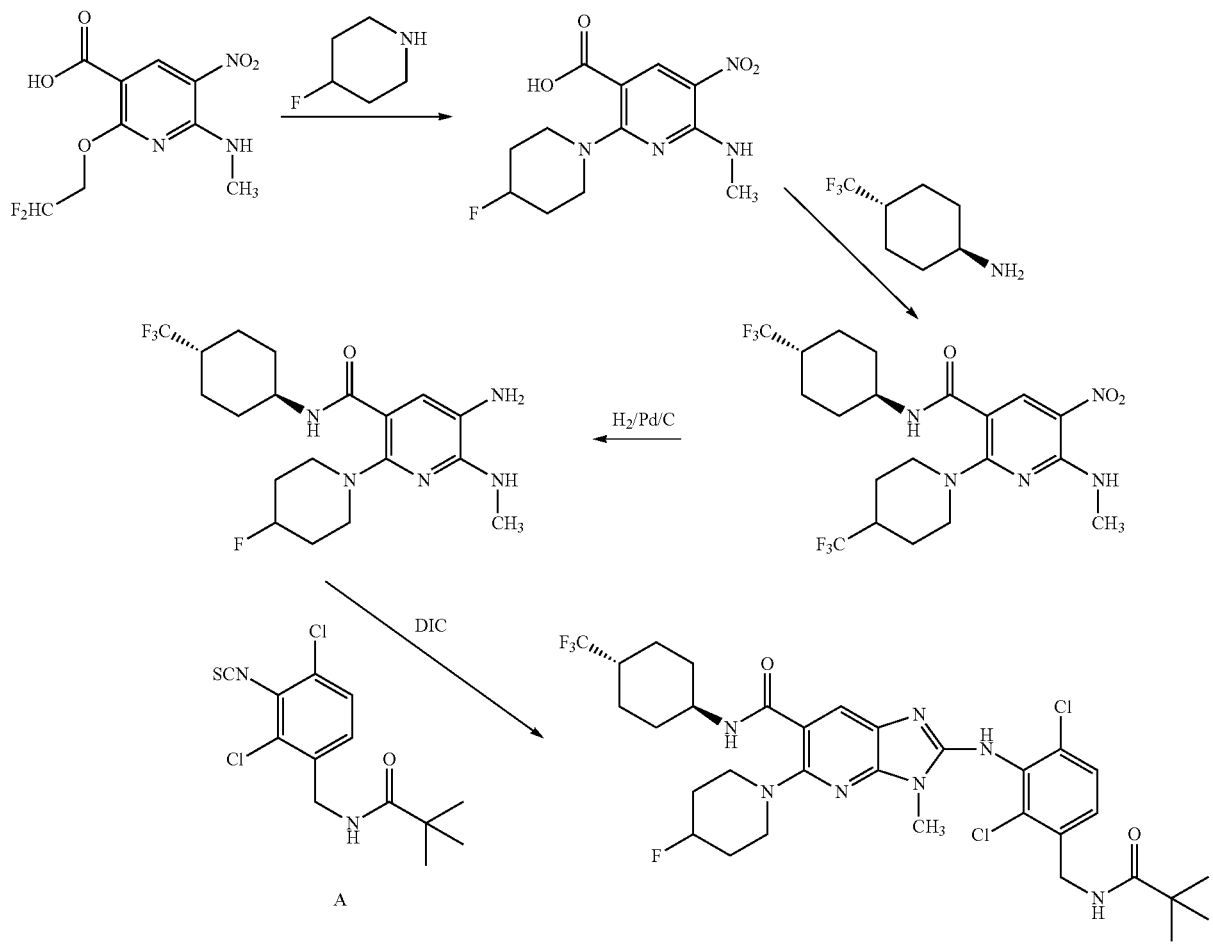

(a) 6-Methylamino-5-nitro-2-(4-fluoro-piperidinyl)-nicotinic acid

The subtitle compound is prepared in analogy to 1a from 2-(2,2-difluoro-ethoxy)-6-methylamino-5-nitro-nicotinic acid and 4-fluoro-piperidine and TEA/Cs$_2$CO$_3$ HPLC R$_t$=1.27 min (method B). MS m/z: 299 [M+H]$^+$.

(b) N-(trans-4-Trifluoromethyl-cyclohexyl)-6-methylamino-5-nitro-2-(4-fluoro-piperidinyl)-nicotinic acid amide The subtitle compound is prepared in analogy to 1b from 6-methylamino-5-nitro-2-(4-fluoro-piperidinyl)-nicotinic acid, trans-4-trifluoromethyl-cyclohexylamine, TBTU and TEA.

HPLC R$_t$=1.46 min (method B). MS m/z: 448 [M+H]$^+$.

(c) N-(trans-4-Trifluoromethyl-cyclohexyl)-6-methylamino-5-amino-2-(4-fluoro-piperidinyl)-nicotinic acid amide A mixture of N-(trans-4-trifluoromethyl-cyclohexyl)-6-methylamino-5-nitro-2-(4-fluoro-piperidinyl)-nicotinic acid amide (100 mg, 0.22 mmol), Pd/C (50 mg) and THF (15 mL) is stirred under 50 psi H$_2$-atmosphere for 3 h. The mixture is filtered, and the filtrate is concentrated. HPLC R$_t$=1.28 min (method B). MS m/z: 418 [M+H]$^+$.

(d) N-(trans-4-Trifluoromethyl-cyclohexyl)-2-{2,6-dichloro-3-[(2,2-dimethyl-propionylamino)-methyl]-phenylamino}-5-[4-fluoro-piperidinyl]-3-methyl-3H-imidazo[4,5-b]pyridine-6-carboxamide A mixture of N-(trans-4-trifluoromethyl-cyclohexyl)-6-methylamino-5-amino-2-(4-fluoro-piperidinyl)-nicotinic acid amide (100 mg, 0.22 mmol), N-(2,4-dichloro-3-isothiocyanato-benzyl)-2,2-dimethyl-propionamide (71 mg, 0.22 mmol) and DMF (5.0 mL) is stirred overnight, diluted with EtOAc and washed with water. The organic phase is dried with Na$_2$SO$_4$, filtered and concentrated. Then DMF (5 mL) and DIC (45 μl, 0.29 mmol) is added and it is stirred for 3 h at 80° C. The crude mixture is concentrated, diluted with EtOAc, washed with water, dried with Na$_2$SO$_4$, filtered, concentrated and purified by flash chromatography (silica; DCM->DCM+4% EtOH).

Yield: 70 mg (45%). R$_f$=0.3 (DCM/EtOH 95:5). MS m/z: 700 [M+H]$^+$.

Example 3

N-(trans-4-Trifluoromethyl-cyclohexyl)-2-{2,6-dichloro-3-[(2,2-dimethyl-propionylamino)-methyl]-phenylamino}-5-[4-fluoro-piperidinyl]-3H-imidazo[4,5-b]pyridine-6-carboxamide

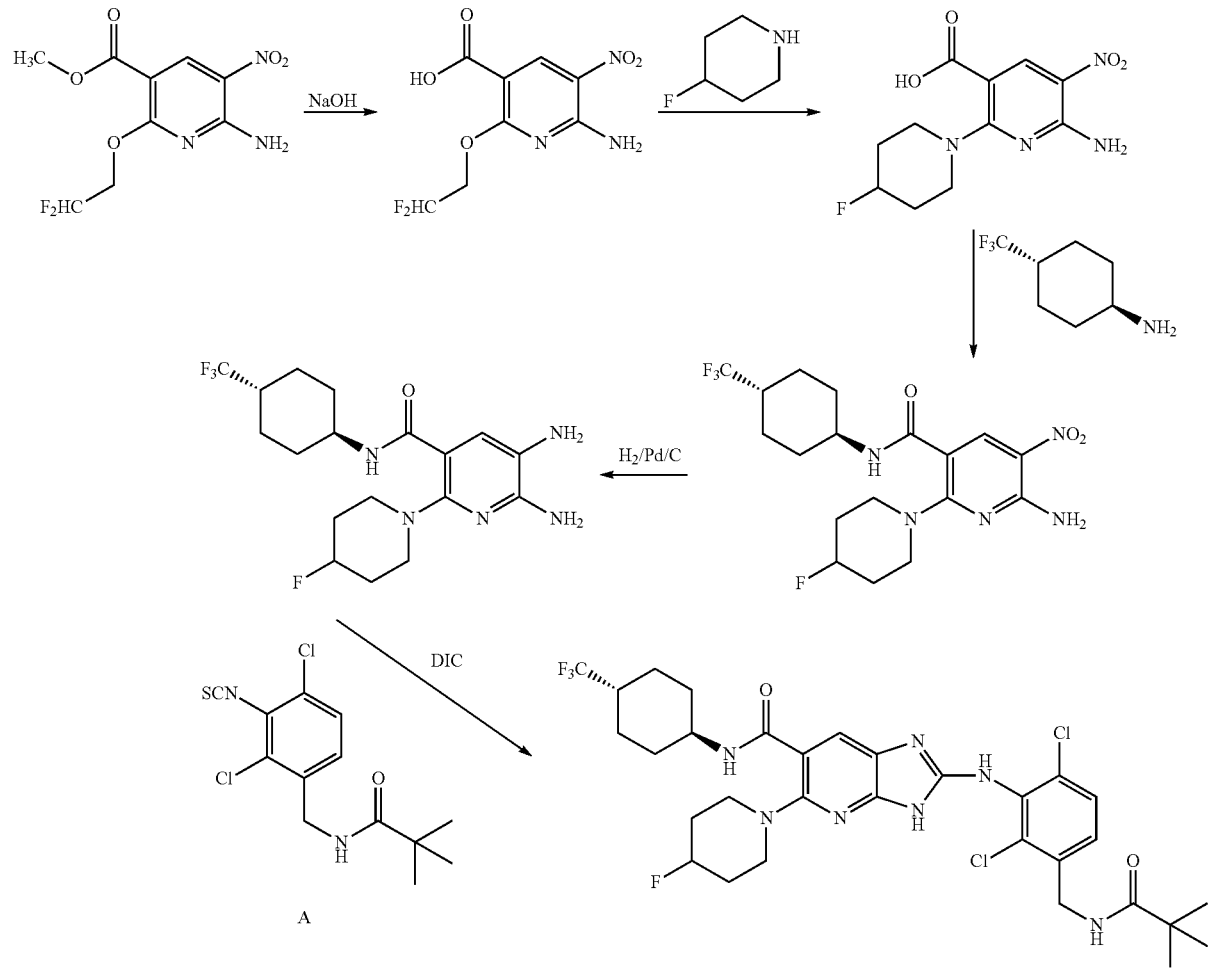

(a) 2-(2,2-Difluoro-ethoxy)-6-amino-5-nitro-nicotinic acid

A mixture of methyl-2-(2,2-difluoro-ethoxy)-6-methylamino-5-nitro-nicotinate (9.1 g, 32 mmol, prepared according to WO2010/34799), THF (100 mL), water (60 mL) and 1N aq. NaOH-solution (60 mL) is stirred for 3 h at rt, then the mixture is concentrated i.vac. The water phase is washed with Et₂O, 60 mL 1N HCl solution is added and the resulting precipitate is collected and dried.

Yield: 7.2 g. HPLC $R_t$=1.39 min (method E).

(b) 6-Amino-5-nitro-2-(4-fluoro-piperidinyl)-nicotinic acid

The subtitle compound is prepared in analogy to 1a from 2-(2,2-difluoro-ethoxy)-6-amino-5-nitro-nicotinic acid and 4-fluoro-piperidine and TEA/Cs₂CO₃.

HPLC $R_t$=1.17 min (method B). MS m/z: 284 [M+H]⁺.

(c) N-(trans-4-Trifluoromethyl-cyclohexyl)-6-amino-5-nitro-2-(4-fluoro-piperidinyl)-nicotinic acid amide The subtitle compound is prepared in analogy to 1b from 6-amino-5-nitro-2-(4-fluoro-piperidinyl)-nicotinic acid, trans-4-trifluoromethyl-cyclohexylamine, TBTU and TEA.

$R_f$=0.43 (DCM/EtOH 95:5). MS m/z: 434 [M+H]⁺.

(d) N-(trans-4-Trifluoromethyl-cyclohexyl)-5,6-diamino-2-(4-fluoro-piperidinyl)-nicotinic acid amide The subtitle compound is prepared in analogy to 2c from N-(trans-4-trifluoromethyl-cyclohexyl)-6-amino-5-nitro-2-(4-fluoro-piperidinyl)-nicotinic acid amide, Pd/C (50 mg) and THF (15 mL) under 50 psi H₂-atmosphere.

HPLC $R_t$=1.21 min (method B). MS m/z: 404 [M+H]⁺.

(e) N-(trans-4-Trifluoromethyl-cyclohexyl)-2-{2,6-dichloro-3-[(2,2-dimethyl-propionylamino)-methyl]-phenylamino}-5-[4-fluoro-piperidinyl]-3H-imidazo[4,5-b]pyridine-6-carboxamide The subtitle compound is prepared in analogy to 2d from N-(trans-4-trifluoromethyl-cyclohexyl)-5,6-diamino-2-(4-fluoro-piperidinyl)-nicotinic acid amide, N-(2,4-dichloro-3-isothiocyanato-benzyl)-2,2-dimethyl-propionamide and DIC.

$R_f$=0.22 (DCM/EtOH 95:5). HPLC $R_t$=1.48 min (method B). MS m/z: 686 [M+H]⁺.

Example 14

N-(trans-4-Trifluoromethyl-cyclohexyl)-2-{2,6-dichloro-5-fluoro-3-[(tert.butoxycarbonylamino)-methyl]-phenylamino}-5-[4-fluoro-piperidinyl]-3H-imidazo[4,5-b]pyridine-6-carboxamide

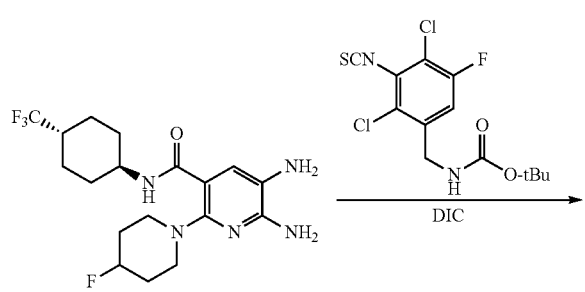

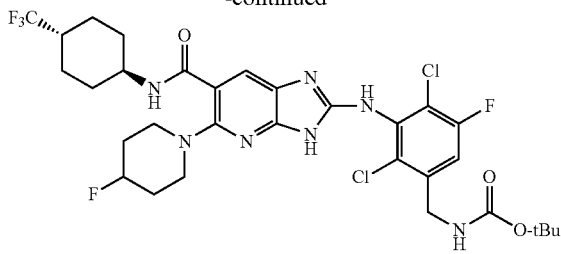

The subtitle compound is prepared in analogy to 2d from N-(trans-4-trifluoromethyl-cyclohexyl)-5,6-diamino-2-(4-fluoro-piperidinyl)-nicotinic acid amide, (2,4-dichloro-5-fluoro-3-isothiocyanato-benzyl)-carbamic acid tert-butyl ester and DIC. The product is purified via prep. HPLC (C-18 stable bond, eluent gradient: water(+0.15% HCOOH)/MeOH 9:1->MeOH).

HPLC $R_t$=2.35 min (method C). MS m/z: 720 [M+H]⁺.

Example 15

N-(trans-4-Trifluoromethyl-cyclohexyl)-2-{2,6-dichloro-5-fluoro-3-[(2,2-dimethyl-propionylamino)-methyl]-phenylamino}-5-[4-fluoro-piperidinyl]-3H-imidazo[4,5-b]pyridine-6-carboxamide

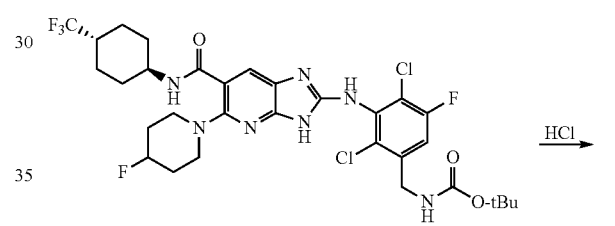

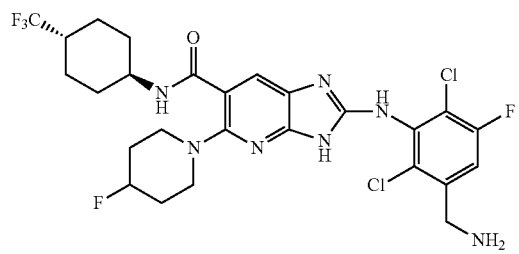

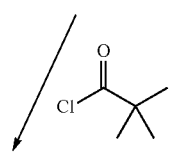

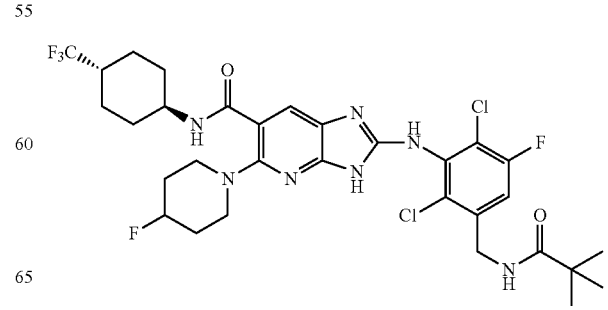

(a) N-(trans-4-Trifluoromethyl-cyclohexyl)-2-{2,6-dichloro-5-fluoro-3-(aminomethyl)-phenylamino}-5-[4-fluoro-piperidinyl]-3H-imidazo[4,5-b]pyridine-6-carboxamide A mixture of N-(trans-4-trifluoromethyl-cyclohexyl)-2-{2,6-dichloro-5-fluoro-3-[(tert.butoxycarbonylamino)-methyl]-phenylamino}-5-[4-fluoro-piperidinyl]-3H-imidazo[4,5-b]pyridine-6-carboxamide (180 mg, 0.250 mmol), 4N HCl in dioxane (5.0 mL) and dioxane (10 mL) is stirred overnight, concentrated, dissolved in water, filtered, basicified with aq

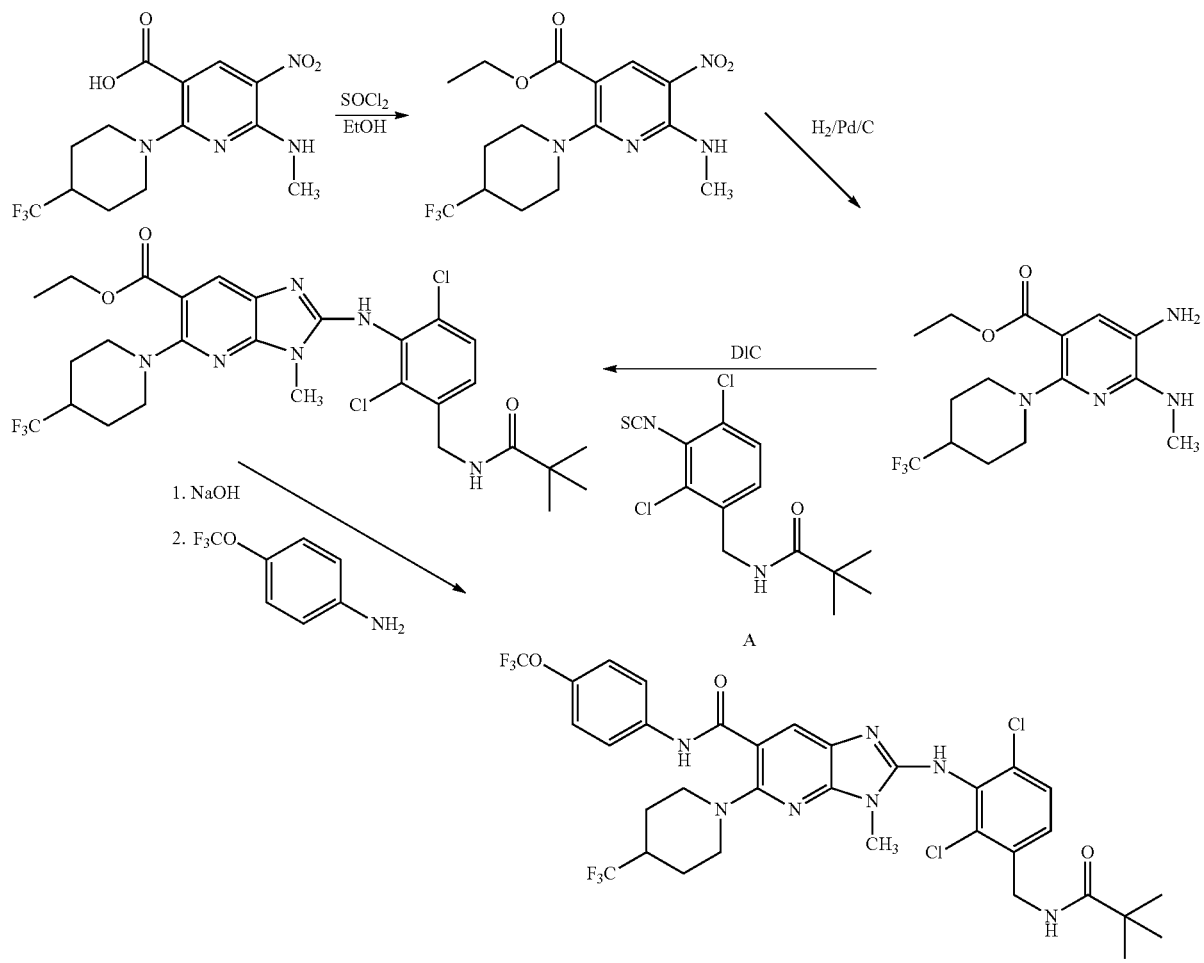

$NH_3$-solution and extracted with DCM. The organic phase is dried with $MgSO_4$, filtered and concentrated.

HPLC $R_t$=1.40 min (method A). MS m/z: 620 [M+H]$^+$.

(b) N-(trans-4-Trifluoromethyl-cyclohexyl)-2-{2,6-dichloro-5-fluoro-3-[(2,2-dimethyl-propionylamino)-methyl]-phenylamino}-5-[4-fluoro-piperidinyl]-3H-imidazo[4,5-b]pyridine-6-carboxamide A mixture of N-(trans-4-trifluoromethyl-cyclohexyl)-2-{2,6-dichloro-5-fluoro-3-(aminomethyl)-phenylamino}-5-[4-fluoro-piperidinyl]-3H-imidazo[4,5-b]pyridine-6-carboxamide (130 mg, 0.210 mmol), pivaloyl chloride (26 µL, 0.21 mmol), TEA (75 mg, 0.74 mmol) and 5 mL THF is stirred for 20 min and diluted with MeOH. The crude product is purified via prep. HPLC (C-18 stable bond, eluent gradient: water(+0.15% HCOOH)/MeOH 9:1->MeOH).

HPLC $R_t$=1.55 min (method A). MS m/z: 704 [M+H]$^+$.

Example 24

N-(4-Trifluoromethoxyphenyl)-2-{2,6-dichloro-3-[(2,2-dimethyl-propionylamino)-methyl]-phenylamino}-5-[4-trifluoromethyl-piperidinyl]-3-methyl-3H-imidazo[4,5-b]pyridine-6-carboxamide (a) 6-Methylamino-5-nitro-2-(4-trifluoromethyl-piperidinyl)-nicotinic acid ethylester A mixture of 6-methylamino-5-nitro-2-(4-trifluoromethyl-piperidinyl)-nicotinic acid (8.50 g, 23.2 mmol), $SOCl_2$ (6.23 mL, 85 mmol), 3 drops of DMF and 200 mL DCM is stirred for 50 min at reflux. The mixture is concentrated, diluted with 80 mL THF and added slowly to 100 mL EtOH at 5-10° C. and it is stirred overnight. TEA is added and the mixture is concentrated, diluted with DCM and washed with water. The organic layer is dried with $MgSO_4$, concentrated and triturated with $Et_2O$ and the sub title compound is isolated as slightly yellow solid.

HPLC $R_t$=1.66 min (method D). MS m/z: 377 [M+H]$^+$.

(b) 6-Methylamino-5-amino-2-(4-trifluoromethyl-piperidinyl)-nicotinic acid ethylester A mixture of 6-methylamino-5-nitro-2-(4-trifluoromethyl-piperidinyl)-nicotinic acid ethylester (6.0 g, 15.9 mmol), Pd/C (800 mg) and EtOH (100 mL) is stirred under 60 psi $H_2$-atmosphere for 6 h. The mixture is filtered, and the filtrate is concentrated. HPLC $R_t$=1.13 min (method A). MS m/z: 347 [M+H]$^+$.

(c) 2-{2,6-Dichloro-3-[(2,2-dimethyl-propionylamino)-methyl]-phenylamino}-5-[4-trifluoromethyl-piperidinyl]-3-methyl-3H-imidazo[4,5-b]pyridine-6-carboxylic acid ethyl ester A mixture of 6-methylamino-5-amino-2-(4-trifluoromethyl-piperidinyl)-nicotinic acid ethylester (2.80 g, 7.92 mmol), N-(2,4-dichloro-3-isothiocyanato-benzyl)-2,2-dimethyl-propionamide (2.76 g, 8.72 mmol) and MeCN (60 mL) is stirred overnight, concentrated and triturated with MeCN and $Et_2O$. The resulting solid is diluted with 60 mL MeCN and DIC (1.06 mL, 6.8 mmol) is added and it is stirred for 3 h at 60° C. The crude mixture is concentrated, diluted with EtOAc, washed with water, dried with $Na_2SO_4$, filtered, concentrated and purified by flash chromatography (silica; PE:EtOAc 3:1->1:1). Yield: 4.04 g. HPLC $R_t$=1.56 min (method D). MS m/z: 629 [M+H]$^+$.

(d) 2-{2,6-Dichloro-3-[(2,2-dimethyl-propionylamino)-methyl]-phenylamino}-5-[4-trifluoromethyl-piperidinyl]-3-methyl-3H-imidazo[4,5-b]pyridine-6-carboxylic acid A mixture of 2-{2,6-dichloro-3-[(2,2-dimethyl-propionylamino)-methyl]-phenylamino}-5-[4-trifluoromethyl-piperidinyl]-3-methyl-3H-imidazo[4,5-b]pyridine-6-carboxylic acid ethyl ester (3.85 g, 6.1 mmol) 2 N NaOH (12 mL, 24 mmol) and 60 mL EtOH is stirred for 4.5 h at 55° C. and overnight at rt. Then the mixture is poured into 150 mL water, the mixture is acidified to pH ~5.5 with aq. $KHSO_4$ and the mixture is concentrated. The resulting precipitate is collected by filtration and dried. Yield: 1.44 g. HPLC $R_t$=1.47 min (method D). MS m/z: 599 [M+H]$^+$.

(e) N-(4-Trifluoromethoxyphenyl)-2-{2,6-dichloro-3-[(2,2-dimethyl-propionylamino)-methyl]-phenylamino}-5-[4-trifluoromethyl-piperidinyl]-3-methyl-3H-imidazo[4,5-b]pyridine-6-carboxamide A mixture of 2-{2,6-dichloro-3-[(2,2-dimethyl-propionylamino)-methyl]-phenylamino}-5-[4-trifluoromethyl-piperidinyl]-3-methyl-3H-imidazo[4,5-b]pyridine-6-carboxylic acid (54 mg, 0.090 mmol), (1-chloro-2-methyl-propenyl)-dimethylamine (0.026 mL, 0.20 mmol) and DCM (2 mL) is stirred for 30 min. This mixture is added to 4-trifluoromethoxyaniline (0.100 mmol) and pyridine (25 μL, 0.32 mmol) in MeCN (1 mL) and it is stirred for 2 h at 40° C. and overnight at 60° C. The mixture is concentrated and the residue is diluted with DMF/water 19/1 (2 mL) and purified via reverse phase HPLC. Yield: 18 mg. HPLC $R_t$=0.645 min (method G). MS m/z: 760 [M+H]$^+$.

Example 25

N-(trans-4-Trifluoromethyl-cyclohexyl)-2-{2,6-dichloro-3-[(2,2-dimethyl-propionylamino)-methyl]-phenylamino}-5-[morpholinyl]-3-(2,2-trifluoroethyl)-3H-imidazo[4,5-b]pyridine-6-carboxamide

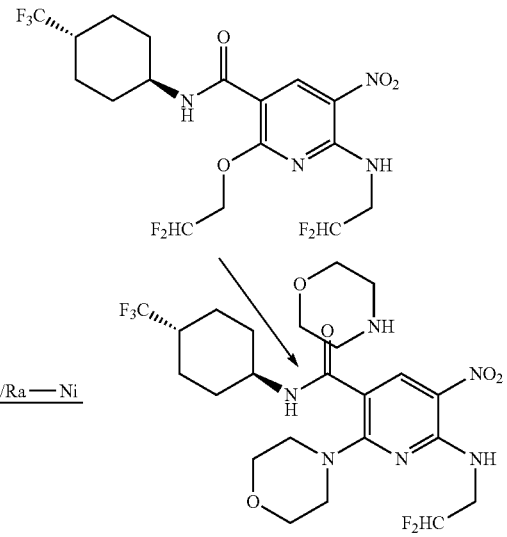

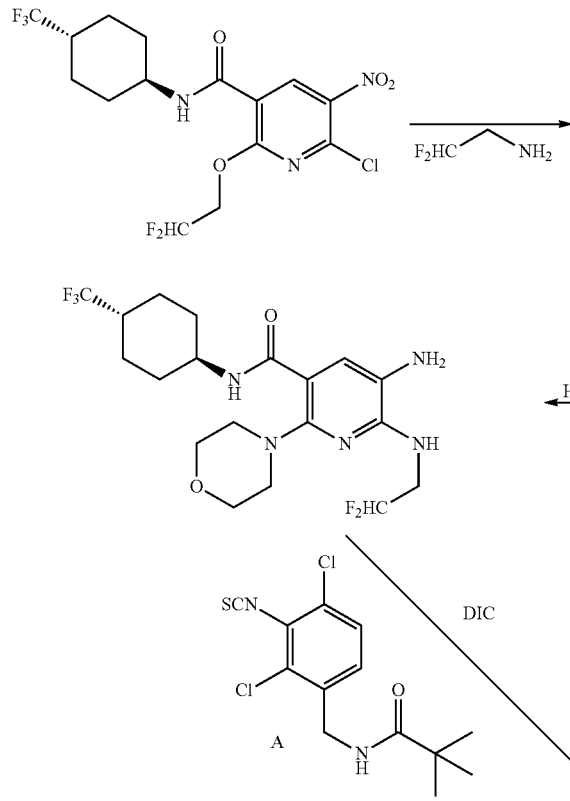

-continued

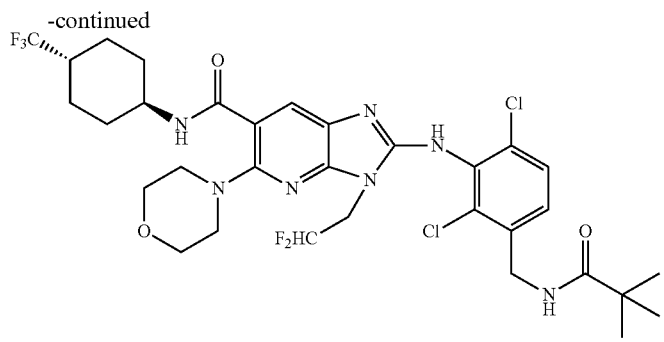

(a) N-(trans-4-Trifluoromethyl-cyclohexyl)-6-(2,2-difluoroethylamino)-5-nitro-2-(2,2-difluoroethoxy)-nicotinic acid amide 2,2-Difluoroethylamine (0.18 mL, 2.53 mmol) is slowly added to a mixture of N-(trans-4-trifluoromethyl-cyclohexyl)-6-chloro-5-nitro-2-(2,2-difluoroethoxy)-nicotinic acid amide (prepared according to WO2010/34799, 1.00 g, 2.3 mmol) and 10 mL THF at 0° C., 2 mL MeOH is added and it is stirred for 20 h. The mixture is concentrated and the solid residue is washed with water and dried. Yield: 0.96 g.

(b) N-(trans-4-Trifluoromethyl-cyclohexyl)-6-(2,2-difluoroethylamino)-5-nitro-2-(morpholinyl)-nicotinic acid amide A mixture of N-(trans-4-trifluoromethyl-cyclohexyl)-6-(2,2-difluoroethylamino)-5-nitro-2-(2,2-difluoroethoxy)-nicotinic acid amide (0.40 g, 0.83 mmol), morpholine (87 mg, 1.0 mmol), K$_2$CO$_3$ (170 mg, 1.24 mmol) and 2.5 mL DMSO is irradiated in a microwave apparatus at 100° C. for 30 min. The mixture is poured into water and the precipitate is collected by filtration and dried. Yield 0.34 g (c) N-(trans-4-Trifluoromethyl-cyclohexyl)-2-{2,6-dichloro-3-[(2,2-dimethyl-propionylamino)-methyl]-phenylamino}-5-[morpholinyl]-3-(2,2-trifluoroethyl)-3H-imidazo[4,5-b]pyridine-6-carboxamide A mixture of N-(trans-4-trifluoromethyl-cyclohexyl)-6-(2,2-difluoroethylamino)-5-nitro-2-(morpholinyl)-nicotinic acid amide (0.34 g, 0.7 mmol), Ra—Ni (0.1 g) and THF (5 mL) is stirred under 50 psi H$_2$-atmosphere for 3 h. The mixture is filtered, and the filtrate is concentrated.

Yield: quantitative.

(d) N-(trans-4-Trifluoromethyl-cyclohexyl)-2-{2,6-dichloro-3-[(2,2-dimethyl-propionylamino)-methyl]-phenylamino}-5-[4-fluoro-piperidinyl]-3-methyl-3H-imidazo[4,5-b]pyridine-6-carboxamide The title compound is prepared in analogy to 2d from N-(trans-4-trifluoromethyl-cyclohexyl)-6-(2,2-difluoroethylamino)-5-amino-2-(morpholinyl)-nicotinic acid amide (0.34 g, 0.75 mmol), N-(2,4-dichloro-3-isothiocyanato-benzyl)-2,2-dimethyl-propionamide (0.27 g, 0.86 mmol) and DIC (0.14 mL). The product is purified via prep. HPLC. MS m/z: 734 [M+H]$^+$. Yield: 5 mg.

Example 30

N-(trans-4-Trifluoromethyl-cyclohexyl)-2-{2,6-dichloro-3-[(2,2-dimethyl-propionylamino)-methyl]-phenylamino}-5-[4-trifluoromethyl-piperidinyl]-3-methyl-3H-imidazo[4,5-b]pyridine-6-carboxamide

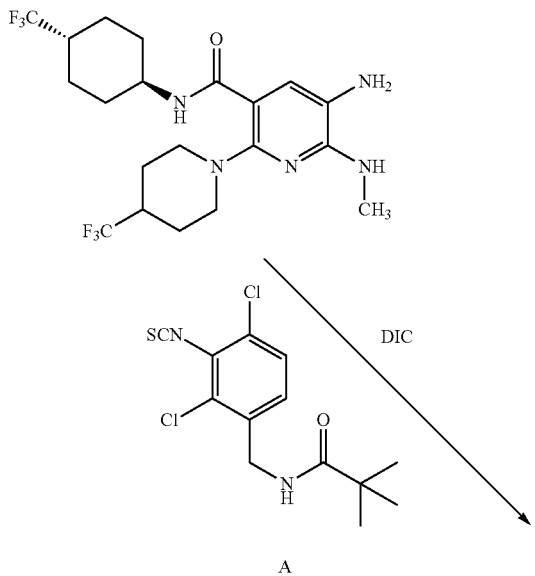

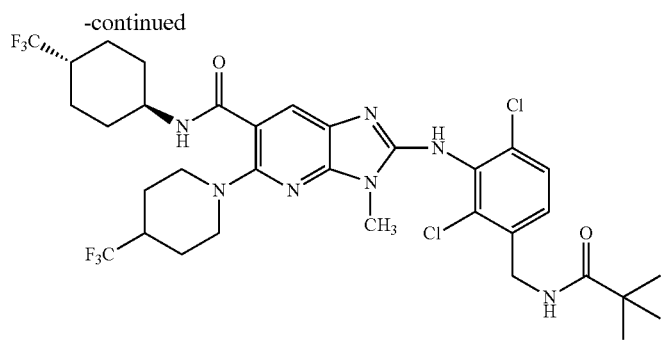

A mixture of N-(trans-4-trifluoromethyl-cyclohexyl)-6-methylamino-5-amino-2-(4-trifluoromethyl-piperidinyl)-nicotinic acid amide (compound Ic; 130 mg, 0.27 mmol), N-(2,4-dichloro-3-isothiocyanato-benzyl)-2,2-dimethyl-propionamide (98 mg, 0.31 mmol) and DMF (3 mL) is stirred for 3 d. Then DIC (57 μl, 0.32 mmol) is added and it is stirred for 1 d. The crude mixture is poured into water and the precipitate is collected by filtration and purified by prep. HPLC. Yield: 90 mg. Melting Point: 185-186° C. MS m/z: 750 [M+H]⁺.

The following intermediates in Table I are precursors for the corresponding examples in Table II (e.g. compound 17c is the precursor of example 17). The intermediates are prepared in a reaction sequence in analogy to the procedures described above (e.g. compound 17c is prepared from 17b which in turn is prepared from 17a following the procedures described in 2a, 2b and 2c).

TABLE I

| Ex. | Structure | remarks | MS* m/z [M + H]⁺ | $R_f$(TLC, silica gel) or $R_t$ [min] (HPLC-method) | Prepared in analogy to example |
|---|---|---|---|---|---|
| 4a | 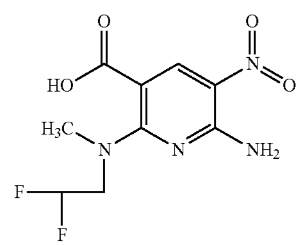 [SMILES: CN(CC(F)F)c1nc(N)c([N+](=O)[O-])cc1C(=O)O] | | 277 | $R_t$: 1.51 min Method E | 3b |
| 4b | 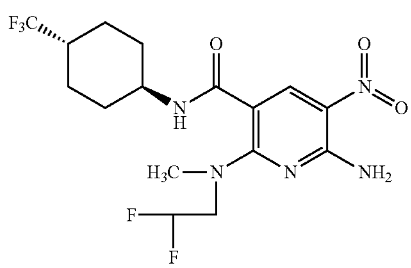 [SMILES: CN(CC(F)F)c1nc(N)c([N+](=O)[O-])cc1C(=O)N[C@H]1CC[C@H](C(F)(F)F)CC1] | | 426 | $R_t$: 2.06 min Method E | 3c |
| 4c | 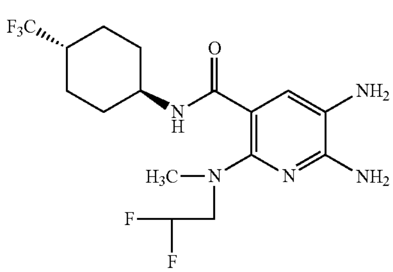 [SMILES: CN(CC(F)F)c1nc(N)c(N)cc1C(=O)N[C@H]1CC[C@H](C(F)(F)F)CC1] | | | | 1c |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-method) | Prepared in analogy to example |
|---|---|---|---|---|---|
| 5a | 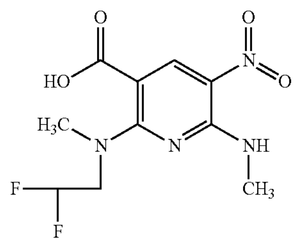 [SMILES: CNc1nc(N(C)CC(F)F)c(C(=O)O)cc1[N+](=O)[O-]] | | 291 | R$_t$: 1.71 min Method E | 1a |
| 5b | 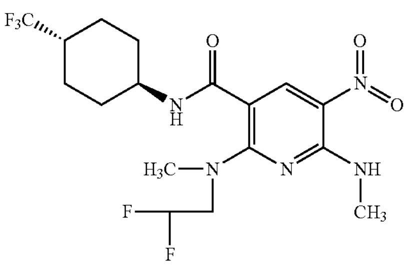 [SMILES: CNc1nc(N(C)CC(F)F)c(C(=O)N[C@H]2CC[C@H](C(F)(F)F)CC2)cc1[N+](=O)[O-]] | | 440 | R$_t$: 2.15 min Method E | 1b |
| 5c | 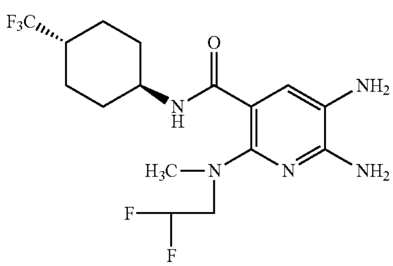 [SMILES: CN(CC(F)F)c1nc(N)c(N)cc1C(=O)N[C@H]1CC[C@H](C(F)(F)F)CC1] | | 410 | R$_t$: 1.96 min Method E | 1c |
| 6a | 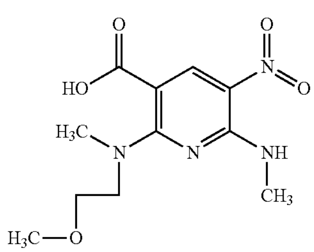 [SMILES: CNc1nc(N(C)CCOC)c(C(=O)O)cc1[N+](=O)[O-]] | | 285 | | 1a |
| 6b | 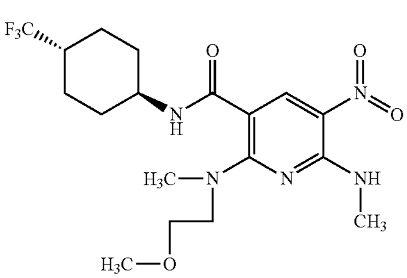 [SMILES: CNc1nc(N(C)CCOC)c(C(=O)N[C@H]2CC[C@H](C(F)(F)F)CC2)cc1[N+](=O)[O-]] | | 434 | | 1b |

TABLE I-continued

Intermediates (prepared in analogy to the indicated procedure)

| Ex. | Structure | remarks | MS* m/z [M + H]+ | $R_f$ (TLC, silica gel) or $R_t$ [min] (HPLC-method) | Prepared in analogy to example |
|---|---|---|---|---|---|
| 6c | 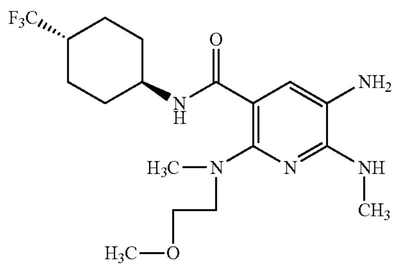 [SMILES: CNc1nc(N(C)CCOC)c(C(=O)N[C@H]2CC[C@H](C(F)(F)F)CC2)cc1N] | | 404 | | 1c |
| 7a | 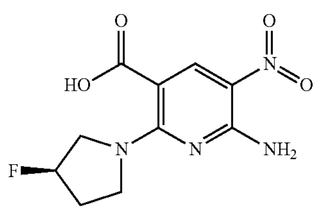 [SMILES: Nc1nc(N2CC[C@@H](F)C2)c(C(=O)O)cc1[N+](=O)[O-]] | | 271 | $R_t$: 1.12 min Method B | 1a |
| 7b | 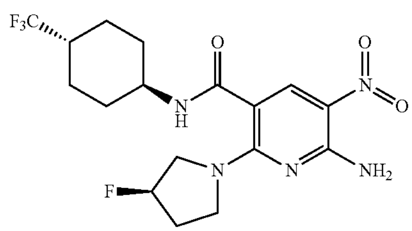 [SMILES: Nc1nc(N2CC[C@@H](F)C2)c(C(=O)N[C@H]2CC[C@H](C(F)(F)F)CC2)cc1[N+](=O)[O-]] | | 420 | $R_F$ = 0.38 DCM:EtOH 19:1 | 1b |
| 7c | 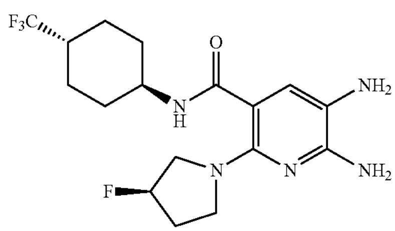 [SMILES: Nc1cc(C(=O)N[C@H]2CC[C@H](C(F)(F)F)CC2)c(N2CC[C@@H](F)C2)nc1N] | | 390 | $R_t$: 1.14 min Method B | 1c |
| 9a | 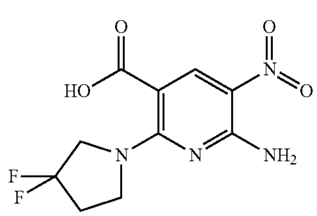 [SMILES: Nc1nc(N2CCC(F)(F)C2)c(C(=O)O)cc1[N+](=O)[O-]] | | | $R_t$: 1.54 min Method E | 1a |
| 9b | 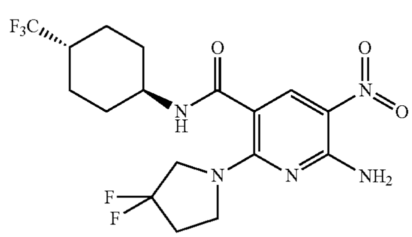 [SMILES: Nc1nc(N2CCC(F)(F)C2)c(C(=O)N[C@H]2CC[C@H](C(F)(F)F)CC2)cc1[N+](=O)[O-]] | | | $R_t$: 1.40 min Method B | 1b |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC-method) | Prepared in analogy to example |
|---|---|---|---|---|---|
| 9c | 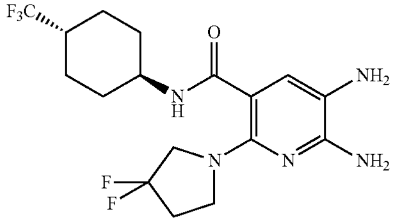 [SMILES: Nc1cc(C(=O)N[C@H]2CC[C@H](C(F)(F)F)CC2)c(N2CCC(F)(F)C2)nc1N] | | | R$_t$: 1.24 min Method B | 1c |
| 10a | 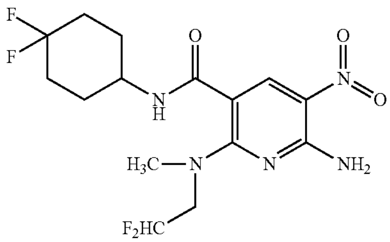 [SMILES: CN(CC(F)F)c1nc(N)c([N+](=O)[O-])cc1C(=O)NC1CCC(F)(F)CC1] | | 394 | R$_t$: 1.87 min Method E | 1b |
| 10b | 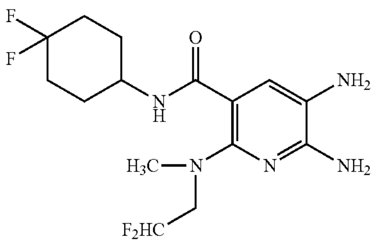 [SMILES: CN(CC(F)F)c1nc(N)c(N)cc1C(=O)NC1CCC(F)(F)CC1] | | 364 | R$_t$: 1.55 min Method E | 1c |
| 11a | 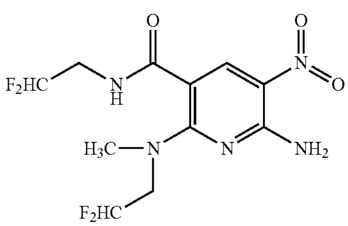 [SMILES: CN(CC(F)F)c1nc(N)c([N+](=O)[O-])cc1C(=O)NCC(F)F] | | 340 | R$_t$: 1.60 min Method E | 1b |
| 11b | 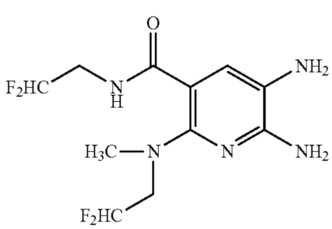 [SMILES: CN(CC(F)F)c1nc(N)c(N)cc1C(=O)NCC(F)F] | | 310 | R$_t$: 1.20 min Method E | 1c |
| 12a | 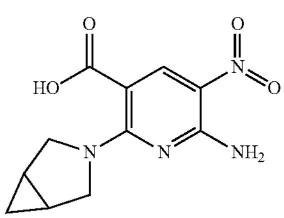 [SMILES: Nc1nc(N2CC3CC3C2)c(C(=O)O)cc1[N+](=O)[O-]] | | | R$_t$: 1.51 min Method E | 1a |

TABLE I-continued

Intermediates (prepared in analogy to the indicated procedure)

| Ex. | Structure | remarks | MS* m/z [M + H]+ | R_f (TLC, silica gel) or R_t [min] (HPLC-method) | Prepared in analogy to example |
|---|---|---|---|---|---|
| 12b | 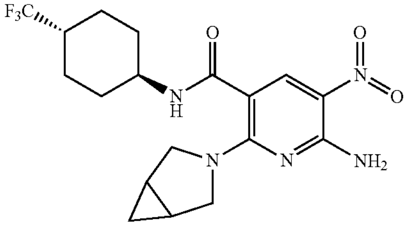 [SMILES: Nc1nc(N2CC3CC3C2)c(C(=O)N[C@H]2CC[C@H](C(F)(F)F)CC2)cc1[N+](=O)[O-]] | | 414 | R_t: 2.03 min Method E | 1b |
| 12c | 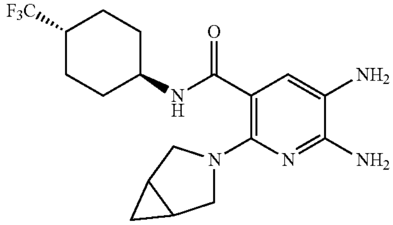 [SMILES: Nc1cc(C(=O)N[C@H]2CC[C@H](C(F)(F)F)CC2)c(N2CC3CC3C2)nc1N] | | | R_t: 1.22 min Method B | 1c |
| 16a | 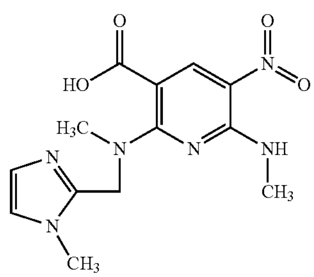 [SMILES: CNc1nc(N(C)Cc2nccn2C)c(C(=O)O)cc1[N+](=O)[O-]] | | 321 | R_t: 0.73 min Method A | 2a |
| 16b | 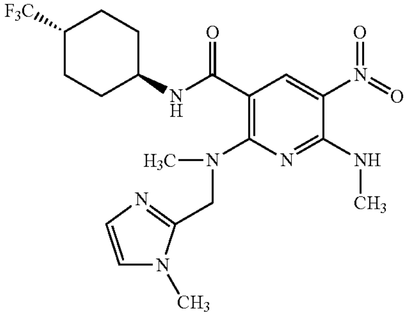 [SMILES: CNc1nc(N(C)Cc2nccn2C)c(C(=O)N[C@H]2CC[C@H](C(F)(F)F)CC2)cc1[N+](=O)[O-]] | | | | 2b |
| 16c | 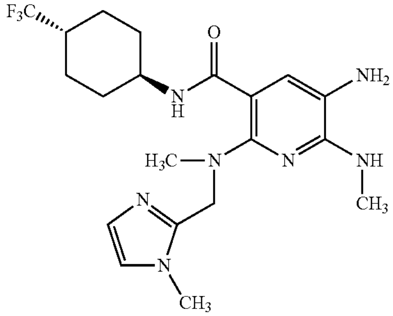 | | 440 | R_t: 1.02 min Method A | 2c |

TABLE I-continued

Intermediates (prepared in analogy to the indicated procedure)

| Ex. | Structure | remarks | MS* m/z [M + H]+ | R_f (TLC, silica gel) or R_t [min] (HPLC-method) | Prepared in analogy to example |
|---|---|---|---|---|---|
| 17a | 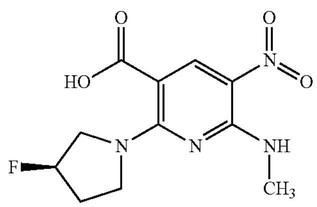 | | 285 | R_t: 1.29 min Method D | 2a |
| 17b | 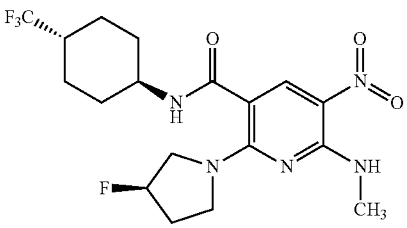 [SMILES: CNc1nc(N2CC[C@@H](F)C2)c(C(=O)N[C@H]2CC[C@H](C(F)(F)F)CC2)cc1[N+](=O)[O-]] | | 434 | R_t: 1.51 min Method D | 2b |
| 17c | 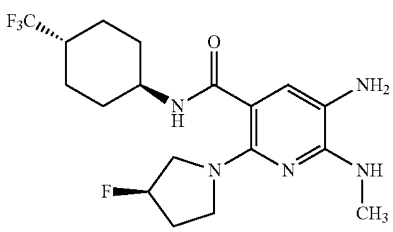 [SMILES: CNc1nc(N2CC[C@@H](F)C2)c(C(=O)N[C@H]2CC[C@H](C(F)(F)F)CC2)cc1N] | | | | 2c |
| 20a | 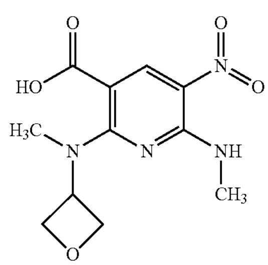 [SMILES: CNc1nc(N(C)C2COC2)c(C(=O)O)cc1[N+](=O)[O-]] | | 283 | R_t: 1.14 min Method F | 2a |
| 20b | 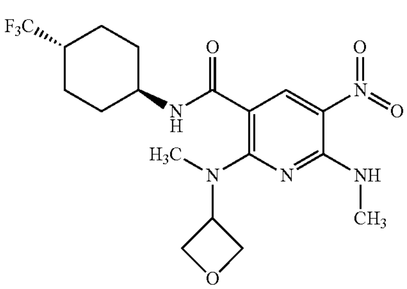 [SMILES: CNc1nc(N(C)C2COC2)c(C(=O)N[C@H]2CC[C@H](C(F)(F)F)CC2)cc1[N+](=O)[O-]] | | 432 | R_t: 1.43 min Method F | 2b |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC-method) | Prepared in analogy to example |
|---|---|---|---|---|---|
| 20c | (structure) | | 402 | R$_t$: 1.26 min Method D | 2c |
| 21a | (structure) | | 322 | R$_t$: 0.86 min Method D | 2a |
| 21b | (structure) | | 471 | R$_t$: 1.3 min Method D | 2b |
| 21c | (structure) | | 441 | R$_t$: 1.37 min Method F | 2c |
| 22a | (structure) | | 311 | R$_t$: 1.24 min Method D | 2a |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC-method) | Prepared in analogy to example |
|---|---|---|---|---|---|
| 22b | (structure) | | 460 | R$_t$: 1.48 min Method F | 2b |
| 22c | (structure) | | 430 | R$_t$: 1.20 min Method D | 2c |
| 23a | (structure) | | 306 | | 2a |
| 23b | (structure) | | 456 | | 2b |
| 23c | (structure) | | 426 | R$_t$: 1.36 min Method D | 2c |

TABLE I-continued

Intermediates (prepared in analogy to the indicated procedure)

| Ex. | Structure | remarks | MS* m/z [M + H]+ | R_f (TLC, silica gel) or R_t [min] (HPLC-method) | Prepared in analogy to example |
|---|---|---|---|---|---|
| 26a | 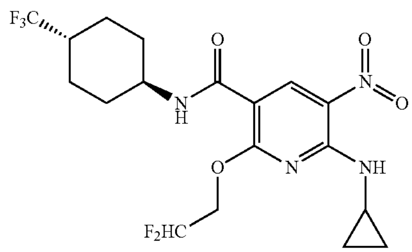 [SMILES: O=C(N[C@H]1CC[C@H](C(F)(F)F)CC1)c1cc([N+](=O)[O-])c(NC2CC2)nc1OCC(F)F] | | | | 25a |
| 26b | 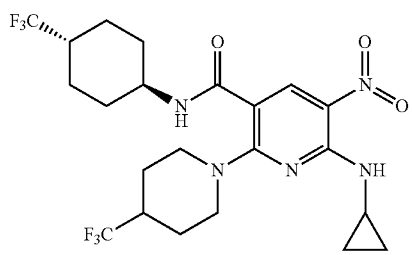 [SMILES: O=C(N[C@H]1CC[C@H](C(F)(F)F)CC1)c1cc([N+](=O)[O-])c(NC2CC2)nc1N1CCC(C(F)(F)F)CC1] | | | | 25b |
| 26c | 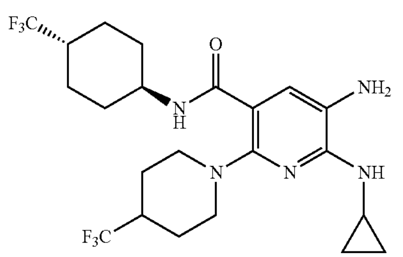 [SMILES: Nc1cc(C(=O)N[C@H]2CC[C@H](C(F)(F)F)CC2)c(N2CCC(C(F)(F)F)CC2)nc1NC1CC1] | | | | 25c |
| 27a | 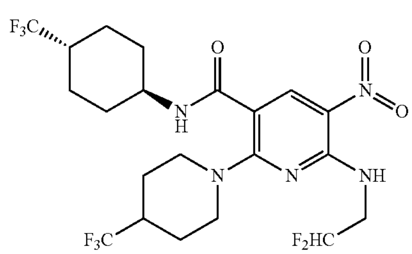 [SMILES: O=C(N[C@H]1CC[C@H](C(F)(F)F)CC1)c1cc([N+](=O)[O-])c(NCC(F)F)nc1N1CCC(C(F)(F)F)CC1] | | | | 25b |
| 27b | 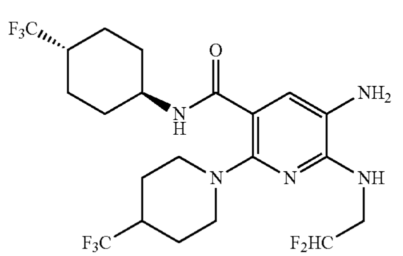 [SMILES: Nc1cc(C(=O)N[C@H]2CC[C@H](C(F)(F)F)CC2)c(N2CCC(C(F)(F)F)CC2)nc1NCC(F)F] | | | | 25c |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-method) | Prepared in analogy to example |
|---|---|---|---|---|---|
| 28a | (structure) | | | | 25a |
| 28b | (structure) | | | | 25b |
| 28c | (structure) | | | | 25c |
| 29a | (structure) | | | | 25a |

TABLE I-continued

Intermediates (prepared in analogy to the indicated procedure)

| Ex. | Structure | remarks | MS* m/z [M + H]+ | R_f (TLC, silica gel) or R_t [min] (HPLC-method) | Prepared in analogy to example |
|---|---|---|---|---|---|
| 29b | (structure) | | | | 25b |
| 29c | (structure) | | | | 25c |

The following examples in Table II are prepared in analogy to the methods described above.

TABLE II examples

| Ex. | Structure | Formula/ Mw. | MS* m/z [M + H]+ | R_F (TLC, silica gel) or R_t [min] (HPLC-method) | Prepared in analogy to example |
|---|---|---|---|---|---|
| 4 | (structure) | $C_{29}H_{34}Cl_2F_5N_7O_2$ 678.52 | 678 | R_t: 2.02 min Method E | 3e |

TABLE II-continued examples

| Ex. | Structure | Formula/ Mw. | MS* m/z [M + H]+ | R_F (TLC, silica gel) or R_t [min] (HPLC-method) | Prepared in analogy to example |
|---|---|---|---|---|---|
| 5 | 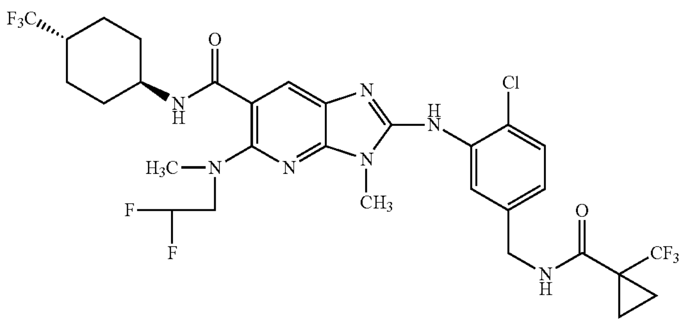 [SMILES: CN(CC(F)F)c1nc2c(cc1C(=O)N[C@H]1CC[C@H](C(F)(F)F)CC1)nc(Nc1cc(CNC(=O)C3(C(F)(F)F)CC3)ccc1Cl)n2C] | $C_{30}H_{32}Cl F_8N_7O_2$ 710.06 | 710 | R_t: 2.29 min Method E | 1d |
| 6 | 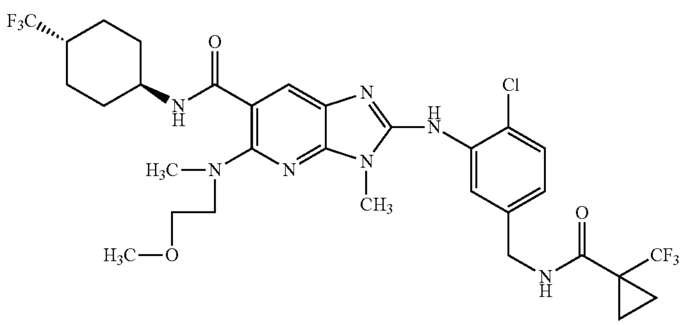 [SMILES: COCCN(C)c1nc2c(cc1C(=O)N[C@H]1CC[C@H](C(F)(F)F)CC1)nc(Nc1cc(CNC(=O)C3(C(F)(F)F)CC3)ccc1Cl)n2C] | $C_{31}H_{36}Cl F_6N_7O_3$ 704.11 | 704 | | 1d |
| 7 | 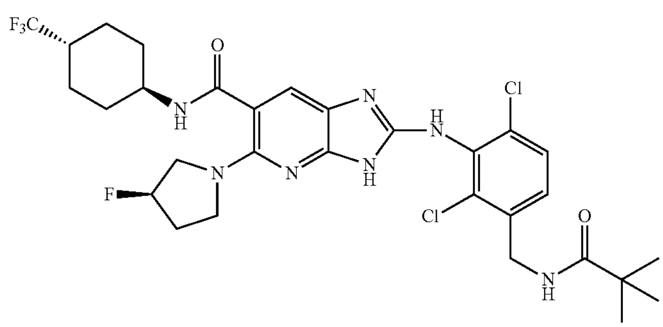 [SMILES: CC(C)(C)C(=O)NCc1ccc(Cl)c(Nc2nc3cc(C(=O)N[C@H]4CC[C@H](C(F)(F)F)CC4)c(N4CC[C@@H](F)C4)nc3[nH]2)c1Cl] | $C_{30}H_{35}Cl_2 F_4N_7O_2$ 672.54 | 672 | R_F = 0.17 DCM:EtOH 19:1 | 1d |
| 8 | 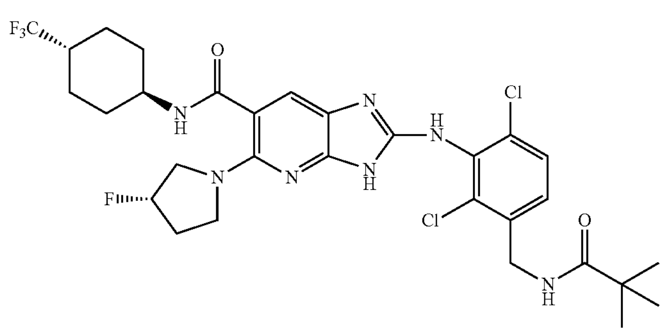 [SMILES: CC(C)(C)C(=O)NCc1ccc(Cl)c(Nc2nc3cc(C(=O)N[C@H]4CC[C@H](C(F)(F)F)CC4)c(N4CC[C@H](F)C4)nc3[nH]2)c1Cl] | $C_{30}H_{35}Cl_2 F_4N_7O_2$ 672.54 | 672 | R_F = 0.17 DCM:EtOH 19:1 | 7 |

TABLE II-continued examples

| Ex. | Structure | Formula/ Mw. | MS* m/z [M + H]+ | R_F (TLC, silica gel) or R_t [min] (HPLC-method) | Prepared in analogy to example |
|---|---|---|---|---|---|
| 9 | 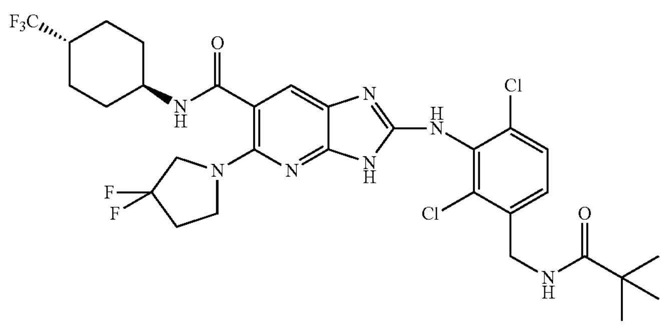 [SMILES: CC(C)(C)C(=O)NCc1ccc(Cl)c(Nc2nc3cc(C(=O)N[C@H]4CC[C@H](C(F)(F)F)CC4)c(N4CCC(F)(F)C4)nc3[nH]2)c1Cl] | $C_{30}H_{34}Cl_2F_5N_7O_2$ 690.53 | 690 | $R_t$: 1.43 min Method B | 1d |
| 10 | 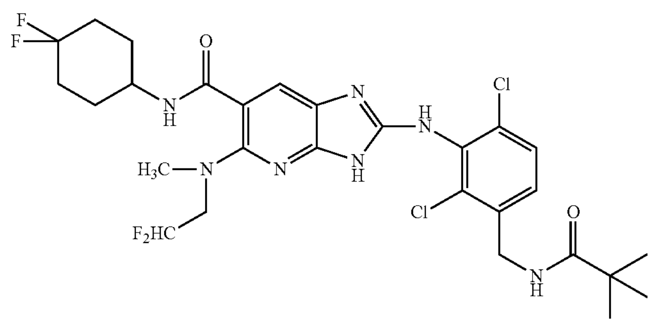 [SMILES: CN(CC(F)F)c1nc2[nH]c(Nc3c(Cl)ccc(CNC(=O)C(C)(C)C)c3Cl)nc2cc1C(=O)NC1CCC(F)(F)CC1] | $C_{28}H_{33}Cl_2F_4N_7O_2$ 646.51 | 646 | $R_t$: 1.89 min Method E | 1d |
| 11 | 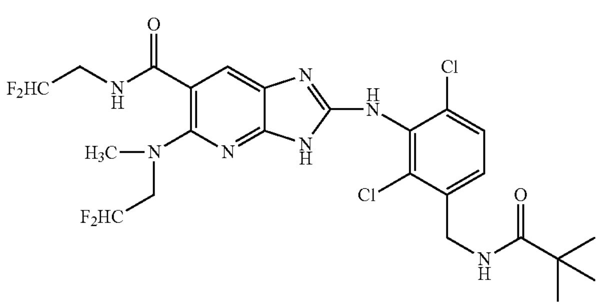 [SMILES: CN(CC(F)F)c1nc2[nH]c(Nc3c(Cl)ccc(CNC(=O)C(C)(C)C)c3Cl)nc2cc1C(=O)NCC(F)F] | $C_{24}H_{27}Cl_2F_4N_7O_2$ 592.42 | 592 | $R_t$: 1.74 min Method E | 1d |
| 12 | 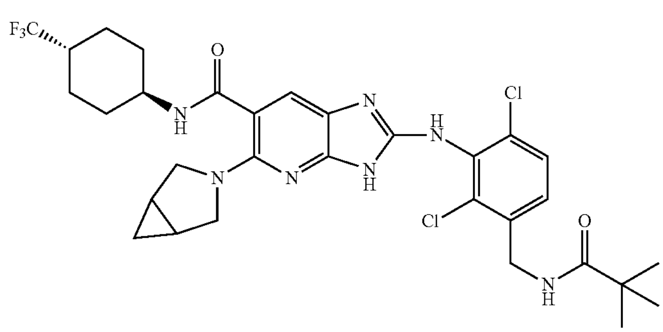 [SMILES: CC(C)(C)C(=O)NCc1ccc(Cl)c(Nc2nc3cc(C(=O)N[C@H]4CC[C@H](C(F)(F)F)CC4)c(N4CC5CC5C4)nc3[nH]2)c1Cl] | $C_{31}H_{36}Cl_2F_3N_7O_2$ 666.56 | 666 | $R_t$: 1.40 min Method B | 1d |

TABLE II-continued examples

| Ex. | Structure | Formula/ Mw. | MS* m/z [M + H]+ | R_F (TLC, silica gel) or R_t [min] (HPLC-method) | Prepared in analogy to example |
|---|---|---|---|---|---|
| 16 | 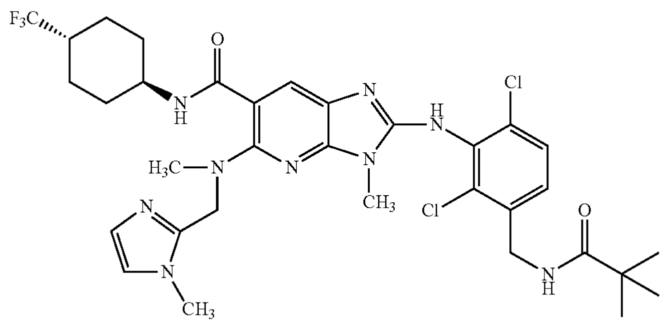 | $C_{33}H_{40}Cl_2F_3N_9O_2$ 722.63 | 722 | $R_t$: 1.32 min Method A | 2d |
| 17 | 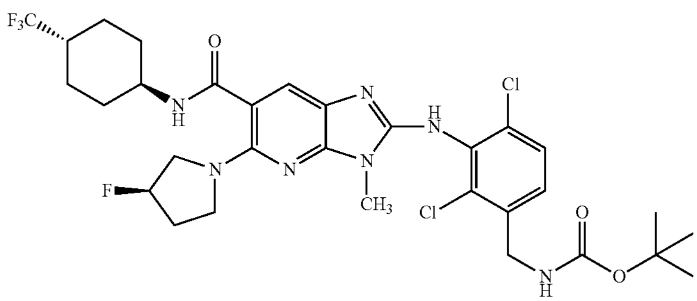 [SMILES: Cn1c(Nc2c(Cl)ccc(CNC(=O)OC(C)(C)C)c2Cl)nc2cc(C(=O)N[C@H]3CC[C@H](C(F)(F)F)CC3)c(N3CC[C@@H](F)C3)nc21] | $C_{31}H_{37}Cl_2F_4N_7O_3$ 702.57 | 702 | $R_t$: 1.60 min Method D | 2d |
| 18 | 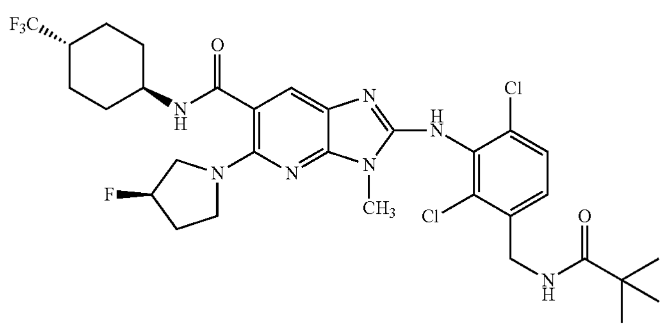 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC[C@@H](F)C3)nc21] | $C_{31}H_{37}Cl_2F_4N_7O_2$ 686.57 | 686 | $R_t$: 1.65 min Method D | 15a/b Educt 17 |
| 19 | 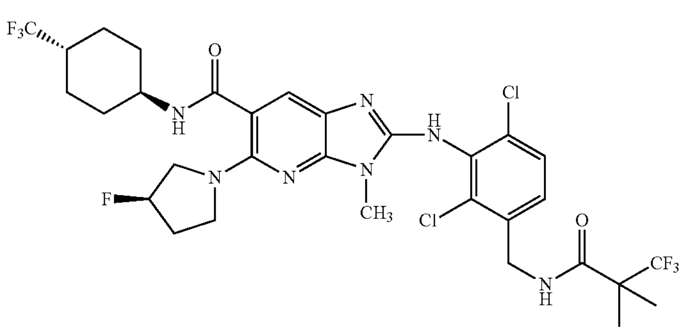 [SMILES: Cn1c(Nc2c(Cl)ccc(CNC(=O)C(C)(C)C(F)(F)F)c2Cl)nc2cc(C(=O)N[C@H]3CC[C@H](C(F)(F)F)CC3)c(N3CC[C@@H](F)C3)nc21] | $C_{31}H_{34}Cl_2F_7N_7O_2$ 740.55 | 740 | $R_t$: 1.66 min Method D | 15a/b Educt 17 |

TABLE II-continued examples

| Ex. | Structure | Formula/ Mw. | MS* m/z [M + H]+ | R_F (TLC, silica gel) or R_t [min] (HPLC-method) | Prepared in analogy to example |
|---|---|---|---|---|---|
| 20 | 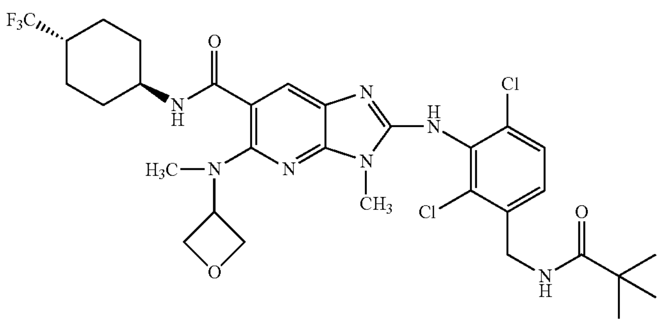 [SMILES: CN(c1nc2c(cc1C(=O)N[C@H]1CC[C@H](C(F)(F)F)CC1)nc(Nc1c(Cl)ccc(CNC(=O)C(C)(C)C)c1Cl)n2C)C1COC1] | $C_{31}H_{38}Cl_2F_3N_7O_3$ 684.58 | 684 | $R_t$: 1.64 min Method F | 2d |
| 21 | 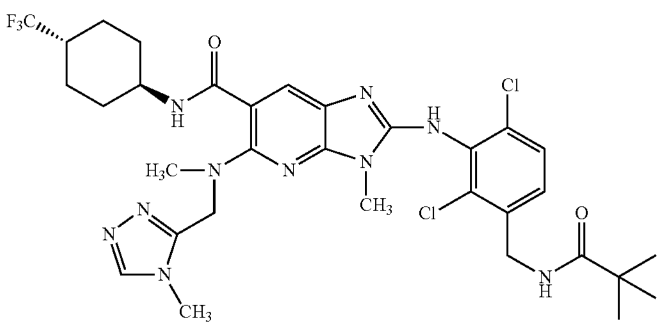 [SMILES: CN(Cc1nncn1C)c1nc2c(cc1C(=O)N[C@H]1CC[C@H](C(F)(F)F)CC1)nc(Nc1c(Cl)ccc(CNC(=O)C(C)(C)C)c1Cl)n2C] | $C_{32}H_{39}Cl_2F_3N_{10}O_2$ 723.62 | 723 | $R_t$: 1.55 min Method F | 2d |
| 22 | 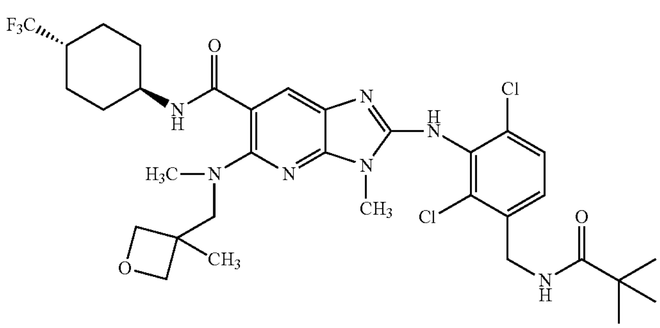 [SMILES: CN(CC1(C)COC1)c1nc2c(cc1C(=O)N[C@H]1CC[C@H](C(F)(F)F)CC1)nc(Nc1c(Cl)ccc(CNC(=O)C(C)(C)C)c1Cl)n2C] | $C_{33}H_{42}Cl_2F_3N_7O_3$ 712.63 | 712 | $R_t$: 1.67 min Method F | 2d |
| 23 | 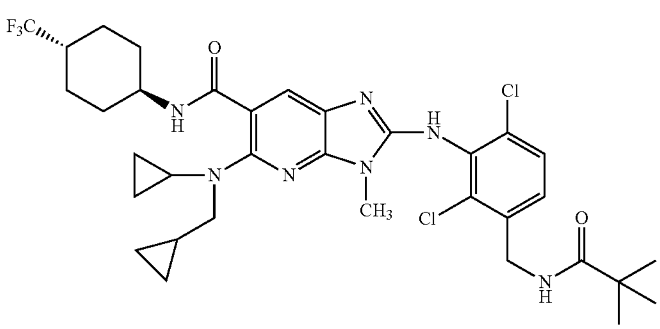 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N(CC3CC3)C3CC3)nc21] | $C_{34}H_{42}Cl_2F_3N_7O_2$ 708.64 | 708 | $R_t$: 1.79 min Method F | 2d |

TABLE II-continued examples

| Ex. | Structure | Formula/ Mw. | MS* m/z [M + H]+ | R_F (TLC, silica gel) or R_t [min] (HPLC-method) | Prepared in analogy to example |
|---|---|---|---|---|---|
| 26 | 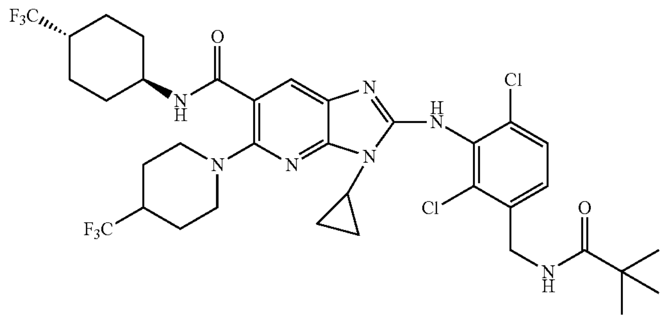 [SMILES: CC(C)(C)C(=O)NCc1ccc(Cl)c(Nc2nc3cc(C(=O)N[C@H]4CC[C@H](C(F)(F)F)CC4)c(N4CCC(C(F)(F)F)CC4)nc3n2C2CC2)c1Cl] | C$_{35}$H$_{41}$Cl$_2$F$_6$N$_7$O$_2$ 776.65 | 776 | Melting point: 198-200° C. | 2d |
| 27 | 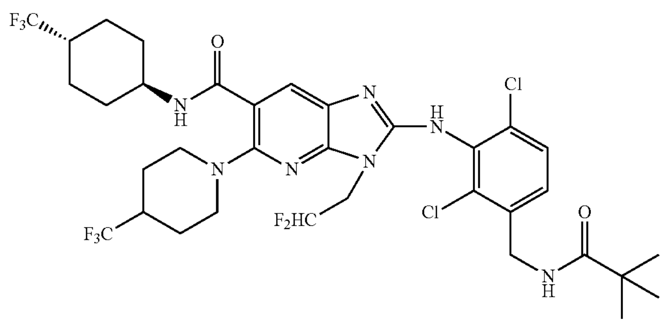 [SMILES: CC(C)(C)C(=O)NCc1ccc(Cl)c(Nc2nc3cc(C(=O)N[C@H]4CC[C@H](C(F)(F)F)CC4)c(N4CCC(C(F)(F)F)CC4)nc3n2CC(F)F)c1Cl] | C$_{34}$H$_{39}$Cl$_2$F$_8$N$_7$O$_2$ 800.62 | 800 | Melting point: 172-174° C. | 2d |
| 28 | 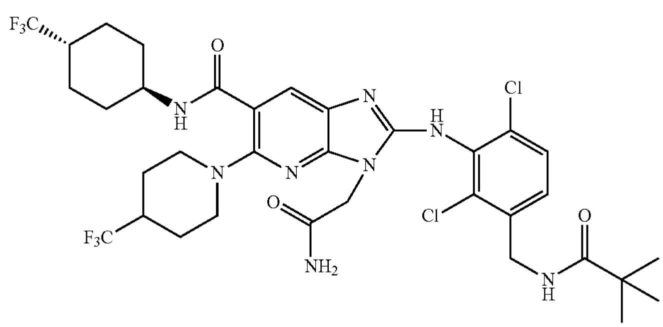 [SMILES: CC(C)(C)C(=O)NCc1ccc(Cl)c(Nc2nc3cc(C(=O)N[C@H]4CC[C@H](C(F)(F)F)CC4)c(N4CCC(C(F)(F)F)CC4)nc3n2CC(N)=O)c1Cl] | C$_{34}$H$_{40}$Cl$_2$F$_6$N$_8$O$_3$ 793.65 | 793 | Melting point: 189-191° C. | 2d |
| 29 | 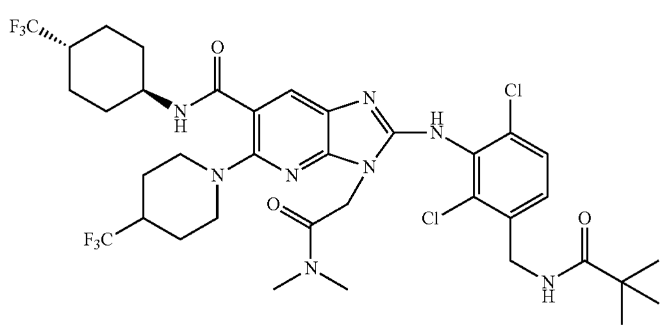 [SMILES: CN(C)C(=O)Cn1c(Nc2c(Cl)ccc(CNC(=O)C(C)(C)C)c2Cl)nc2cc(C(=O)N[C@H]3CC[C@H](C(F)(F)F)CC3)c(N3CCC(C(F)(F)F)CC3)nc21] | C$_{36}$H$_{44}$Cl$_2$F$_6$N$_8$O$_3$ 621.29 | 821 | | 2d |

TABLE II-continued

| Ex. | Structure | Formula/ Mw. | MS* m/z [M + H]+ | R_F (TLC, silica gel) or R_t [min] (HPLC-method) | Prepared in analogy to example |
|---|---|---|---|---|---|
| 31 | 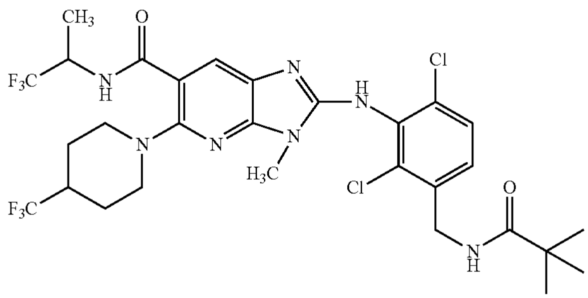 [SMILES: CC(NC(=O)c1cc2nc(Nc3c(Cl)ccc(CNC(=O)C(C)(C)C)c3Cl)n(C)c2nc1N1CCC(C(F)(F)F)CC1)C(F)(F)F] | $C_{29}H_{33}Cl_2F_6N_7O_2$ 696.52 | 696 | R_t: 0.605 min Method G | 24e |
| 32 | 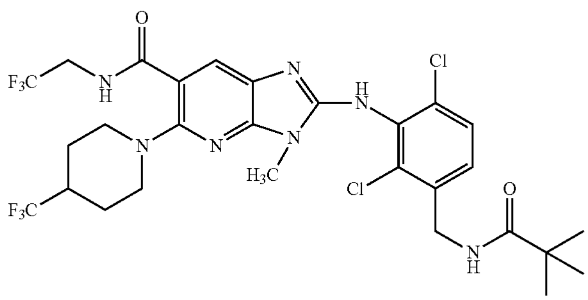 [SMILES: Cn1c(Nc2c(Cl)ccc(CNC(=O)C(C)(C)C)c2Cl)nc2cc(C(=O)NCC(F)(F)F)c(N3CCC(C(F)(F)F)CC3)nc21] | $C_{28}H_{31}Cl_2F_6N_7O_2$ 682.49 | 683 | Rt: 0.590 min Method G | 24e |
| 33 | 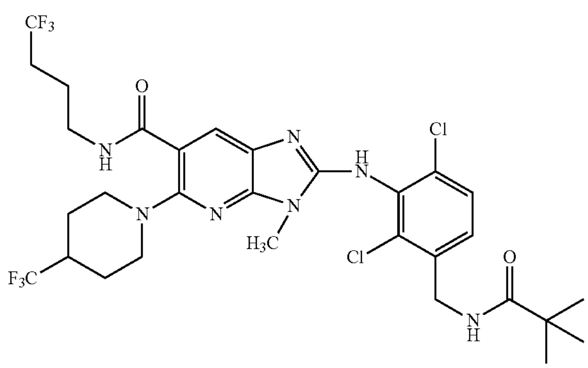 [SMILES: Cn1c(Nc2c(Cl)ccc(CNC(=O)C(C)(C)C)c2Cl)nc2cc(C(=O)NCCCC(F)(F)F)c(N3CCC(C(F)(F)F)CC3)nc21] | $C_{30}H_{35}Cl_2F_6N_7O_2$ 710.55 | 711 | Rt: 0.593 min Method G | 24e |
| 34 | 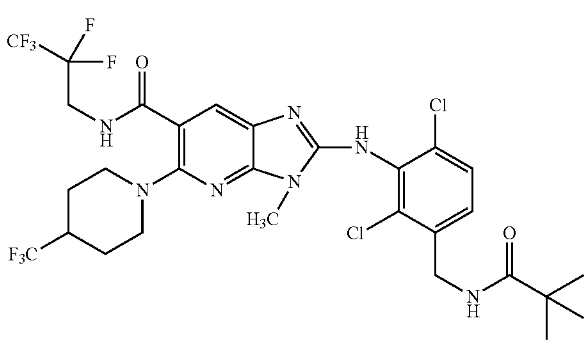 [SMILES: Cn1c(Nc2c(Cl)ccc(CNC(=O)C(C)(C)C)c2Cl)nc2cc(C(=O)NCC(F)(F)C(F)(F)F)c(N3CCC(C(F)(F)F)CC3)nc21] | $C_{29}H_{31}Cl_2F_8N_7O_2$ 732.50 | 732 | Rt: 0.612 min Method G | 24e |

TABLE II-continued

| Ex. | Structure | Formula/Mw. | MS* m/z [M + H]+ | R_F (TLC, silica gel) or R_t [min] (HPLC-method) | Prepared in analogy to example |
|---|---|---|---|---|---|
| 35 | 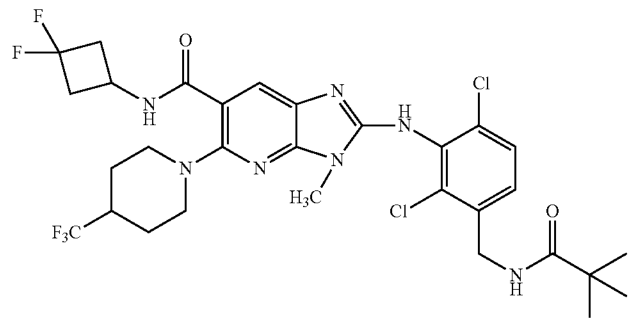 [SMILES: Cn1c(Nc2c(Cl)ccc(CNC(=O)C(C)(C)C)c2Cl)nc2cc(C(=O)NC3CC(F)(F)C3)c(N3CCC(C(F)(F)F)CC3)nc21] | $C_{30}H_{34}Cl_2F_5N_7O_2$ 690.54 | 691 | Rt: 0.586 min Method G | 24e |
| 36 | 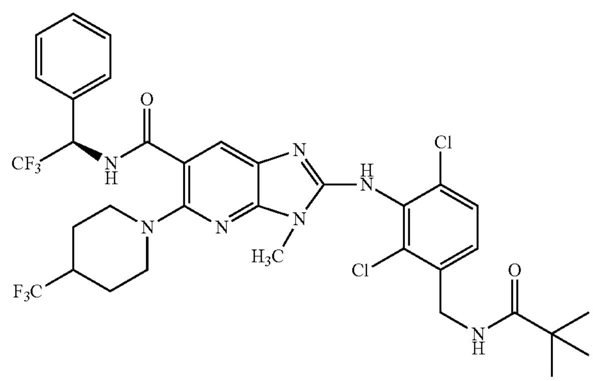 [SMILES: Cn1c(Nc2c(Cl)ccc(CNC(=O)C(C)(C)C)c2Cl)nc2cc(C(=O)N[C@H](c3ccccc3)C(F)(F)F)c(N3CCC(C(F)(F)F)CC3)nc21] | $C_{34}H_{35}Cl_2F_6N_7O_2$ 758.59 | 759 | Rt: 0.635 min Method G | 24e |
| 37 | 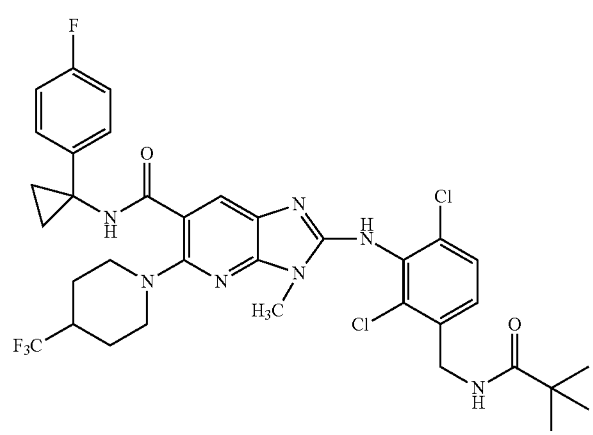 [SMILES: Cn1c(Nc2c(Cl)ccc(CNC(=O)C(C)(C)C)c2Cl)nc2cc(C(=O)NC3(c4ccc(F)cc4)CC3)c(N3CCC(C(F)(F)F)CC3)nc21] | $C_{35}H_{37}Cl_2F_4N_7O_2$ 734.62 | 735 | Rt: 0.611 min Method G | 24e |

TABLE II-continued examples

| Ex. | Structure | Formula/ Mw. | MS* m/z [M + H]+ | $R_F$ (TLC, silica gel) or $R_t$ [min] (HPLC-method) | Prepared in analogy to example |
|---|---|---|---|---|---|
| 38 | 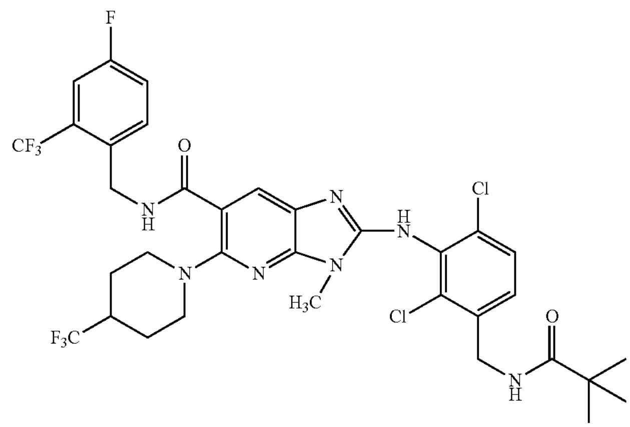 [SMILES: Cn1c(Nc2c(Cl)ccc(CNC(=O)C(C)(C)C)c2Cl)nc2cc(C(=O)NCc3ccc(F)cc3C(F)(F)F)c(N3CCC(C(F)(F)F)CC3)nc21] | $C_{34}H_{34}Cl_2F_7N_7O_2$ 776.58 | 777 | Rt: 0.631 min Method G | 24e |
| 39 | 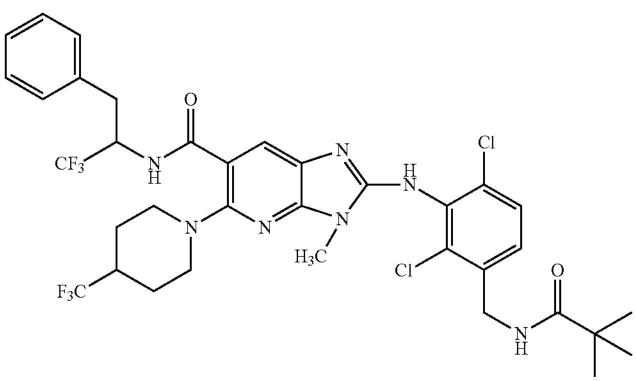 [SMILES: Cn1c(Nc2c(Cl)ccc(CNC(=O)C(C)(C)C)c2Cl)nc2cc(C(=O)NC(Cc3ccccc3)C(F)(F)F)c(N3CCC(C(F)(F)F)CC3)nc21] | $C_{35}H_{37}Cl_2F_6N_7O_2$ 772.62 | 773 | Rt: 0.638 min Method G | 24e |
| 40 | 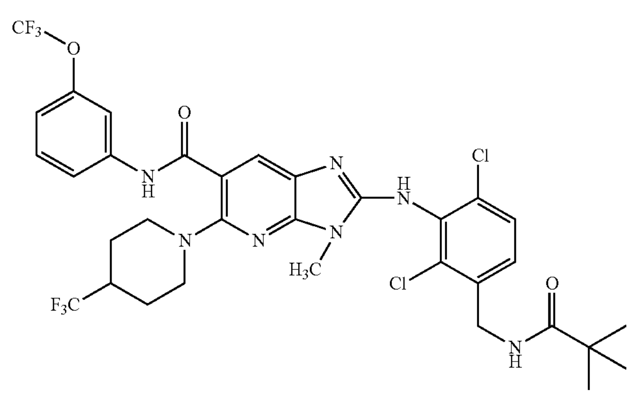 [SMILES: Cn1c(Nc2c(Cl)ccc(CNC(=O)C(C)(C)C)c2Cl)nc2cc(C(=O)Nc3cccc(OC(F)(F)F)c3)c(N3CCC(C(F)(F)F)CC3)nc21] | $C_{33}H_{33}Cl_2F_6N_7O_3$ 760.56 | 761 | Rt: 0.645 min Method G | 24e |

TABLE II-continued

| Ex. | Structure | Formula/ Mw. | MS* m/z [M + H]+ | $R_F$ (TLC, silica gel) or $R_t$ [min] (HPLC-method) | Prepared in analogy to example |
|---|---|---|---|---|---|
| 41 | 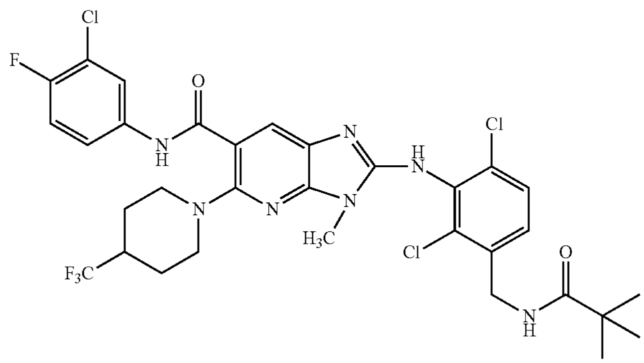 [SMILES: Cn1c(Nc2c(Cl)ccc(CNC(=O)C(C)(C)C)c2Cl)nc2cc(C(=O)Nc3ccc(F)c(Cl)c3)c(N3CCC(C(F)(F)F)CC3)nc21] | $C_{32}H_{32}Cl_3F_4N_7O_2$ 729.00 | 729 | Rt: 0.635 min Method G | 24e |
| 42 | 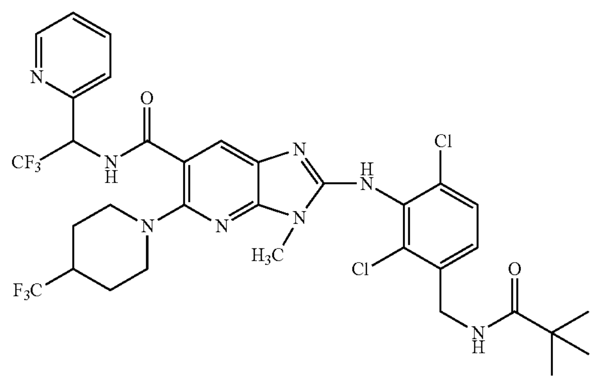 [SMILES: Cn1c(Nc2c(Cl)ccc(CNC(=O)C(C)(C)C)c2Cl)nc2cc(C(=O)NC(c3ccccn3)C(F)(F)F)c(N3CCC(C(F)(F)F)CC3)nc21] | $C_{33}H_{34}Cl_2F_6N_8O_2$ 759.58 | 760 | Rt: 0.623 min Method G | 24e |
| 43 | 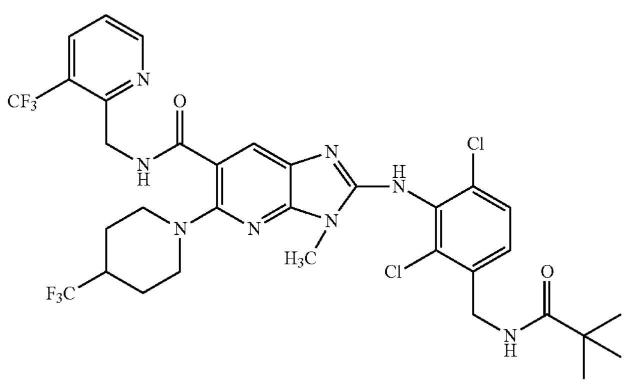 [SMILES: Cn1c(Nc2c(Cl)ccc(CNC(=O)C(C)(C)C)c2Cl)nc2cc(C(=O)NCc3ncccc3C(F)(F)F)c(N3CCC(C(F)(F)F)CC3)nc21] | $C_{33}H_{34}Cl_2F_6N_8O_2$ 759.58 | 760 | Rt: 0.610 min Method G | 24e |
| 44 | 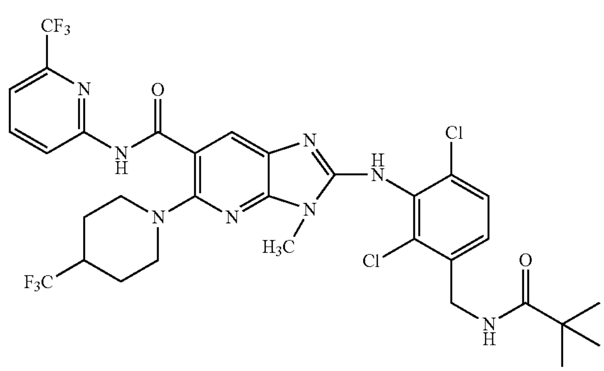 [SMILES: Cn1c(Nc2c(Cl)ccc(CNC(=O)C(C)(C)C)c2Cl)nc2cc(C(=O)Nc3cccc(C(F)(F)F)n3)c(N3CCC(C(F)(F)F)CC3)nc21] | $C_{32}H_{32}Cl_2F_6N_8O_2$ 745.55 | 746 | Rt: 0.650 min Method G | 24e |

TABLE II-continued examples

| Ex. | Structure | Formula/Mw. | MS* m/z [M + H]+ | $R_F$ (TLC, silica gel) or $R_t$ [min] (HPLC-method) | Prepared in analogy to example |
|---|---|---|---|---|---|
| 45 | 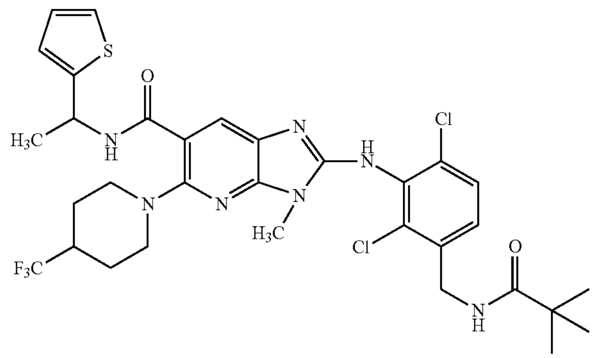 [SMILES: CC(NC(=O)c1cc2nc(Nc3c(Cl)ccc(CNC(=O)C(C)(C)C)c3Cl)n(C)c2nc1N1CCC(C(F)(F)F)CC1)c1cccs1] | $C_{32}H_{36}Cl_2F_3N_7O_2S$ 710.65 | 711 | Rt: 0.611 min Method G | 24e |
| 46 | 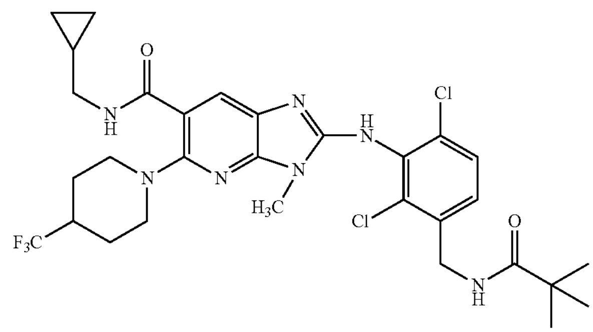 [SMILES: Cn1c(Nc2c(Cl)ccc(CNC(=O)C(C)(C)C)c2Cl)nc2cc(C(=O)NCC3CC3)c(N3CCC(C(F)(F)F)CC3)nc21] | $C_{30}H_{36}Cl_2F_3N_7O_2$ 654.56 | 655 | Rt: 0.589 min Method G | 24e |

The invention claimed is:
1. A compound of formula (I)

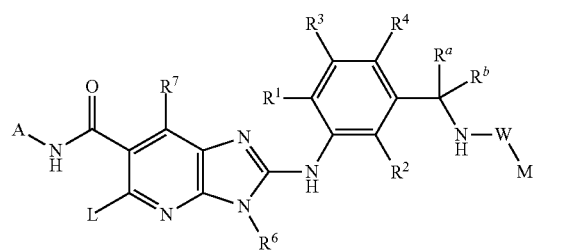

(I)

in which
R$^1$ represents halo, OH, —CN, C$_{1-3}$ alkyl, C$_{2-6}$ alkynyl, or OC$_{1-3}$ alkyl which latter three groups are optionally substituted by one or more substituents selected from fluoro, —CN, =O, OH, —OCH$_3$, or —OCF$_3$;

R$^2$, R$^3$ and R$^4$ independently represent hydrogen, halo, —CN, C$_{1-3}$ alkyl, or OC$_{1-3}$ alkyl which latter two groups are optionally substituted by one or more substituents selected from fluoro, —CN, =O, OH, —OCH$_3$, or —OCF$_3$;

R$^a$, R$^b$ independently represent hydrogen, or C$_{1-3}$ alkyl optionally substituted by one or more fluorine atoms, or both together with the carbon atom which they are bound to, form a C$_{3-7}$ cycloalkylene ring, or a 4-6 membered heterocycloalkylene ring which latter two rings are optionally substituted by one or more fluorine atoms;

W represents —C(O)—, —S(O)—, —S(O)$_2$—, —C(O)O—, or —C(O)NR$^d$— which groups are bound to the nitrogen of the —NH-moiety via carbon or sulfur atom;

R$^d$ represents hydrogen, or C$_{1-3}$ alkyl;

M represents C$_{1-8}$ alkyl, C$_{2-8}$ alkynyl, C$_{3-8}$ cycloalkyl-C$_{0-4}$ alkyl, or 4-10 membered heterocycloalkyl-C$_{0-4}$ alkyl- which latter four groups are optionally substituted by one or more groups selected from
  fluoro, —OH, =O, —CN, —NH$_2$, C$_{1-3}$ alkyl, —NH(C$_{1-3}$ alkyl), —N(C$_{1-3}$ alkyl)$_2$, azetidinyl, pyrrolidinyl, piperidinyl, or —OC$_{1-3}$ alkyl [which latter seven groups can be substituted by one or more substituents selected from fluoro, OH, —CN, or OC$_{1-2}$ alkyl (which latter alkyl group is optionally substituted by one or more fluorine atoms)], aryl, heteroaryl [which latter two groups are optionally substituted by one or more substituents selected from halo, OH, —CN, C$_{1-3}$ alkyl, or OC$_{1-3}$ alkyl (which latter two alkyl groups are optionally substituted by one or more fluorine atoms)], or
aryl, or heteroaryl which latter two groups are optionally substituted by one or more substituents selected from
  halo, —OH, —CN, —NH$_2$, aryl, heteroaryl [which latter two groups are optionally substituted by one or more substituents selected from halo, OH, —CN, C$_{1-3}$ alkyl, or —OC$_{1-3}$ alkyl (which latter two alkyl groups are optionally substituted by one or more fluorine atoms)], $C_{1-7}$ alkyl, $C_{2-7}$ alkynyl, $C_{3-7}$ cycloalkyl, 4-7 membered heterocyclo-alkyl, —NH($C_{1-3}$ alkyl), —N($C_{1-3}$ alkyl)$_2$, —O$C_{1-3}$ alkyl, —O—$C_{0-2}$alkyl-aryl, or —S$C_{1-3}$ alkyl, (which latter alkyl, alkynyl, heterocycloalkyl, aryl or cycloalkyl groups are optionally substituted by one or more substituents selected from fluoro, —CN, =O, —NH$_2$, —NH($C_{1-3}$ alkyl), —N($C_{1-3}$ alkyl)$_2$, —OH, or O$C_{1-3}$ alkyl)];

$R^6$ represents hydrogen, $C_{1-5}$ alkyl, $C_{3-6}$ alkynyl, 4-7 membered heterocyclo-alkyl-$C_{0-2}$alkyl or $C_{3-7}$cycloalkyl-$C_{0-2}$ alkyl (which latter four groups are optionally substituted by one or more substituents selected from fluoro, —CN, =O, $C_{1-3}$ alkyl, —OH, —NH$_2$, —O$C_{1-3}$ alkyl, —NH($C_{1-3}$ alkyl), or —N($C_{1-3}$ alkyl)$_2$);

$R^7$ represents hydrogen, halo, —CN, $C_{1-5}$ alkyl, $C_{3-5}$ cycloalkyl-$C_{0-2}$alkyl-, $C_{1-5}$ alkyl-O—, or $C_{3-5}$cycloalkyl-$C_{0-2}$ alkyl-O— (in which latter four groups the alkyl and cycloalkyl fragments are optionally substituted by one or more substituents selected from fluoro, —CN, =O, OH, or —O$C_{1-3}$ alkyl or by one or more $C_{1-3}$ alkyl groups which are optionally substituted by one or more fluorine atoms);

L represents —NH$_2$, —NHR$^{10}$, —NR$^{10}$R$^{11}$, or a 4-10-membered heterocycloalkyl group which is bound to the benzimidazole through a nitrogen atom, and which is optionally substituted by one or more substituents R$^{12}$;

$R^{10}$ and $R^{11}$ independently represent $C_{1-7}$ alkyl, $C_{3-7}$ cycloalkyl-$C_{0-4}$ alkyl-, or $C_{4-7}$ heterocycloalkyl-$C_{0-4}$ alkyl- [which latter three groups are optionally substituted by one or more groups selected from fluoro, —OH, NH$_2$, —CN, $C_{1-3}$ alkyl, —NH($C_{1-3}$ alkyl), —N($C_{1-3}$ alkyl)$_2$, —O$C_{1-5}$ alkyl, —O$C_{3-6}$ cycloalkyl, or —O$C_{4-6}$ heterocycloalkyl (which latter six groups are optionally substituted by one or more substituents selected from fluoro, —CF$_3$, —CHF$_2$, —CH$_2$F, or —CH$_3$)], or aryl-$C_{0-4}$ alkyl-, or heteroaryl-$C_{0-4}$ alkyl- [which latter two groups are optionally substituted by one or more substituents selected from halo, —OH, —CN, $C_{1-3}$ alkyl, $C_{3-5}$ cycloalkyl, or $C_{1-3}$ alkyl-O—, $C_{3-5}$ cycloalkyl-O— (which latter four groups are optionally substituted by one or more fluorine atoms)];

each $R^{12}$ independently represents halo, —OH, —NH$_2$, =O, —CN, $C_{1-4}$ alkyl, $C_{3-5}$cycloalkyl-$C_{0-2}$ alkyl-, $C_{4-5}$ heterocycloalkyl-$C_{0-2}$ alkyl-, $C_{1-4}$ alkyl-O—, $C_{1-3}$ alkyl-C(=O)—, —C(=O)—NH($C_{1-3}$ alkyl), or —C(=O)—N($C_{1-3}$ alkyl)$_2$ [which latter seven groups are optionally substituted by one or more groups selected from: fluoro, —OH, oxo, —NH$_2$, —CN, $C_{1-3}$ alkyl, —NH($C_{1-3}$ alkyl), —N($C_{1-3}$ alkyl)$_2$, —O$C_{1-3}$ alkyl, or —O$C_{3-5}$ cycloalkyl [which latter five groups are optionally substituted by one or more substituents selected from fluoro, —CF$_3$, —CHF$_2$, or —CH$_2$F], or aryl-$C_{0-4}$ alkyl-, or heteroaryl-$C_{0-4}$ alkyl- [which latter two groups are optionally substituted by one or more substituents selected from halo, —OH, —CN, $C_{1-3}$ alkyl, $C_{3-5}$ cycloalkyl, $C_{1-3}$ alkyl-O—, or $C_{3-5}$ cycloalkyl-O— (which latter four groups are optionally substituted by one or more fluorine atoms)];

A represents $C_{1-8}$ alkyl, $C_{3-8}$ alkynyl, aryl-$C_{0-3}$alkyl-, $C_{3-8}$ cycloalkyl-$C_{0-3}$ alkyl-, 4-7 membered heterocycloalkyl-$C_{0-3}$ alkyl-, or heteroaryl-$C_{0-3}$alkyl- in which latter six groups the alkyl-, alkynyl-, cycloalkyl- and heterocycloalkyl-fragments are optionally substituted by one or more substituents selected from R$^{14}$ and the aryl and heteroaryl fragments are optionally substituted by one or more substituents selected from R$^{15}$;

each $R^{14}$ independently represents fluoro, —OH, —CN, =O, —NH$_2$, —NH($C_{1-3}$ alkyl), —N($C_{1-3}$ alkyl)$_2$, —O$C_{1-6}$ alkyl, or $C_{1-6}$alkyl (in which latter four groups the alkyl fragments are optionally substituted by one or more substituents selected from fluoro, —CN, =O, —NH$_2$, —NH($C_{1-3}$ alkyl), N($C_{1-3}$ alkyl)$_2$, —OH, or —O$C_{1-3}$ alkyl) or aryl, or heteroaryl [which latter two groups are optionally substituted by one or more substituents selected from halo, OH, —CN, $C_{1-3}$ alkyl, or O$C_{1-3}$ alkyl (which latter two alkyl groups are optionally substituted by one or more fluorine atoms)];

each $R^{15}$ independently represents halo, —OH, —CN, —NH$_2$, aryl, heteroaryl [which latter two groups are optionally substituted by one or more substituents selected from halo, OH, —CN, $C_{1-3}$ alkyl, or O$C_{1-3}$ alkyl (which latter two alkyl groups are optionally substituted by one or more fluorine atoms)], —NH($C_{1-3}$ alkyl), —N($C_{1-3}$ alkyl)$_2$, —O$C_{1-3}$ alkyl, $C_{1-7}$ alkyl, $C_{2-7}$ alkynyl, $C_{3-7}$ cycloalkyl, or 4-7 membered heterocycloalkyl (which latter alkyl, alkynyl, heterocycloalkyl or cycloalkyl groups are optionally substituted by one or more substituents selected from fluoro, —CN, =O, —NH$_2$, —NH($C_{1-3}$ alkyl), N($C_{1-3}$ alkyl)$_2$, —OH, or O$C_{1-3}$alkyl);

or a salt thereof.

2. A compound according to claim 1, wherein
$R^1$ represents halo, or $C_{1-3}$ alkyl optionally substituted by one or more fluorine atoms;
or a pharmaceutically acceptable salt thereof.

3. A compound according to claim 1, wherein
$R^2$, $R^3$, $R^4$, $R^7$ independently represent hydrogen, fluoro, or chloro;
or a pharmaceutically acceptable salt thereof.

4. A compound according to claim 1, wherein
M represents $C_{1-6}$ alkyl, or $C_{3-8}$ cycloalkyl-$C_{0-1}$ alkyl- [which latter two groups are optionally substituted by one or more groups selected from fluoro, or $C_{1-3}$ alkyl optionally substituted by one or more fluorine atoms];
or a pharmaceutically acceptable salt thereof.

5. A compound according to claim 1, wherein
A represents $C_{1-6}$ alkyl, $C_{3-8}$cycloalkyl-$C_{0-3}$alkyl-, aryl-$C_{0-3}$alkyl-, or heteroaryl-$C_{0-3}$alkyl- in which latter four groups the alkyl- and cycloalkyl-fragments are optionally substituted by one or more substituents selected from R$^{14}$ and the aryl and heteroaryl fragments are optionally substituted by one or more substituents selected from R$^{15}$;
each $R^{14}$ independently represents fluoro, or $C_{1-3}$alkyl optionally substituted by one or more fluorine atoms or phenyl optionally substituted by one or more fluorine atoms;
each $R^{15}$ independently represents halo, —O$C_{1-3}$ alkyl, or $C_{1-3}$ alkyl, (which latter two alkyl groups are optionally substituted by one or more substituents fluorine atoms);
or a pharmaceutically acceptable salt thereof.

6. A compound according to claim 1, wherein
L represents —NH$_2$, —NHR$^{10}$, —NR$^{10}$R$^{11}$, or azetidinyl-, pyrrolidinyl-, piperidinyl-, morpholinyl or

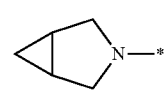

all of which heterocyclic groups are optionally substituted by one or more substituents $R^{12}$, while the above mentioned groups are bonded to the benzimidazole core through a nitrogen atom;

each $R^{10}$ and $R^{11}$ independently represent $C_{1-5}$ alkyl or $C_{3-6}$ cycloalkyl-$C_{0-1}$ alkyl-, or $C_{4-6}$ heterocycloalkyl-$C_{0-1}$ alkyl- [which latter three groups are optionally substituted by one or more groups selected from fluoro, —OH, —O$C_{1-3}$ alkyl, or $C_{1-3}$ alkyl (which latter two groups are optionally substituted by one or more fluorine atoms)], or aryl-$C_{0-1}$ alkyl-, or heteroaryl-$C_{0-1}$ alkyl- [which latter two groups are optionally substituted by one or more substituents selected from halo, —OH, —CN, $C_{1-3}$ alkyl, or $C_{1-3}$ alkyl-O— (which latter two groups are optionally substituted by one or more fluorine atoms)];

each $R^{12}$ independently represents fluoro, $C_{1-4}$ alkyl optionally substituted by one or more fluorine atoms, or phenyl optionally substituted by one or more substituents selected from halo, or $C_{1-3}$ alkyl which is optionally substituted by one or more fluorine atoms;

or a pharmaceutically acceptable salt thereof.

7. A compound according to claim 1, namely a compound of formula (Ia)

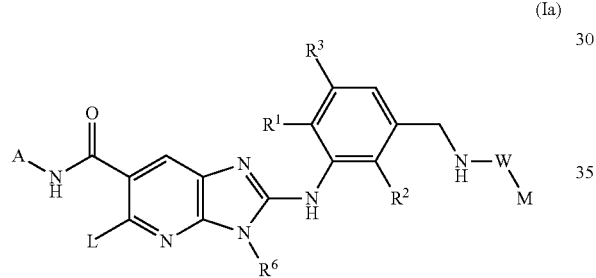

(Ia)

in which $R^1$ represents halo, or $C_{1-3}$ alkyl optionally substituted by one or more fluorine atoms;

$R^2$ and $R^3$ independently represent hydrogen, fluoro, or chloro;

$R^6$ represents hydrogen, $C_{1-5}$ alkyl, or $C_{3-5}$cycloalkyl-$C_{0-1}$ alkyl (which latter two groups are optionally substituted by one or more substituents selected from fluoro, =O, —NH$_2$, —NH($C_{1-3}$ alkyl) or —N($C_{1-3}$ alkyl)$_2$);

W represents —C(O)—, or —C(O)O— which groups are bound to the nitrogen of the —NH— moiety via the carbon atom;

M represents $C_{1-6}$ alkyl, or $C_{3-8}$ cycloalkyl-$C_{0-1}$ alkyl- [which latter two groups are optionally substituted by one or more groups selected from fluoro, $C_{1-3}$ alkyl optionally substituted by one or more fluorine atoms];

A represents $C_{1-6}$ alkyl, $C_{3-8}$ cycloalkyl-$C_{0-3}$alkyl-, aryl-$C_{0-3}$alkyl-, or heteroaryl-$C_{0-3}$alkyl- in which latter four groups the alkyl- and cycloalkyl-fragments are optionally substituted by one or more substituents selected from $R^{14}$ and the aryl and heteroaryl fragments are optionally substituted by one or more substituents selected from $R^{15}$;

each $R^{14}$ independently represents fluoro, $C_{1-3}$alkyl optionally substituted by one or more fluorine atoms or phenyl optionally substituted by one or more fluorine atoms;

each $R^{15}$ independently represents halo, —O$C_{1-3}$ alkyl, or $C_{1-3}$ alkyl, (which latter two alkyl groups are optionally substituted by one or more substituents fluorine atoms);

L represents —NH$_2$, —NHR$^{10}$, —NR$^{10}$R$^{11}$, or
azetidinyl-, pyrrolidinyl-, piperidinyl-, morpholinyl- or

all of which heterocyclic groups are optionally substituted by one or more substituents $R^{12}$, while the above mentioned groups are bonded to the benzimidazole core through a nitrogen atom;

each $R^{10}$ and $R^{11}$ independently represent $C_{1-5}$ alkyl, $C_{3-6}$ cycloalkyl-$C_{0-1}$ alkyl-, $C_{4-6}$ heterocycloalkyl-$C_{0-1}$ alkyl- [which latter three groups are optionally substituted by one or more groups selected from fluoro, —OH, —O$C_{1-3}$ alkyl or $C_{1-3}$ alkyl (which latter two groups are optionally substituted by one or more fluorine atoms)], or aryl-$C_{0-1}$ alkyl-, or heteroaryl-$C_{0-1}$ alkyl- [which latter two groups are optionally substituted by one or more substituents selected from halo, —OH, —CN, $C_{1-3}$ alkyl or $C_{1-3}$ alkyl-O— (which latter two groups are optionally substituted by one or more fluorine atoms)];

each $R^{12}$ independently represents fluoro, $C_{1-4}$ alkyl optionally substituted by one or more fluorine atoms, or phenyl optionally substituted by one or more substituents selected from halo, or $C_{1-3}$ alkyl which is optionally substituted by one or more fluorine atoms;

or a salt thereof.

8. A compound according to claim 1, wherein

A represents $C_{1-5}$ alkyl, phenyl-$C_{0-2}$alkyl-, $C_{3-6}$ cycloalkyl-$C_{0-1}$alkyl-, pyridinyl-$C_{0-1}$alkyl-, or thienyl-$C_{0-1}$alkyl- in which latter five groups the alkyl- and cycloalkyl-fragments are optionally substituted by one or more substituents selected from $R^{14}$ and the phenyl, pyridinyl and thienyl fragments are optionally substituted by one or more substituents selected from $R^{15}$;

each $R^{14}$ independently represents fluoro, CH$_3$, CH$_2$F, CHF$_2$, CF$_3$ or phenyl optionally substituted by one or more fluorine atoms;

each $R^{15}$ independently represents fluoro, chloro, CH$_3$, CH$_2$F, CHF$_2$, CF$_3$ or —OCH$_3$, —OCH$_2$F, —OCHF$_2$, or —OCF$_3$;

or a pharmaceutically acceptable salt thereof.

9. A compound according to claim 1, wherein

M represents $C_{1-6}$ alkyl, or $C_{3-6}$ cycloalkyl- [which latter two groups are optionally substituted by one or more groups selected from fluoro, CH$_3$, CH$_2$F, CHF$_2$, or CF$_3$];

or a pharmaceutically acceptable salt thereof.

10. A compound according to claim 1, wherein

L represents —NH$_2$, —NHR$^{10}$, —NR$^{10}$R$^{11}$, or
azetidinyl-, pyrrolidinyl-, piperidinyl-, morpholinyl or

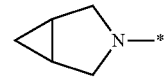

all of which heterocyclic groups are optionally substituted by one or more substituents $R^{12}$, while the above mentioned groups are bonded to the benzimidazole core through a nitrogen atom;

each $R^{10}$ and $R^{11}$ independently represent $C_{1-5}$-alkyl, $C_{3-6}$-cycloalkyl-$C_{0-1}$ alkyl- or oxetanyl-$C_{0-1}$ alkyl- [which latter three groups are optionally substituted by one or more groups selected from fluoro, —OH, —OCH$_3$, —OCH$_2$F, —OCHF$_2$, —OCF$_3$ or CH$_3$, CH$_2$F, CHF$_2$, or CF$_3$], or imidazolyl-$C_{0-1}$ alkyl- or 1,2,4-triazolyl-$C_{0-1}$ alkyl- [which latter two groups are optionally substituted by one or more substituents selected from CH$_3$, CH$_2$F, CHF$_2$, or CF$_3$];

each $R^{12}$ independently represents fluoro, CH$_3$, CH$_2$F, CHF$_2$, or CF$_3$;

or a pharmaceutically acceptable salt thereof.

11. A compound according to claim 1, namely a compound of formula (Ib)

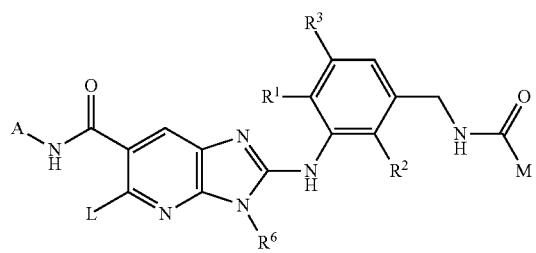

(Ib)

in which $R^1$ represents fluoro, or chloro;

$R^2$ represents hydrogen, fluoro, or chloro;

$R^3$ represents hydrogen or fluoro;

$R^6$ represents hydrogen, CH$_3$;

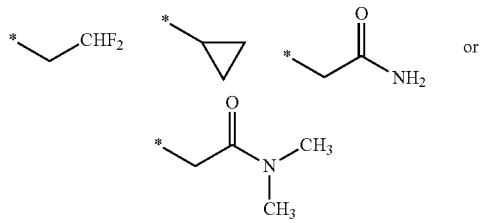

M represents a group selected from

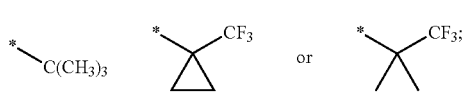

A represents a group selected from

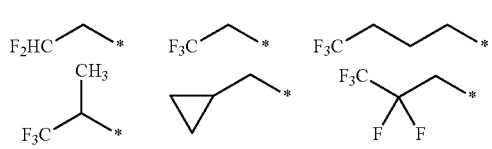

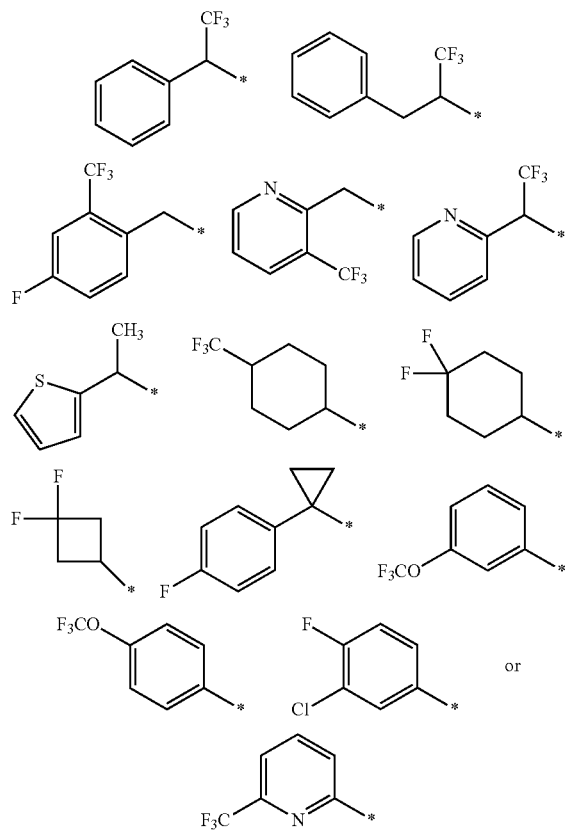

L represents a group selected from

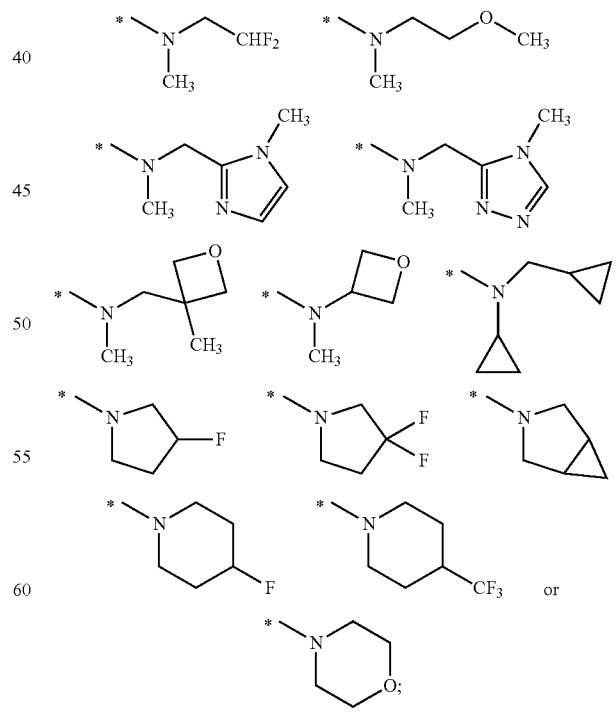

or a salt thereof.

12. A compound according to claim 1 selected from the following compounds:
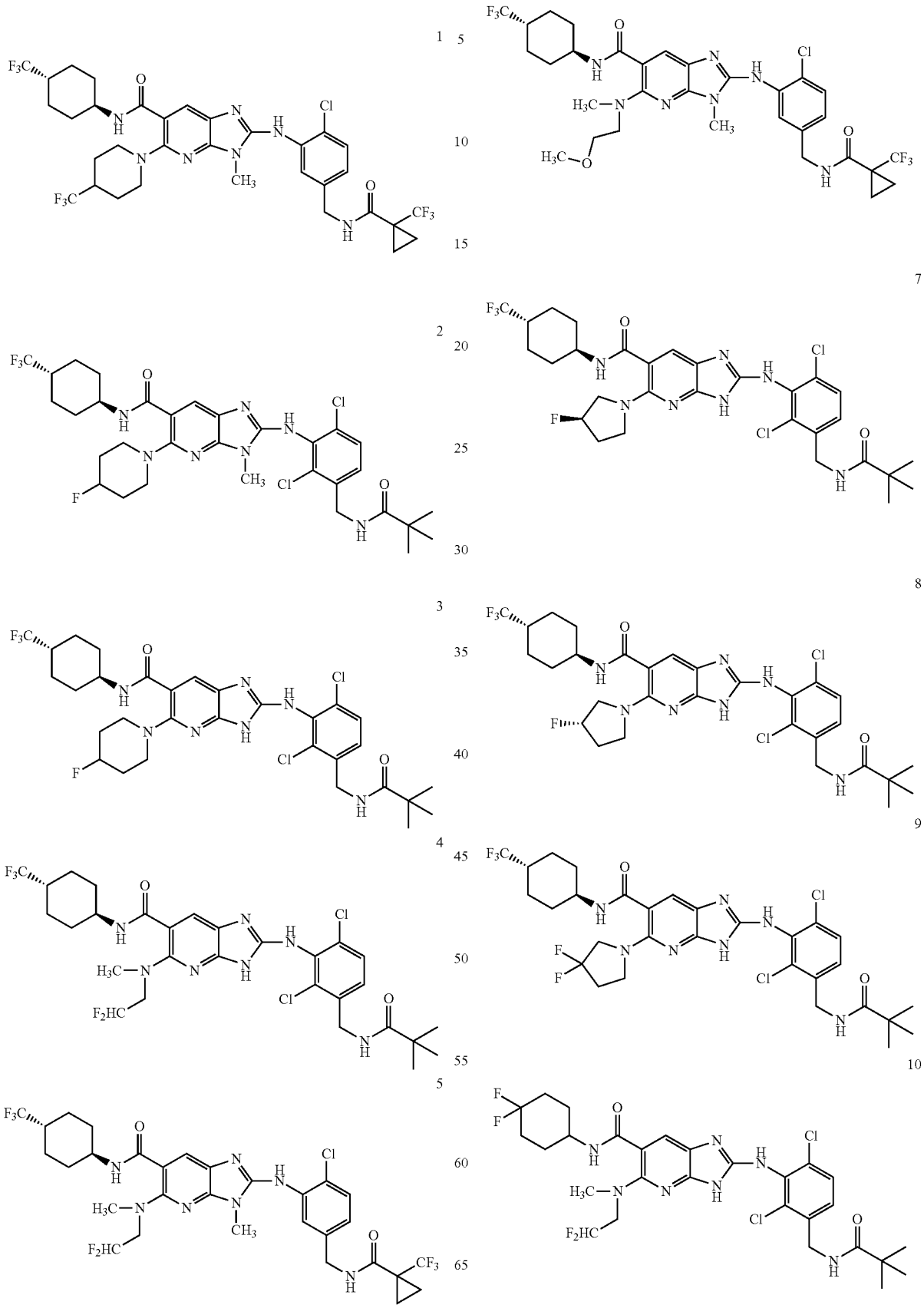

11
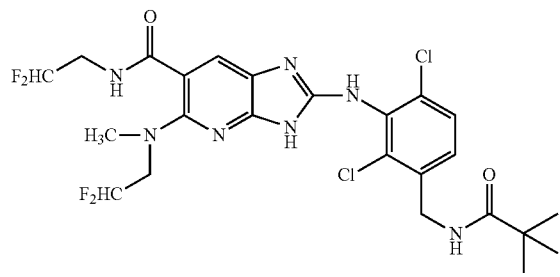
12
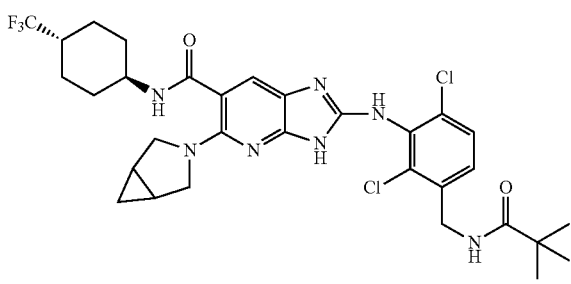
14
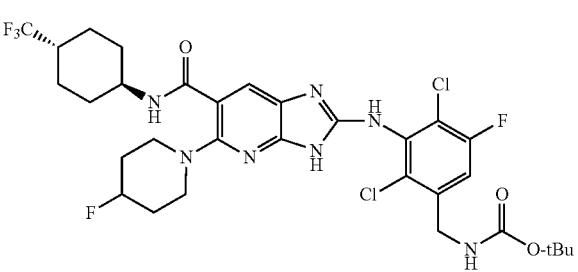
15
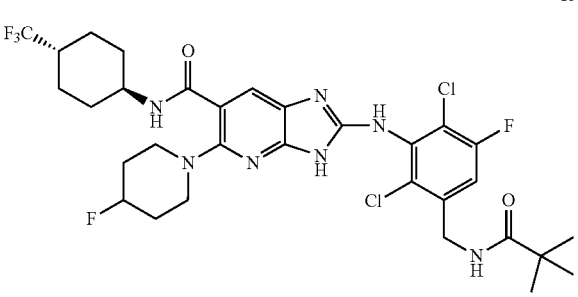
16
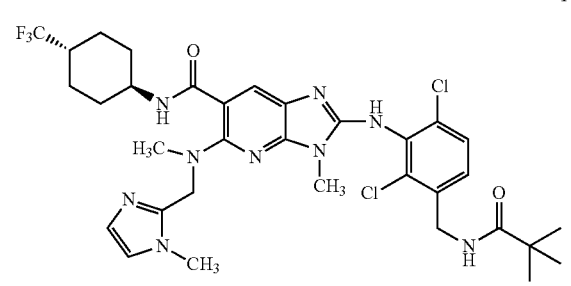
17
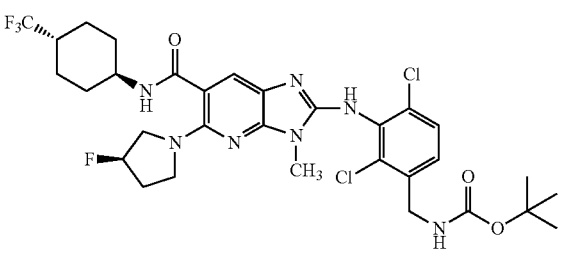
18
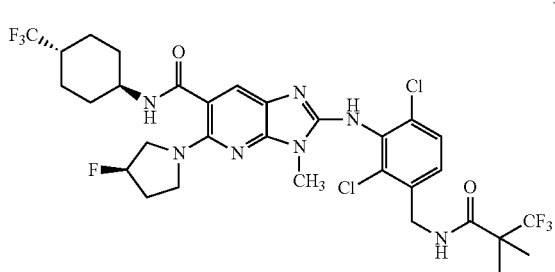
19
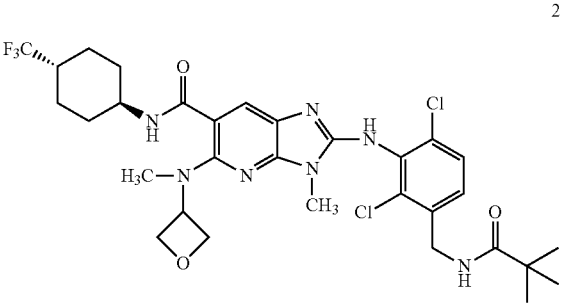
20
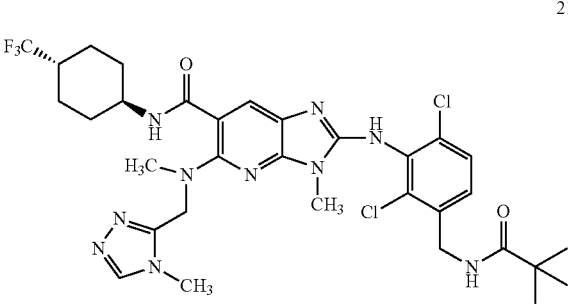
21

-continued
22
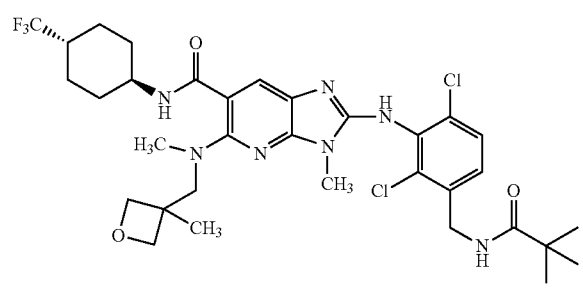
23
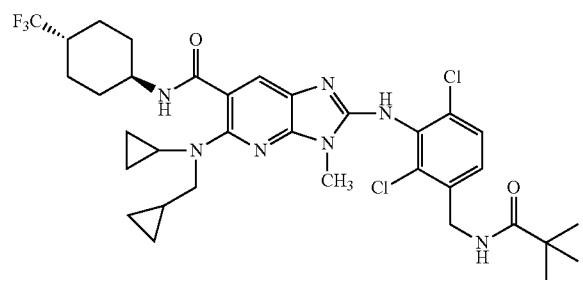
24
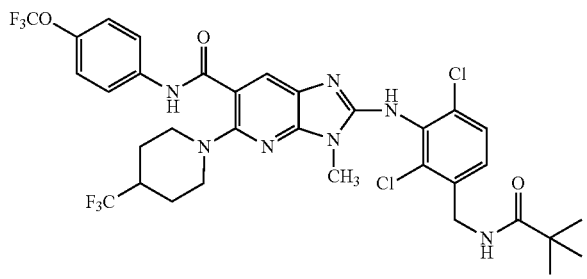
25
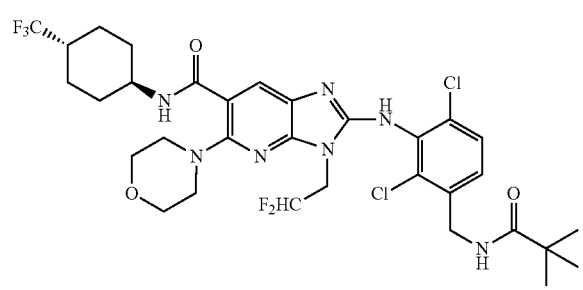
26
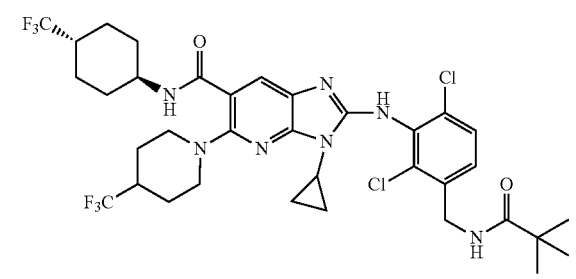
-continued
27
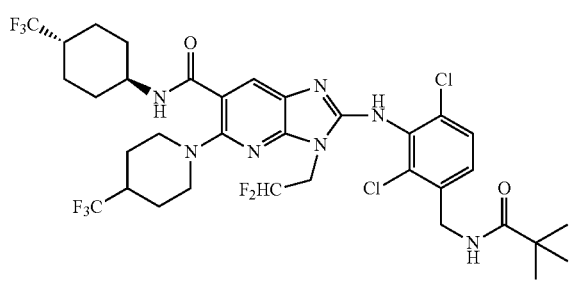
28
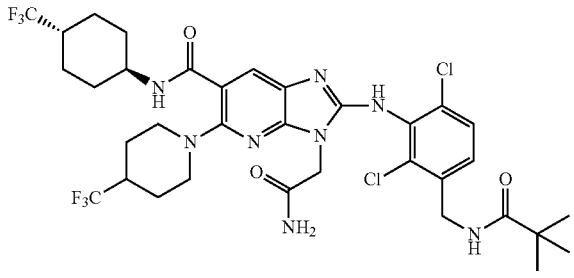
29
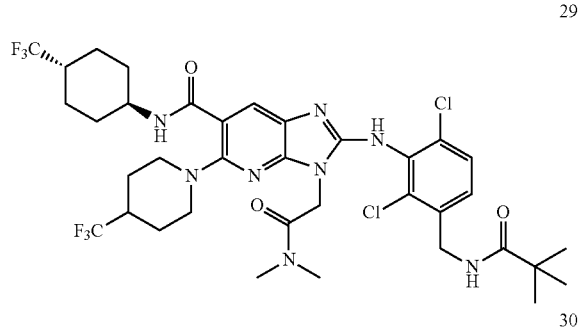
30
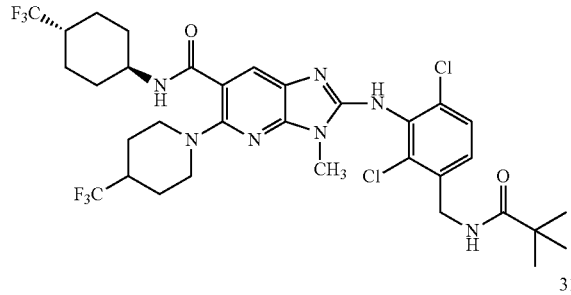
31
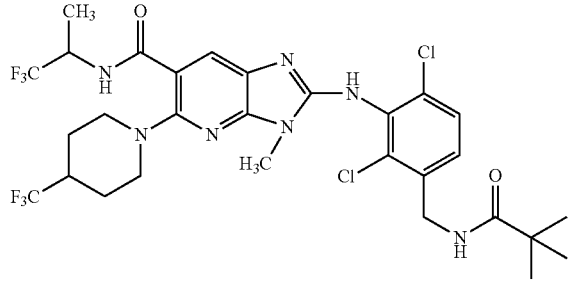

-continued
32
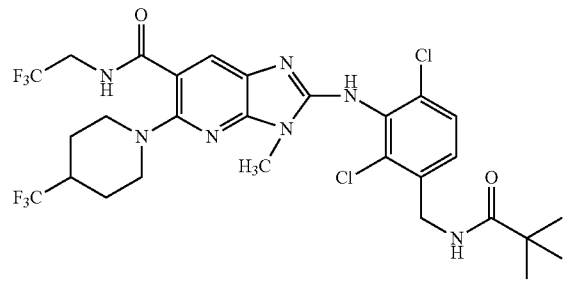
33
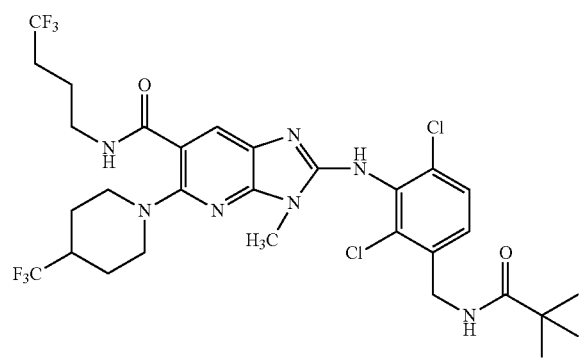
34
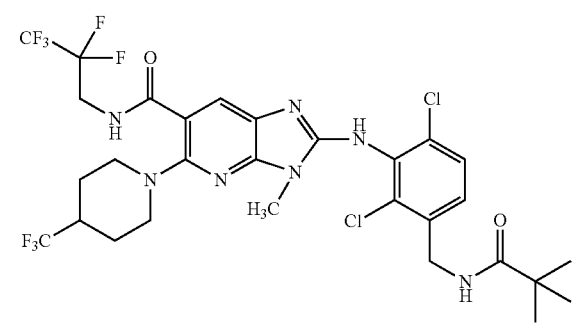
35
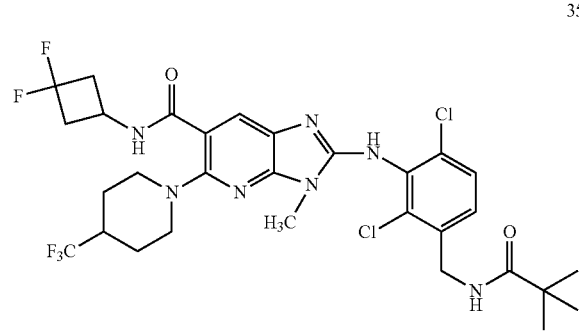
-continued
36
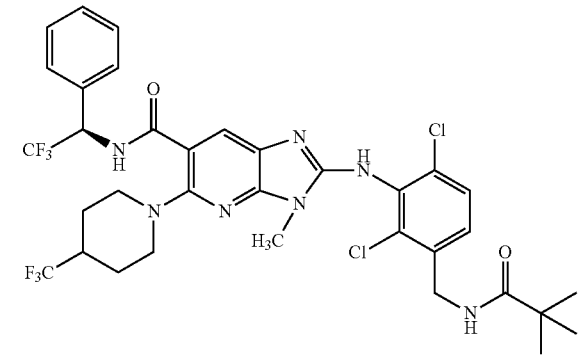
37
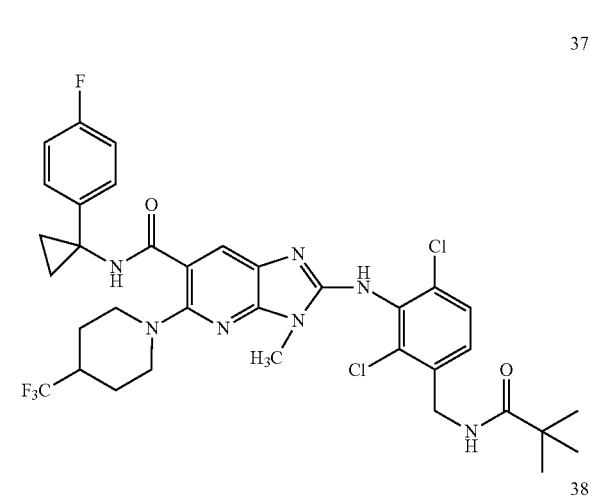
38
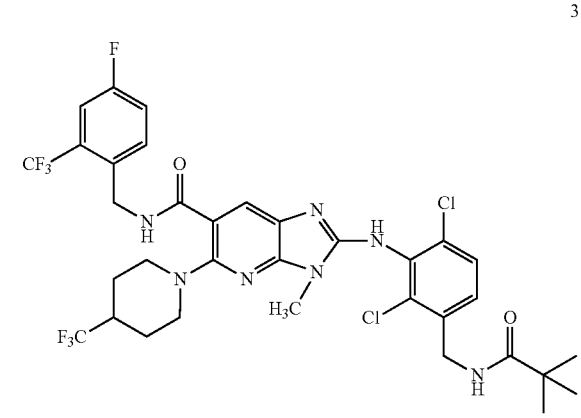
39
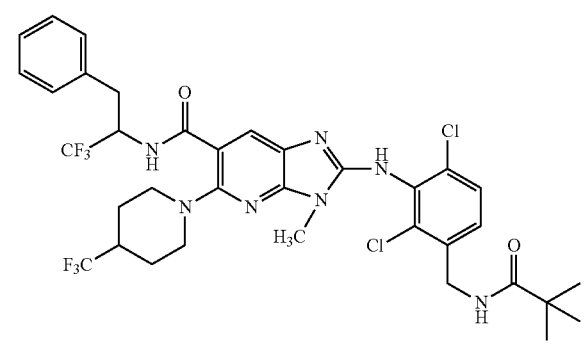

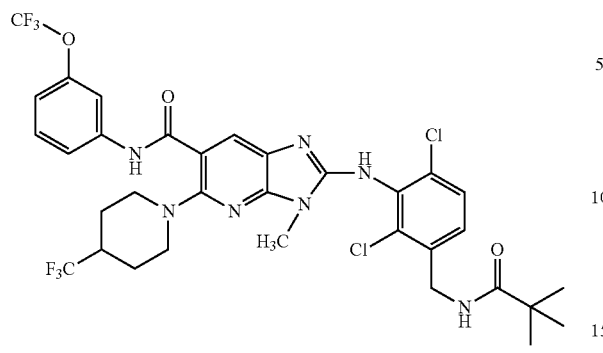

40

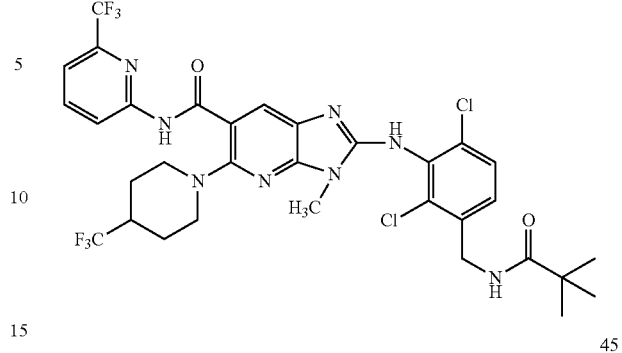

44

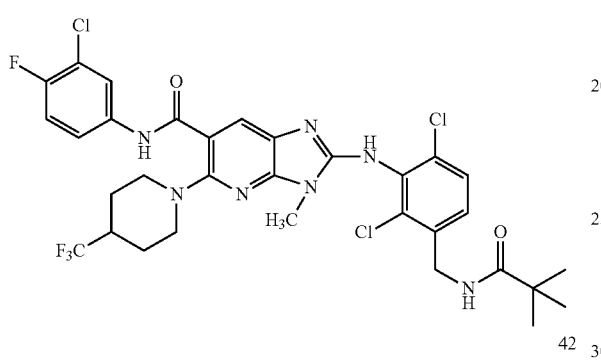

41

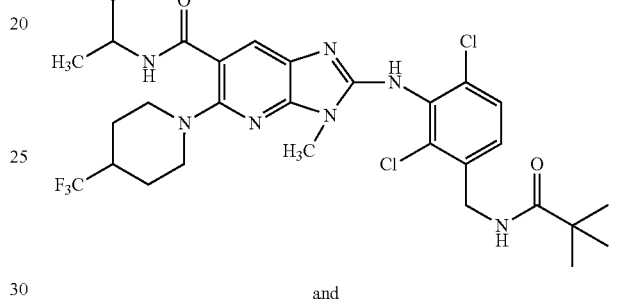

45

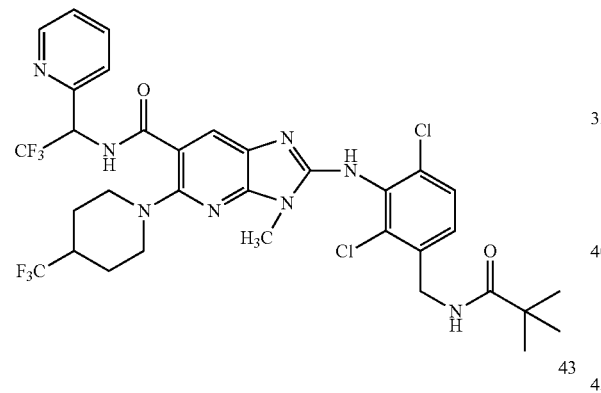

42

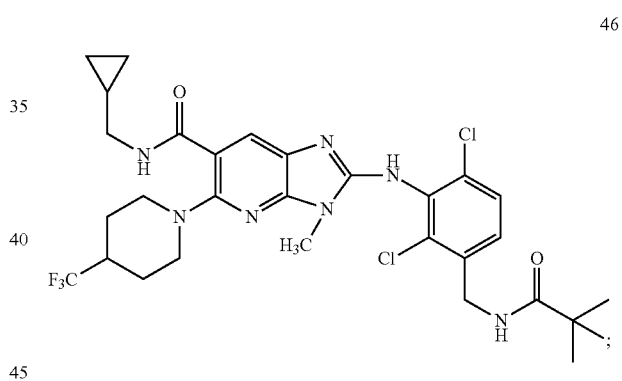

and

46

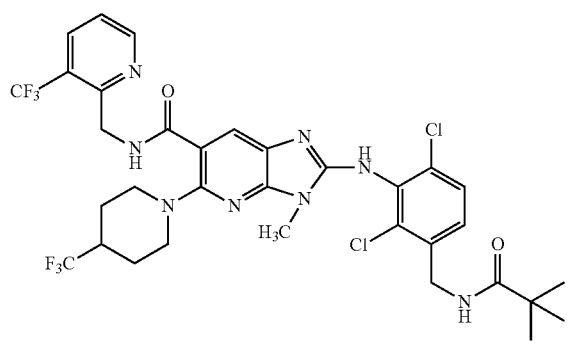

43 or pharmaceutically acceptable salts thereof.

13. A pharmaceutical composition comprising at least one compound according to claim 1, or a pharmaceutically acceptable salt thereof, in a mixture with a pharmaceutically acceptable adjuvant, diluent and/or carrier.

14. A method for the treatment or prevention of an inflammatory disease in a patient comprising administering to said patient a therapeutically effective amount of a compound according to claim 1, or a pharmaceutically acceptable salt thereof.

* * * * *